(12) United States Patent
Chasle

(10) Patent No.: US 10,517,943 B2
(45) Date of Patent: Dec. 31, 2019

(54) STABLE LIQUID VACCINIA VIRUS FORMULATIONS

(71) Applicant: Transgene SA, Illkirch Graffenstaden (FR)

(72) Inventor: Mélina Chasle, Strasbourg (FR)

(73) Assignee: Transgene S.A., Illkirch Graffenstaden (FR)

( * ) Notice: Subject to any disclaimer, the term of this patent is extended or adjusted under 35 U.S.C. 154(b) by 0 days.

(21) Appl. No.: 15/529,668

(22) PCT Filed: Dec. 1, 2015

(86) PCT No.: PCT/EP2015/078239
§ 371 (c)(1),
(2) Date: May 25, 2017

(87) PCT Pub. No.: WO2016/087457
PCT Pub. Date: Jun. 9, 2016

(65) Prior Publication Data
US 2017/0326230 A1    Nov. 16, 2017

(30) Foreign Application Priority Data

Dec. 1, 2014  (EP) .................................... 14306930

(51) Int. Cl.
| | | |
|---|---|---|
| A61K 39/275 | (2006.01) | |
| A61K 9/08 | (2006.01) | |
| A61K 39/12 | (2006.01) | |
| A61K 47/10 | (2017.01) | |
| A61K 47/18 | (2017.01) | |
| A61K 47/26 | (2006.01) | |
| A61K 9/00 | (2006.01) | |

(52) U.S. Cl.
CPC .......... *A61K 39/275* (2013.01); *A61K 9/0019* (2013.01); *A61K 9/08* (2013.01); *A61K 39/12* (2013.01); *A61K 47/10* (2013.01); *A61K 47/183* (2013.01); *A61K 47/26* (2013.01); *C12N 2710/24034* (2013.01)

(58) Field of Classification Search
None
See application file for complete search history.

(56) References Cited

U.S. PATENT DOCUMENTS

| 3,915,794 | A | 10/1975 | Zygraich et al. |
| 4,675,187 | A | 6/1987 | Konishi et al. |
| 5,879,924 | A | 3/1999 | Foster et al. |
| 6,241,989 | B1 * | 6/2001 | Scott ................. C07K 14/005 424/199.1 |
| 7,456,009 | B2 | 11/2008 | Evans et al. |
| 7,914,979 | B2 | 3/2011 | Chen et al. |
| 8,795,683 | B2 * | 8/2014 | Oberreither .......... A61K 9/1623 424/199.1 |
| 2007/0161085 | A1 | 7/2007 | Trager et al. |

FOREIGN PATENT DOCUMENTS

| EP | 0 252 059 | 1/1988 |
| EP | 1 418 942 | 5/2004 |
| WO | WO 88/07378 | 10/1988 |
| WO | WO 90/10459 | 9/1990 |
| WO | WO 91/11201 | 8/1991 |
| WO | WO 92/07000 | 4/1992 |
| WO | WO 95/09241 | 4/1995 |
| WO | WO 98/04705 | 2/1998 |
| WO | WO 99/03885 | 1/1999 |
| WO | WO 99/54481 | 10/1999 |
| WO | WO 2004/111082 | 12/2004 |
| WO | WO 2005/007840 | 1/2005 |
| WO | WO 2005/007857 | 1/2005 |
| WO | WO 2005/066333 | 7/2005 |
| WO | WO 2007/030668 | 3/2007 |
| WO | WO 2007/077256 | 7/2007 |
| WO | WO 2007/121894 | 11/2007 |
| WO | WO 2007/147528 | 12/2007 |
| WO | WO 2008/113078 | 9/2008 |
| WO | WO 2009/004016 | 1/2009 |
| WO | WO 2009/065546 | 5/2009 |
| WO | WO 2009/065547 | 5/2009 |
| WO | WO 2010/130753 | 11/2010 |
| WO | WO 2014/009433 | 1/2014 |
| WO | WO 2014/009438 | 1/2014 |
| WO | WO 2014/029702 | 2/2014 |

OTHER PUBLICATIONS

Michalski et al., Infection and Immunity, 1976, 14(1):135-143 (Year: 1976).*
Kaplan et al., J. Gen. Microbial., 1963, 31:311-314. (Year: 1963).*
Aitken (TE buffer (Tris-EDTA buffer); http://www.nhm.ac.uk/content/dam/nhmwww/our-science/dpts-facilities-staff/ Coreresearchlabs/te-buffer.pdf) (Year: 2012).*
Antoine et al., *The Complete Genomic Sequence of the Modified Vaccinia Ankara Strain: Comparison with Other Orthopoxviruses*, 244 Virology 365-396 (1998).
Burke et al., *Formulation, Stability, and Delivery of Live Attenuated Vaccines for Human Use*, 16(1) Critical Reviews in Therapeutic Drug Carrier Systems 1-83 (1999).
Evans et al., *Development of stable liquid formulations for adenovirus-based vaccines*, 93(10) Journal of Pharmaceutical Sciences 2458-2475 (Oct. 2004).
Ezzeddine et al., *Selective Killing Of Glioma Cells in Culture and in Vivo by Retrovirus Transfer Of The Herpes Simplex Virus Thymidine Kinase Gene*, 3(6) The New Biologist 608-614 (1991).

(Continued)

*Primary Examiner* — Nicole Kinsey White
(74) *Attorney, Agent, or Firm* — Buchanan Ingersoll & Rooney, PC

(57) ABSTRACT

The present invention relates to liquid formulations of poxvirus, in particular vaccinia virus, stable during storage. Such stable liquid formulations comprise a) a poxvirus, preferably a vaccinia virus, b) a pharmaceutically acceptable buffer, c) a monovalent salt, d) a pharmaceutically acceptable disaccharide or sugar alcohol, and e) a pharmaceutically acceptable chelating agent, wherein the pH of the formulation is comprised between 6.5 and 8.5.

21 Claims, 28 Drawing Sheets

(56) References Cited

OTHER PUBLICATIONS

Goebel et al., The Complete DNA Sequence of Vaccinia Virus, 179 Virology 247-266 (1990).

Goebel et al., Appendix to "The Complete DNA Sequence of Vaccinia Virus,"179 Virology 517-563 (1990).

Gómez et al., The Poxvirus Vectors MVA and NYVAC as Gene Delivery Systems for Vaccination Against Infectious Diseases and Cancer, 8 Current Gene Therapy 97-120 (2008).

Ivanov et al., Establishment and characterization of a permanent duck embryo cell line, Experimental Pathology and Parasitology 41-44 (2000).

Johnson et al., An Update on the Vaccinia Virus Genome, 196 Virology 381-401 (1993).

Kim et al., Systemic Armed Oncolytic and Immunologic Therapy for Cancer with JX-594, a Targeted Poxvirus Expressing GM-CSF, 14(3) Molecular Therapy 361-370 (Sep. 2006).

Kim et al., Targeted and armed oncolytic poxviruses: a novel multi-mechanistic therapeutic class for cancer, 9 Nature 64-71 (Jan. 2009).

Lamb et al., Nucleotide sequence of cloned cDNA coding for preproricin, 148 Eur. J. Biochem. 265-270 (1985).

Liu et al., Gene-based vaccines and immunotherapeutics, 101(2) PNAS 14567-14571 (Oct. 5, 2004).

Lytle et al., Predicted Inactivation of Viruses of Relevance to Biodefense by Solar Radiation, 79(22) Journal of Virology 14244-14252 (2005).

Massey, Catalytic antibodies catching on, 328 Nature 457-458 (Jul. 30, 1987).

Mayr et al., Passage history, properties and applications of the attenuated vaccinia virus strain MVA, 3(1) Infection 6-14 (1975).

Moolten, Tumor Chemosensitivity Conferred by Inserted Herpes Thymidine Kinase Genes: Paradigm for a Prospective Cancer Control Strategy, 46 Cancer Research 5276-5281 (Oct. 1986).

Mullen et al., Transfer of the bacterial gene for cytosine deaminase to mammalian cells confers lethal sensitivity to 5-fluorocytosine: A negative selection system, 89 Proc. Natl. Acad. Sci. USA 33-37 (Jan. 1992).

Osborne et al., Genomic differences of Vaccinia virus clones from Dryvax smallpox vaccine: The Dryvax-like ACAM2000 and the mouse neurovirulent Clone 3, 25 Vaccine 8807-8832 (2007).

Rexroad et al., Lyophilization and the Thermostability of Vaccines, 1(2) Cell Preservation Technology 91-104 (Nov. 2, 2002).

Rochlitz et al., Phase I immunotherapy with a modified vaccinia virus (MVA) expressing human $MUC_1$, as antigen-specific immunotherapy in patients with $MUC_1$-positive advanced cancer, 5 J Gene Med 690-699 (2003).

Shi et al., Stabilization of Human Papillomavirus Virus-Like Particles by Non-Ionic Surfactants, 94(7) Journal of Pharmaceutical Sciences 1538-1551 (Jul. 2005).

Tougu et al., Electrostatic effects in trypsin reactions, 222 Eur. J. Biochem 475-481 (1994).

International Search Report based on corresponding PCT Application No. PCT/EP2015/078239 dated Mar. 4, 2016.

* cited by examiner

A Infectious losses of MVA-HCV at +37°C depending on Na glutamate concentration

Figure 5A

B Infectious losses of MVA-HCV at +25°C depending on Na glutamate concentration

Figure 5B

C    Infectious losses of MVA-HCV at +5 °C depending on Na glutamate concentration

Figure 5C

Infectious losses of MVA-MUC1 at +37 °C depending on sucrose concentration

Figure 6

C  Infectious losses of VV Wyeth at +37°C

Figure 7C

A  Infectious losses after 14 days at +37°C depending on MgCl2 concentration

Figure 8A

B  Infectious losses of VV Wyeth at +37°C

Time (days)

■ Tris+sucrose

▨ Tris+ sucrose+ MgCl2 1000mM

Figure 8B

Infectious losses of MVA-MUC1 at +37°C depending on presence of a mixture of amino acids (aa)

Figure 10

A Infectious losses of MVA-HCV at +37°C depending on pH

Figure 12A

B Infectious losses of MVA-HCV at +5°C depending on pH

Figure 12B

A Infectious losses of MVA-HCV at +37°C depending on MVA concentration

- DS - 1.0E08 PFU/mL
- DS - 5.0E07 PFU/mL
- DS - 1.0E07 PFU/mL
- DS - 5.0E06 PFU/mL
- Inv - 1.0E08 PFU/mL
- Inv - 5.0E07 PFU/mL
- Inv - 1.0E07 PFU/mL
- Inv - 5.0E06 PFU/mL

Figure 13A

B Infectious losses of MVA-HCV at +25°C depending on MVA concentration

- DS - 1.0E08 PFU/mL
- DS - 5.0E07 PFU/mL
- DS - 1.0E07 PFU/mL
- DS - 5.0E06 PFU/mL
- Inv - 1.0E08 PFU/mL
- Inv - 5.0E07 PFU/mL
- Inv - 1.0E07 PFU/mL
- Inv - 5.0E06 PFU/mL

Figure 13B

C Infectious losses of MVA-HCV at +5 °C depending on MVA concentration

- DS - 1.0E08 PFU/mL
- DS - 5.0E07 PFU/mL
- DS - 1.0E07 PFU/mL
- DS - 5.0E06 PFU/mL
- Inv - 1.0E08 PFU/mL
- Inv - 5.0E07 PFU/mL
- Inv - 1.0E07 PFU/mL
- Inv - 5.0E06 PFU/mL

Figure 13C

A Infectious losses of various strains of vaccinia virus obtained by various methods at +37 °C

- ■ MVA-HCV/CEC (control)
- ▨ MVA-HCV/CEC (formulated)
- ▦ MVA-HCV/avian cell line (control)
- ▩ MVA-HCV/avian cell line (formulated)
- ▤ MVA-FCU1/CEC (control)
- ▦ MVA-FCU1/CEC (formulated)
- ☐ Copenhaguen-FCU1/CEC (control)
- ☰ Copenhaguen-FCU1/CEC (formulated)

Figure 15A

B Infectious losses of Wyeth VV at +37°C

Infectious titer losses of MVA-HCV at +25 °C depending on light conditions

■ Control-without light
▨ Optimized-without light
■ Control-PSM
▨ Optimized-PSM
▨ Control-ICH
▨ Optimized-ICH

Figure 17A

B Infectious losses at of MVA-HCV at +25 °C under ICH light in various formulations ■ Formulation EDTA + EtOH (no light)

▨ Control (ICH)

▓ Formulation EDTA + EtOH (ICH)

▨ Formulation EDTA (ICH)

▨ Formulation EtOH (ICH)

Figure 17B

STABLE LIQUID VACCINIA VIRUS FORMULATIONS

CROSS-REFERENCE TO RELATED APPLICATIONS

This application is a U.S. National Stage Application pursuant to 35 U.S.C. § 371 of International Patent Application PCT/EP2015/078239, filed on Dec. 1, 2015, and published as WO 2016/087457 on Jun. 9, 2016, which claims priority to European Patent Application 14306930.0, filed on Dec. 1, 2014, all of which are incorporated herein by reference in their entireties for all purposes.

TECHNICAL FIELD OF THE INVENTION

The present invention is in the field of stable liquid formulations intended for liquid storage of poxviruses, in particular vaccinia viruses. It relates to liquid formulations comprising a) a poxvirus, in particular a vaccinia virus, b) a pharmaceutically acceptable buffer, c) a monovalent salt, d) a pharmaceutically acceptable disaccharide or sugar alcohol, and e) a pharmaceutically acceptable chelating agent, wherein the pH of the formulation is comprised between 6.5 and 8.5.

BACKGROUND ART

Poxviruses are complex enveloped viruses having a diameter comprised between 200 and 300 nm that distinguish them principally by their unusual morphology, their large DNA genome and their cytoplasmic site of replication. The genome of several members of Orthopoxviruses, including two strains of vaccinia virus (VV): the Copenhagen Vaccinia Virus strain (GOEBEL et al., 1990, Virol. 179, 247-266 and 517-563; JOHNSON et al., 1993, Virol. 196, 381-401), the Wyeth strain (OSBORNE J D et al. Vaccine. 2007 Dec. 17; 25(52):8807-32) and the modified Vaccinia Virus Ankara (MVA) strain (ANTOINE et al., 1998, Virol. 244:365-396), have been mapped and sequenced. VV has a double-stranded DNA genome of about 192 kb coding for about 200 proteins of which approximately 100 are involved in virus assembly. MVA is a highly attenuated Vaccinia Virus strain generated by more than 500 serial passages of the Ankara strain of Vaccinia Virus on chicken embryo fibroblasts (MAYR et al., 1975, Infection 3:6-16). The MVA virus was deposited at Collection Nationale de Cultures de Microorganismes (CNCM) under depositary N° I-721. Determination of the complete sequence of the MVA genome and comparison with the Copenhagen VV genome allow the precise identification of the alterations which occurred in the viral genome and the definition of seven deletions (I to VII) and numerous mutations leading to fragmented ORFs (Open Reading Frame) (ANTOINE et al., 1998, Virology 244:365-396).

MVA is used as a prophylactic vaccine against smallpox and recombinant MVA is currently the subject of many preclinical and clinical studies for prophylactic and therapeutic vaccination against many types of targets, including cancer (melanoma, non-small cell lung carcinoma, renal cell carcinoma, prostate cancer, colorectal cancer, notably), viral (hepatitis B or C, HIV notably), bacterial (tuberculosis notably) and parasitic diseases (malaria notably) (see GOMEZ et al. Current Gene Therapy, 2008, 8:97-120).

Oncolytic vaccinia viruses are also under preclinical and clinical development (see KIRN et al. Nat Rev Cancer, 2009 January, 9(1):64-71).

In both cases, a live vaccinia virus is used.

A live vaccinia virus prophylactic or therapeutic vaccine is generally not administered to the patient just after production and purification, and thus needs to be stored for days, weeks or even months, without losing its potency.

Like all live viruses, live vaccinia viruses have natural instability, which is further increased by the fact that vaccinia virus is an enveloped virus (enveloped viruses are known to be less stable than non-enveloped viruses, see BURKE C J et al. Crit Rev Ther Drug Carrier Syst. 1999, 16(1):1-83; and REXROAD et al. Cell Preservation Technology. June 2002, 1(2):91-104), has a big size (brick shape of 200 to 300 nm), a large genome and is known to be particularly sensitive to UV damage, see LYTLE et al. J. Virol. 2005, 79(22):14244). Moreover, vaccinia virus envelop is even more complex than that of other enveloped viruses. Stabilizing vaccinia virus is thus particularly challenging. Attempts to stabilize vaccinia virus have been made. In most cases, a freeze-dried formulation has been proposed (BURKE C J et al. Crit Rev Ther Drug Carrier Syst. 1999, 16(1):1-83). Indeed, while the performance of freeze-drying may induce some loss of viral titer, once freeze-dried, low temperature and absence of movement and interaction between compounds in freeze-dried state make freeze-dried viruses generally more stable than viruses in liquid state. For instance, EP1418942 discloses vaccinia virus formulations for freeze-drying comprising a substantially pure vaccinia virus, a disaccharide, a pharmaceutically acceptable polymer and a buffer that is not a phosphate buffer. WO2014/053571 discloses other freeze-dried MVA formulations comprising polyvinylpyrrolidone (PVP) or derivatives thereof, at least one sugar (in particular sucrose), at least two different amino acids (in particular sodium glutamate and L-arginine), at least two pharmaceutical acceptable salts (in particular NaCl, $Na_2HPO_4$ and $KH_2PO_4$), wherein at least one of said salts is a phosphate salt and, optionally a pharmaceutical acceptable buffer (in particular Tris).

However, freeze-drying is expensive, needs specific equipment and freeze-dried formulations need to be reconstituted before administration. Moreover, freeze-drying involves a freezing step that may lead to some virus aggregation, in particular at high virus titers, which is not suitable for injectable administration. It would thus be very useful to have stable liquid vaccinia virus formulations available.

Previous attempts to stabilize vaccinia virus in the liquid state have not been very successful, since log loss superior to 1 $\log_{10}$ after less than 1 hour at 50° C. were observed in most cases (see BURKE C J et al. Crit Rev Ther Drug Carrier Syst. 1999, 16(1):1-83).

Evans et al disclosed stable liquid adenovirus (non-enveloped DNA virus) formulations buffered between pH 6 and pH 8, comprising a salt (generally NaCl), a sugar (sucrose in most cases), an inhibitor of free radical oxidation (notably EDTA, ethanol or an EDTA/ethanol combination), a non-ionic surfactant and divalent salts (see EVANS et al. J Pharm Sci. 2004 October, 93(10):2458-75; and U.S. Pat. No. 7,456,009). Preferred formulations generally also comprise histidine. Parameters identified as essentials for stability include the presence of an inhibitor of free radical oxidation (in particular EDTA, ethanol, an EDTA/ethanol combination, and/or histidine), and presence of a non-ionic surfactant. The presence of divalent salts is also identified as important for increasing adenovirus stability.

The usefulness of non-ionic surfactants for stabilization purpose has also been documented for papilloma virus (see SHI et al. J Pharm Sci. 2005 July, 94(7):1538-51). US2007/

0161085 tested various liquid formulations for stabilization of influenza virus (enveloped RNA virus). Most stable formulations included arginine and gelatin. In this study, EDTA was shown to have no effect on influenza virus stability. A low amount of surfactant, in addition to arginine and gelatin, was found to be beneficial.

U.S. Pat. No. 7,914,979 relates to formulation for stabilization of enveloped Newcastle disease virus, comprising a non-reducing saccharide such as sucrose. Preferred compositions also contain an amino acid selected from lysine and arginine. In contrast, EDTA is indicated to have a negative effect on stability and is preferably absent from the formulation.

In WO2014/029702, various types of formulations have been tested for stabilization of four canine viruses: two small and medium non-enveloped viruses (canine parvovirus and canine adenovirus type 2) and two enveloped viruses of the paramyxoviruses family (canine distemper virus and canine parainfluenza virus). Results show that enveloped viruses are more difficult to stabilize than non-enveloped viruses, and that the optimal formulation significantly varies between viruses, even for two enveloped viruses of the same paramyxoviruses family (canine distemper virus and canine parainfluenza virus). In addition, it is indicated in Example 1 that while sucrose—in particular at a concentration of 17-25%—and amino acids (such as arginine and methionine), are efficient stabilizers, free radical scavengers (such as EDTA) do not significantly change the stability profile, although they might somewhat contribute to the stability.

The above description of prior art clearly illustrates that designing a stable liquid formulation for a particular virus is a difficult task, since many stabilizers candidates are known in the art and since their stabilizing effect greatly varies depending on the specific virus to be stabilized. In addition, as explained above, due to its enveloped nature, its large size and its DNA genome, vaccinia virus is particularly difficult to stabilize, notably in the liquid state.

SUMMARY OF THE INVENTION

In the context of the present invention, the inventors identified liquid formulations suitable for maintaining stability of vaccinia virus in the liquid state, at about 5° C. (i.e. 5° C.±3° C.) or more. Essential elements of such formulations are the presence of a pharmaceutically acceptable buffer, a monovalent salt, a pharmaceutically acceptable disaccharide or sugar alcohol, a pharmaceutically acceptable chelating agent; and a pH between 6.5 and 8.5. The additional presence of a $C_2$-$C_3$ alcohol further improves stability of the liquid formulations.

In a first aspect, the present invention thus relates to a liquid formulation comprising, consisting essentially of, or consisting of:
 a) a poxvirus, in particular a vaccinia virus,
 b) a pharmaceutically acceptable buffer,
 c) a monovalent salt,
 d) a pharmaceutically acceptable disaccharide or sugar alcohol, and
 e) a pharmaceutically acceptable chelating agent,
wherein the pH of the formulation is comprised between 6.5 and 8.5.

The inventors also surprisingly found that the presence of a chelating agent such as EDTA protects vaccinia virus against UV damage. The present invention thus also relates to the use of a chelating agent for stabilizing a poxvirus, in particular a vaccinia virus against UV damage.

DESCRIPTION OF THE FIGURES

FIG. 5. Beneficial effect of low concentrations of Na glutamate. Infectious losses of MVA-HCV in a control DS formulation containing Tris-HCl 10 mM, sucrose 5% (w/v), Na glutamate 10 mM, NaCl 50 mM, pH 7.5; in a control DS2 formulation containing Tris-HCl 10 mM, sucrose 5% (w/v), Na glutamate 0 mM, NaCl 50 mM, pH 7.5; or in formulations containing Tris-HCl 20 mM, sucrose 10%

Figure 1:
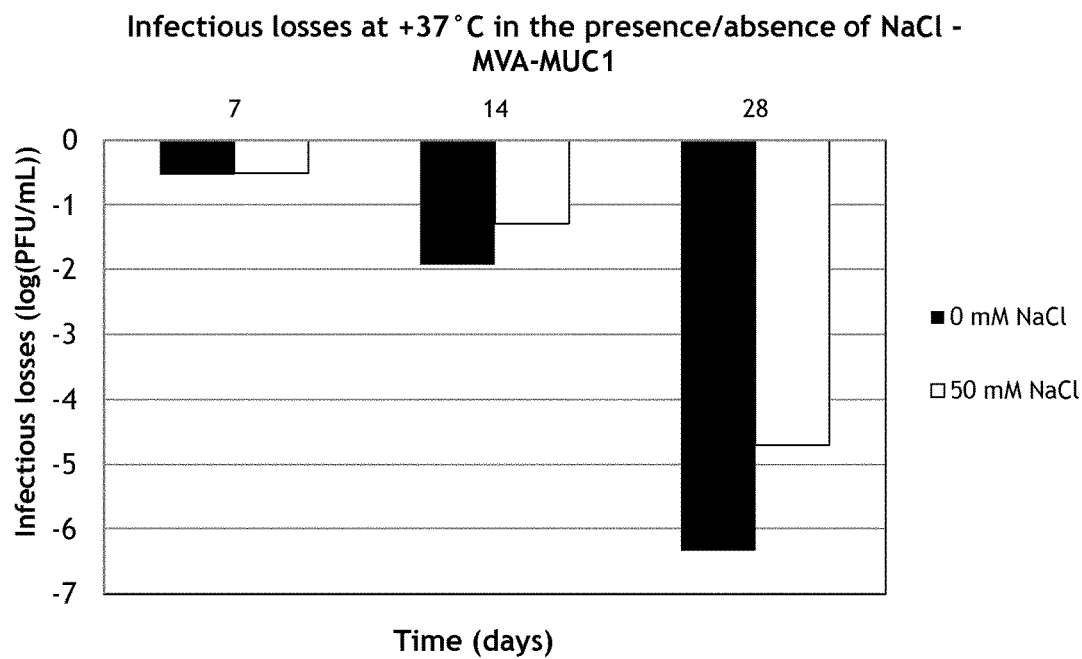
FIG. 1. Beneficial effect of the presence of a monovalent salt. Infectious losses of MVA-MUC1 after 7, 14 or 28 days at +37° C. in a formulation containing Tris-HCl 10 mM, sucrose 5% (w/v), Na glutamate 10 mM, pH 8.0, with 0 mM or 50 mM NaCl. Infectious virus have been measured in particle forming units (PFU)/mL, and infectious losses are expressed in log(PFU/mL).

(w/v), Na glutamate 0 to 10 mM, NaCl 75 mM, EDTA 150 µM, and EtOH 0.5% v/v, pH 7.5 (A) after 7, 14, or 28 days at +37° C.; (B) after 28 days, or 3, 6 or 12 months at +25° C.; (C) after 2, 3, 6, 12, 18, 24 or 30 months at +5° C. Infectious virus have been measured in infectious genomes (IG)/mL, and infectious losses are expressed in log(IG/mL).

FIG. 6. Beneficial effect of sucrose. Infectious losses of MVA-MUC1 in formulations containing Tris-HCl 10 mM, Na glutamate 10 mM, NaCl 50 mM, pH 8.0, and varying amounts of sucrose (1.25; 2.5; 5, 7.5 and 10% (w/v)) after 7 or 14 days at +37° C. Infectious virus have been measured in particle forming units (PFU)/mL, and infectious losses are expressed in log(PFU/mL).

Figure 7A:
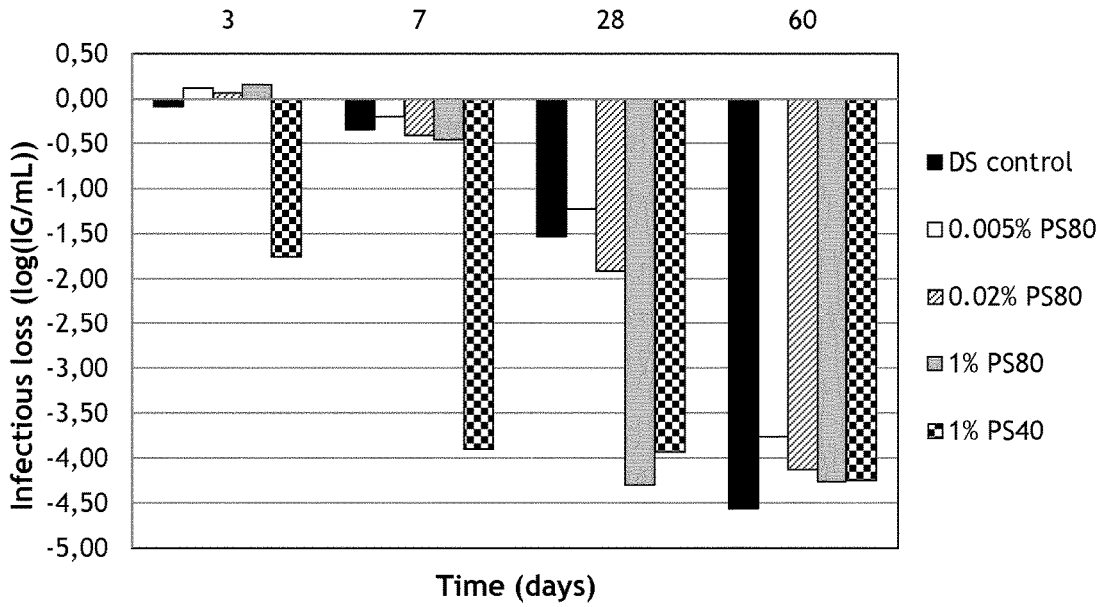
Figure 7B:
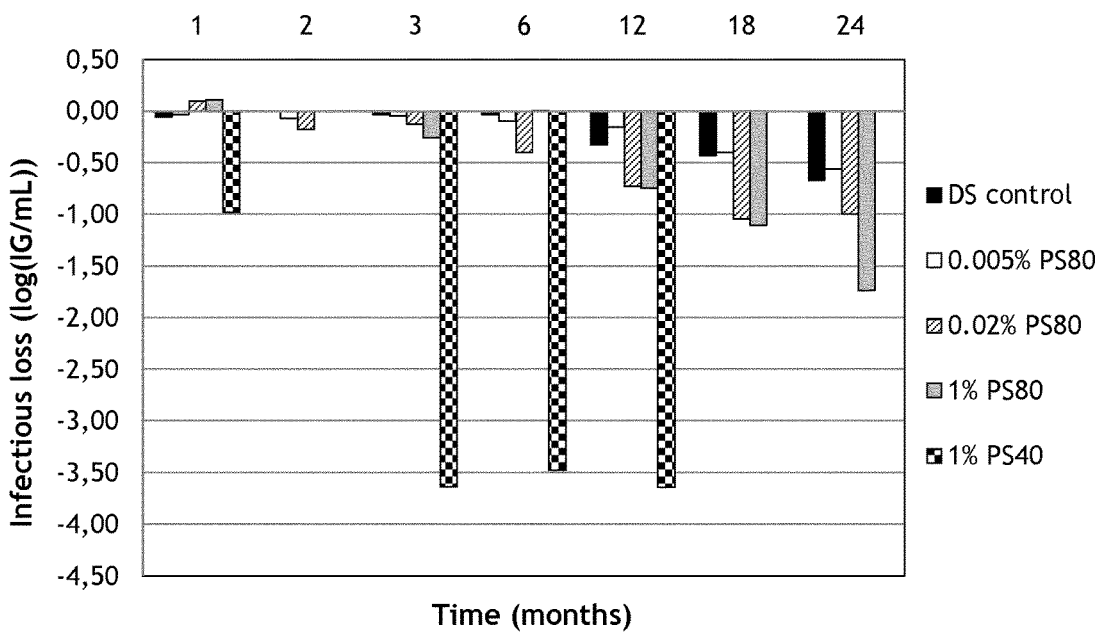
Figure 7C:
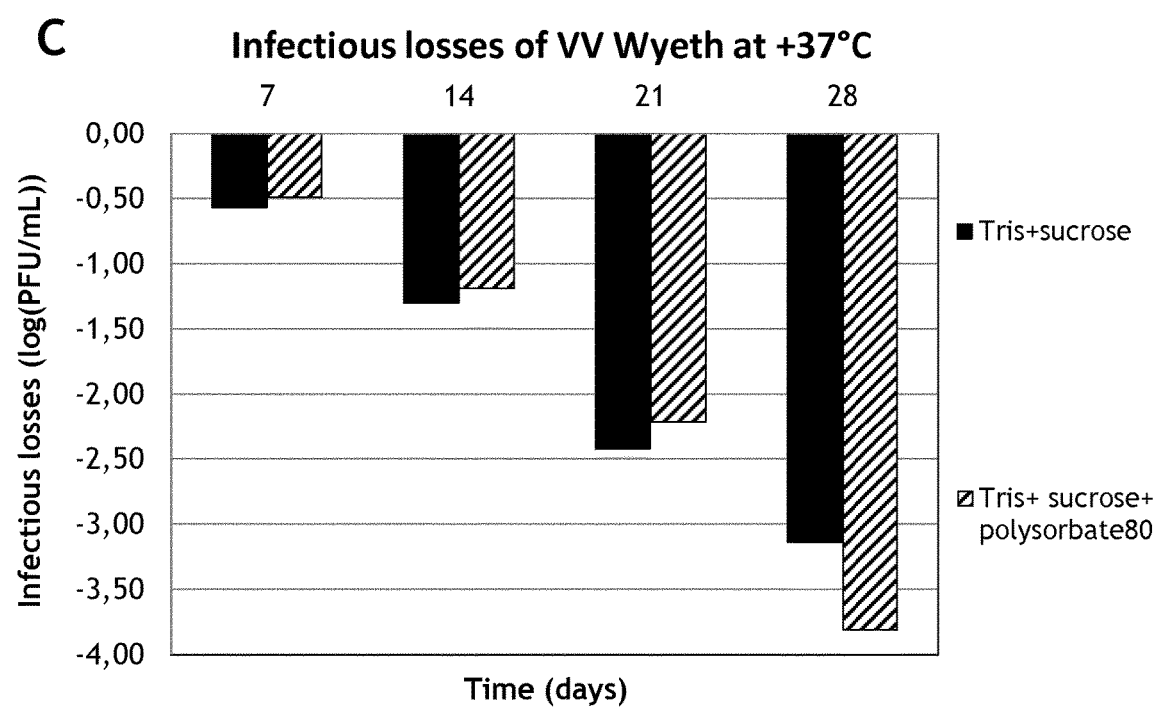

FIG. 7. No beneficial effect and even deleterious effect of polysorbate. (A) and (B) Infectious losses of MVA-HPV in a control DS formulation containing Tris-HCl 10 mM, sucrose 5% (w/v), Na glutamate 10 mM, NaCl 50 mM, pH 7.5; or in formulations containing Tris-HCl 5, 10 or 20 mM, sucrose 5% (w/v), Na glutamate 5 mM, NaCl 50 or 75 mM, pH 7.5, and various concentrations of polysorbate 80 (0.005; 0.02, or 1% v/v) or polysorbate 40 (1% v/v) (A) after 3, 7, 28 or 60 days at +25° C.; or (B) after 1, 2, 3, 6, 12, 18, or 24 months at +5° C. Infectious virus have been measured in infectious genomes (IG)/mL, and infectious losses are expressed in log(IG/mL). (C) Infectious losses of vaccinia virus (VV) Wyeth strain produced in a human continuous cell line and purified by a method that involves at least one step of treatment with at least one protease after 7, 14, 21, or 28 days at +37° C., in a control formulation containing Tris-HCl 30 mM, sucrose 10% (w/v), or in a formulation further containing 150 µg/mL polysorbate 80.

FIG. 8. No beneficial effect of MgCl2 and rather deleterious effect at high concentration. (A) Infectious losses of MVA-MUC1 in formulations containing Tris-HCl 10 mM, sucrose 5% (w/v), Na glutamate 10 mM, NaCl 50 mM, pH 8.0, and varying amounts of $MgCl_2$ (0M; 0.5M; or 1M) after 14 days at +37° C. Infectious virus have been measured in particle forming units (PFU)/mL, and infectious losses are expressed in log(PFU/mL). (B) Infectious losses of vaccinia virus (VV) Wyeth strain produced in a human continuous cell line and purified by a method that involves at least one step of treatment with at least one protease after 7 or 14 days at +37° C., in a control formulation containing Tris-HCl 30 mM, sucrose 10% (w/v), or in a formulation further containing 1000 mM $MgCl_2$.

Figure 9A:
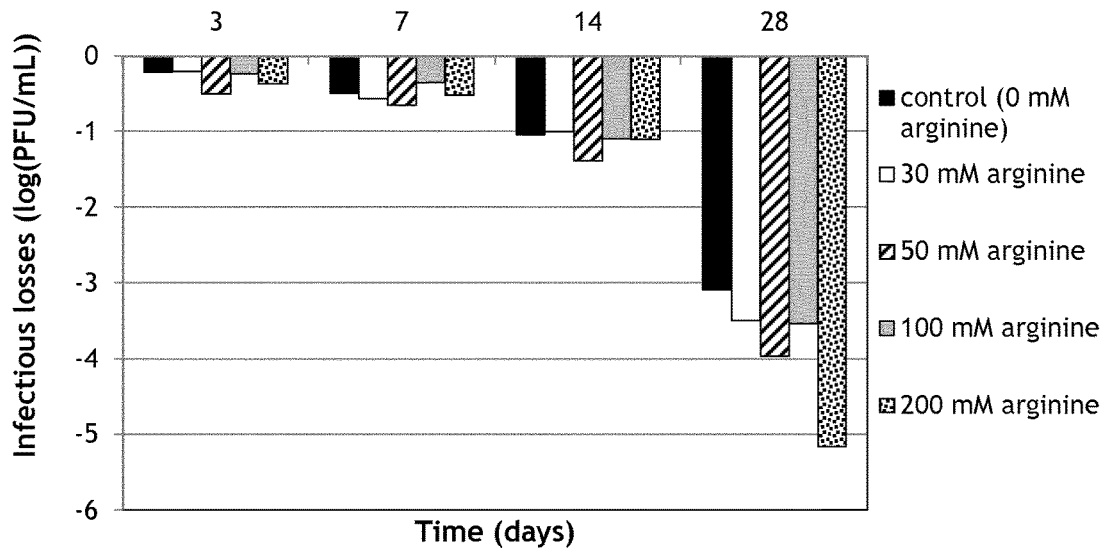
Figure 9B:
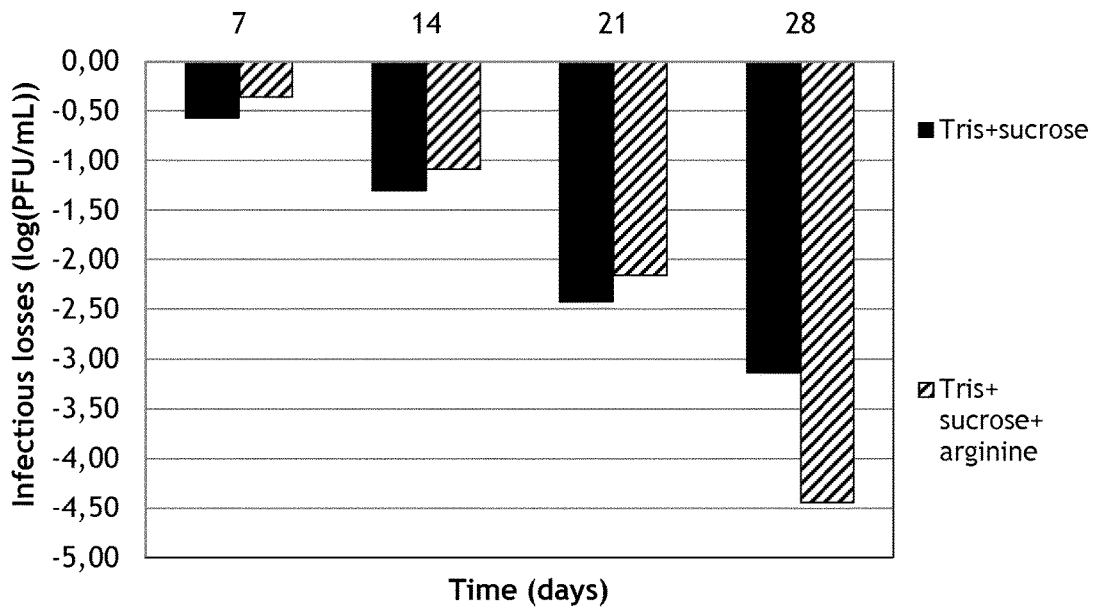

FIG. 9. No beneficial effect and rather deleterious effect of arginine. (A) Infectious losses of MVA-MUC1 in formulations containing Tris-HCl 10 mM, sucrose 5% (w/v), Na glutamate 10 mM, NaCl 50 mM, pH 8.0, and varying amounts of arginine (0, 30, 50, 100 or 200 mM) after 3, 7, 14, or 28 days at +37° C. Infectious virus have been measured in particle forming units (PFU)/mL, and infectious losses are expressed in log(PFU/mL). (B) Infectious losses of vaccinia virus (VV) Wyeth strain produced in a human continuous cell line and purified by a method that involves at least one step of treatment with at least one protease after 7, 14, 21, or 28 days at +37° C., in a control formulation containing Tris-HCl 30 mM, sucrose 10% (w/v), or in a formulation further containing 50 mM arginine.

FIG. 10. No beneficial effect of a mixture of amino acids. Infectious losses of MVA-MUC1 in formulations containing Tris-HCl 10 mM, sucrose 5% (w/v), Na glutamate 10 mM, NaCl 50 mM, pH 8.0, and varying amounts of a mixture of amino acids (0 or 1% (w/v)) after 3, 7, 14, or 28 days at +37° C. Infectious virus have been measured in particle forming units (PFU)/mL, and infectious losses are expressed in log(PFU/mL).

FIG. 11. No beneficial effect of histidine. Infectious losses of MVA-HPV in a control DS formulation containing Tris-HCl 10 mM, sucrose 5% (w/v), Na glutamate 10 mM, NaCl 50 mM, pH 7.5; or in a formulation containing Tris-HCl 20 mM, sucrose 10% (w/v), Na glutamate 5 mM, NaCl 75 mM, and histidine 10 mM, pH 7.5 (A) after 3, 7, 14, 28 or 60 days at +25° C.; or (B) after 1, 2, 3, 6, 12, 18, or 24 months at +5° C. Infectious virus have been measured in infectious genomes (IG)/mL, and infectious losses are expressed in log(IG/mL).

FIG. 12. Effect of pH. Infectious losses of MVA-HCV in formulations containing Tris-HU 20 mM, sucrose 10% (w/v), Na glutamate 5 mM, NaCl 75 mM, EDTA 150 µM and EtOH 0.5% (v/v), with varying pH values (6.0; 7.0; 7.5; 8.0 and 9.0) (A) after 7, 14 or 28 days at +37° C., or (B) after 28 days, or 3, 6 or 12 months at +5° C. Infectious virus have been measured in infectious genomes (IG)/mL, and infectious losses are expressed in log(IG/mL).

FIG. 13. Effect of virus concentration. Infectious losses of MVA-HCV at various initial concentrations (1.0 $10^8$ PFU/mL; 5.0 $10^7$ PFU/mL; 1.0 $10^7$ PFU/mL; or 5.0 $10^6$ PFU/mL) in a control DS formulation containing Tris-HCl 10 mM, sucrose 5% (w/v), Na glutamate 10 mM, NaCl 50 mM, pH 7.5; or in a formulation (Inv) containing Tris-HCl 20 mM, sucrose 10% (w/v), Na glutamate 2.5 mM, NaCl 75 mM, EDTA 150 µM, EtOH 0.5% v/v, pH 7.5 (A) after 7, 14, or 28 days at +37° C.; (B) after 28 days, or 3 or 7 months at +25° C.; or (C) after 2, 6, 12 or 18 months at 5° C. Infectious virus have been measured in infectious genomes (IG)/mL, and infectious losses are expressed in log(IG/mL).

FIG. 14. Validation of the optimized formulation according to the invention on 3 distinct MVA viruses expressing distinct heterologous genes. Infectious losses of MVA-HCV, MVA-MUC1 and MVA-HPV in a control DS formulation containing Tris-HCl 10 mM, sucrose 5% (w/v), Na glutamate 10 mM, NaCl 50 mM, pH 7.5 for MVA-HPV and pH 8.0 for MVA-HCV and MVA-MUC1; or in a formulation containing Tris-HCl 20 mM, sucrose 10% (w/v), Na glutamate 5 mM, NaCl 75 mM, EDTA 150 µM, EtOH 0.5% v/v, pH 7.5 (A) after 7, 14, or 28 days at +37° C.; (B) after 28 days, or 2, 3 or 6 months at +25° C.; or (C) after 2, 3, 6, 12, 18, 24 or 30 months at +5° C. Infectious virus have been measured in infectious genomes (IG)/mL, and infectious losses are expressed in log (IG/mL).

FIG. 15. Validation of an optimized formulation according to the invention on various strains of vaccinia viruses, produced/purified by various methods. (A) Infectious losses of MVA-HCV produced in chicken embryo cells (MVA-HCV/CEC), or in cells of an immortalized avian cell line (MVA-HCV/avian cell line); of MVA-FCU1 produced in chicken embryo cells (MVA-FCU1/CEC) and Copenhagen-FCU1 produced in chicken embryo cells (Copenhagen-FCU1/CEC); in control drug substance (Tris-HCl 10 mM, Na glutamate 10 mM, sucrose 5% (w/v), NaCl 50 mM, pH 7.5) or formulated in an optimized formulation according to the invention (Tris-HCl 20 mM, Na glutamate 5 mM, sucrose 10% (w/v), NaCl 75 mM, EDTA 150 µM, EtOH 0.5%, pH 7.5) after 7, 14, 21, or 28 days at +37° C. (B) Infectious losses of vaccinia virus (VV) Wyeth strain produced in a human continuous cell line and purified by a method that involves at least one step of treatment with at least one protease in control drug substance (Tris-HCl 30 mM, sucrose 10% (w/v), pH 7.5) or formulated in two optimized formulations according to the invention (Tris-HCl 30 mM, sucrose 10% (w/v), NaCl 200 or 500 mM, EDTA 150 µM, EtOH 0.5%, pH 7.5) after 7, 14, 21, or 28 days at +37° C.

FIG. 16. Substitution of initially tested stabilizers by other compounds of the same family or of another family. (A) Infectious losses of MVA-MUC1 in various formulations defined in Table 19 after 7, 14, 21 or 28 days at +37° C. Infectious virus have been measured in infectious genomes (IG)/mL, and infectious losses are expressed in log(IG/mL). (B) and (C) Statistical analysis of the impact of replacing a newly tested candidate equivalent by the initially tested stabilizer or another newly tested candidate equivalent after 14 (B) or 28 (C) days at +37° C., using NemrodW® software. Each line represents a change from a formulation containing candidate equivalent Y to a formulation containing initially tested stabilizer X or another newly tested candidate equivalent (Y=>X), and associated bar and value. When the value is positive, it means that the initially tested stabilizer or the other newly tested candidate X better stabilizes MVA-MUC1 than candidate equivalent Y. In contrast, a negative value means that candidate equivalent Y better stabilizes MVA-MUC1 than the initially tested stabilizer or other candidate equivalent X. The higher is the absolute value, the higher is the effect of replacing Y by X. In particular, it is considered that the replacement has significant impact on MVA-MUC1 stability when the bar exceeds the dashed line. (D) Infectious losses of MVA-MUC1 in various formulations defined in Table 19 after 28, 90 and 180 days at +5° C. Infectious virus have been measured in infectious genomes (IG)/mL, and infectious losses are expressed in log(IG/mL).

FIG. 17. Protection of MVA virus by optimized formulation against UV damage. (A). Infectious losses of MVA-HCV in a control formulation containing Tris-HCl 10 mM, sucrose 5% (w/v), Na glutamate 10 mM, NaCl 50 mM, pH 7.5, or in an optimized formulation containing Tris-HCl 20 mM, sucrose 10% (w/v), Na glutamate 5 mM, NaCl 75 mM, EDTA 150 µM and EtOH 0.5% (v/v), pH 7.5 after 1, 2, 3, 7, 14, 21 or 28 days at +25° C. in the absence of light, under PSM light (simulation of 320-400 nm UV light according to ISO 10977) or under ICH light (ICH Q1B Photostability Testing of New Drug Substances and Products). (B) Infectious losses of MVA-HCV in a control formulation containing Tris-HCl 20 mM, sucrose 10% (w/v), Na glutamate 5 mM, NaCl 75 mM, pH 7.5, or in formulations containing Tris-HCl 20 mM, sucrose 10% (w/v), Na glutamate 5 mM, NaCl 75 mM, and EDTA 150 µM and/or EtOH 0.5% (v/v), pH 7.5 after 2, 3, 7, 9, 14, or 21 days at +25° C. in the absence of light or under ICH light (ICH Q1B Photostability Testing of New Drug Substances and Products). Infectious virus have been measured in infectious genomes (IG)/mL, and infectious losses are expressed in log(IG/mL).

Figure 18:
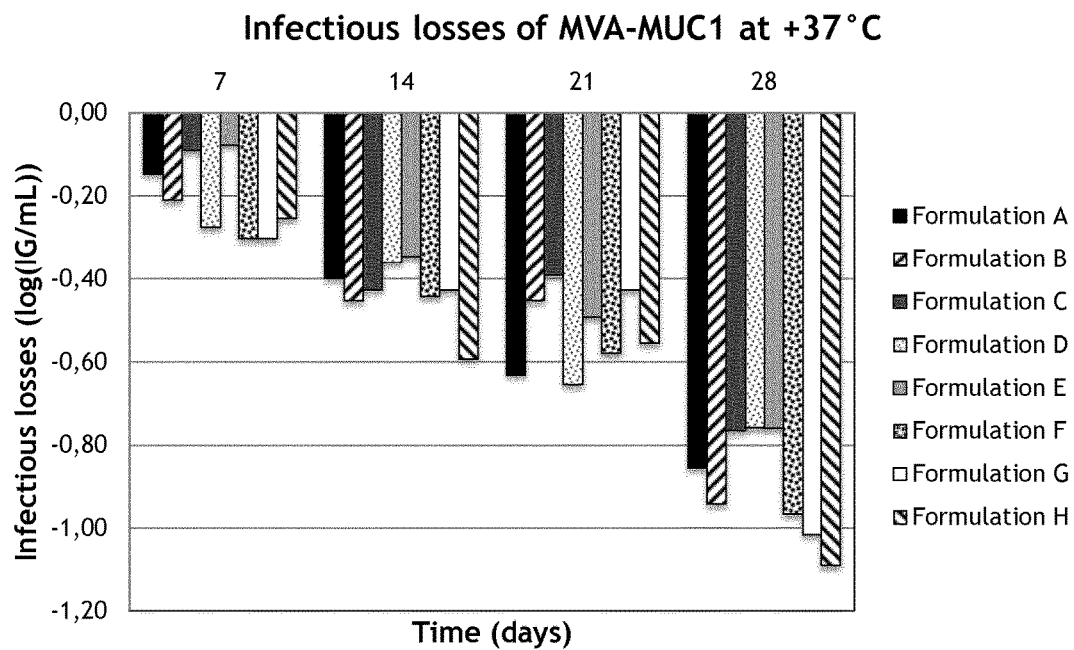

FIG. 18. Stabilizing effect of several formulations with varying concentrations of ingredients. Infectious tosses of MVA-MUC1 in several formulations with varying concentrations of ingredients (see Table 20) after 7, 14, 21, or 28 days at +37° C. Infectious virus have been measured in infectious genomes (IG)/mL, and infectious losses are expressed in log(IG/mL).

Figure 19:
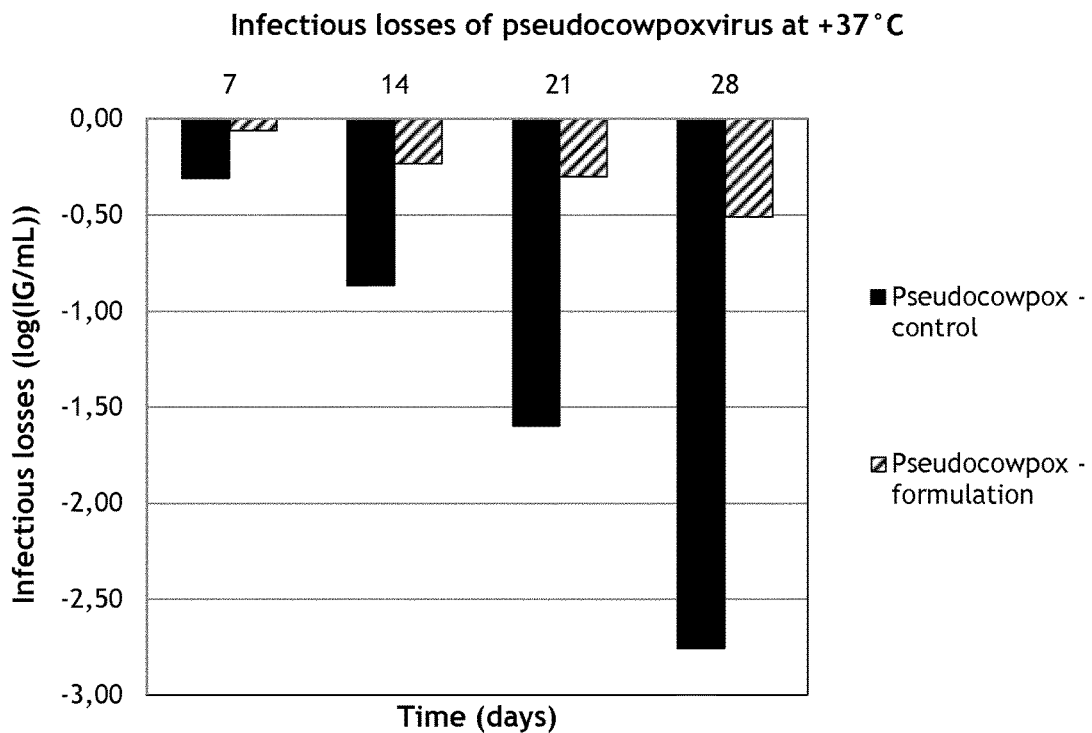

FIG. 19. Stabilizing effect on pseudocowpox virus. Infectious losses of pseudocowpoxvirus in control composition containing Tris-HCl 10 mM, sucrose 5% (w/v), Na glutamate 10 mM, NaCl 50 mM, pH 8.0,) or in a formulation according to the invention containing Tris-HCl 20 mM, sucrose 10% (w/v), Na glutamate 5 mM, NaCl 75 mM, EDTA 150 µM, EtOH 0.5% v/v, pH 7.5 after 7, 14, 21, or 28 days at +37° C. Infectious virus have been measured in infectious genomes (IG)/mL, and infectious losses are expressed in log(IG/mL).

DETAILED DESCRIPTION OF THE INVENTION

Stable Liquid Formulation

As explained above, the inventors identified liquid formulations suitable for maintaining stability of a poxvirus, in particular a vaccinia virus in the liquid state, at about +5° C. or more. Such formulations should comprise a pharmaceutically acceptable buffer, a monovalent salt, a pharmaceutically acceptable disaccharide or sugar alcohol, a pharmaceutically acceptable chelating agent; and a pH between 6.5 and 8.5.

The present invention thus relates to a liquid formulation comprising, consisting essentially of, or consisting of:
 a) a poxvirus, in particular a vaccinia virus,
 b) a pharmaceutically acceptable buffer,
 c) a monovalent salt,
 d) a pharmaceutically acceptable disaccharide or sugar alcohol, and
 e) a pharmaceutically acceptable chelating agent,
wherein the pH of the formulation is comprised between 6.5 and 8.5.

The liquid formulation according to the invention is an aqueous formulation.

"Comprising" and "comprise(s)" are intended to mean that the materials, products, formulations, compositions and methods include the referenced components or steps, but not excluding others. "Consisting essentially of" or "consist(s) essentially of", when used to define products, formulations, compositions and methods, shall mean excluding other components or steps of any essential significance. Thus, for example, a formulation consisting essentially of the recited components would not exclude trace contaminants and pharmaceutically acceptable carriers. "Consisting of" or "consist(s) of" shall mean excluding more than trace elements of other components or steps.

Stability

Formulations according to the invention are liquid, which has the advantage that there is no need for costly and time-consuming freeze-drying processes, and that they may be administered directly, without a need for previous reconstitution.

Stabilization of biological material such as viruses in particular in the liquid state, is not straightforward due to the ability of viruses to interact with all components of the formulation, as well as with the container, which increases risks of viral titer loss. However, the present invention provides virus formulations that are stable in the liquid state and permit to overcome these difficulties. In particular:
 loss of infectious poxvirus, in particular vaccinia virus, titer in liquid formulations according to the invention is preferably less than 1 $\log_{10}$ of infectious virus during storage for at least 1 week, preferably at least 2 weeks, at least 3 weeks, or even at least 4 weeks at +37° C.,
 toss of infectious poxvirus, in particular vaccinia virus, titer in liquid formulations according to the invention is preferably less than 1 $\log_{10}$ of infectious virus during storage for at least 4 weeks, preferably at least 3 months, or at least 6 months at +25° C., and/or
 loss of infectious poxvirus, in particular vaccinia virus, titer in liquid formulations according to the invention is preferably less than 0.3 $\log_{10}$ of infectious virus (which corresponds to a loss of infectivity of 50%) during storage for at least 12 months, preferably at least 18 months, at least 24 months, at least 30 months, or even at least 36 months at about +5° C. (i.e. +5° C.±3° C.).

Infectious vaccinia virus titers at day 0 and at any following date may be determined either by measuring the number of Infectious Genomes (IG) per mL (IG/mL) or by using a plaque assay on BHK-21 cells (infectious poxvirus, in particular vaccinia virus, titer is then expressed in Plaque Forming Units (PFU) per mL (PFU/mL). Measure of the number of infectious genomes per mL (IG/mL) may be preferred, since this method is more rapid and more precise. Detailed protocols for measuring the number of infectious genomes (IG) per mL (IG/mL) or for plaque assay on BKH-21 cells are disclosed in Examples.

Poxvirus

Formulations according to the invention comprise a poxvirus.

Said poxvirus may be selected from the following families: Orthopoxvirus (e.g. vaccinia virus, Cowpox virus), Parapoxvirus (e.g. Bovine papular stomatitis virus, Orf virus, Pseudocowpox virus), Suipoxvirus (e.g. Swinepox virus), Yatapoxvirus (e.g. Yaba-like disease virus), Avipoxvirus (e.g. Fowlpox virus and Canarypoxvirus) and Leporipoxvirux (Myxoma virus). Said poxvirus may particularly be selected from Orthopoxviruses (e.g. vaccinia virus, Cowpox virus) and Parapoxviruses (e.g. Bovine papular stomatitis virus, Orf virus, Pseudocowpox virus). Particularly preferred poxviruses are vaccinia virus and pseudocowpox virus.

In a preferred embodiment, said poxvirus is an Orthopoxvirus, and more preferably a vaccinia virus (VV).

The inventors observed that vaccinia virus stability in the liquid state increases with the concentration of vaccinia virus particles in the formulation (see Example 4). As a result, the poxvirus (in particular vaccinia virus and notably MVA, Wyeth or Copenhagen vaccinia virus) is preferably present in liquid formulations according to the invention at a titer of at least $10^7$ PFU/mL, preferably at least $2 \cdot 10^7$ PFU/mL, at least $3 \cdot 10^7$ PFU/mL, at least $4 \cdot 10^7$ PFU/mL, more preferably at least $5 \cdot 10^7$ PFU/mL, or even at least $10^8$ PFU/mL. Since stability of poxvirus (in particular vaccinia virus) increases with the concentration of poxvirus (in particular vaccinia virus) particles in the formulation, there is no particular restriction concerning the maximal concentration of poxvirus (in particular vaccinia virus) particles in the formulation. However, for practical reasons, poxvirus (in particular vaccinia virus) will generally be comprised in the liquid formulations according to the invention at a titer of at most $10^{12}$ PFU/mL, at most $10^{11}$ PFU/mL, or even at most $10^{10}$ PFU/mL. In particular, poxvirus (in particular vaccinia virus) may be comprised in the liquid formulations according to the invention at a titer of $10^7$ PFU/mL to $10^{12}$ PFU/mL, $10^7$ PFU/mL to $10^{11}$ PFU/mL, $10^7$ PFU/mL to $10^{10}$ PFU/mL, $10^7$ PFU/mL to $5 \cdot 10^9$ PFU/mL, $10^7$ PFU/mL to $10^9$ PFU/mL, $10^7$ PFU/mL to $5 \cdot 10^8$ PFU/mL, $10^7$ PFU/mL to $10^8$ PFU/mL, $2 \cdot 10^7$ PFU/mL to $10^{12}$ PFU/mL, $2 \cdot 10^7$ PFU/mL to $10^{11}$ PFU/mL, $2 \cdot 10^7$ PFU/mL to $10^{10}$ PFU/mL, $2 \cdot 10^7$ PFU/mL to $5 \cdot 10^9$ PFU/mL, $2 \cdot 10^7$ PFU/mL to $10^9$ PFU/mL, $2 \cdot 10^7$ PFU/mL to $5 \cdot 10^8$ PFU/mL, $2 \cdot 10^7$ PFU/mL to $10^8$ PFU/mL, $3 \cdot 10^7$ PFU/mL to $10^{12}$ PFU/mL, $3 \cdot 10^7$ PFU/mL to $10^{11}$ PFU/mL, $3 \cdot 10^7$ PFU/mL to $10^{10}$ PFU/mL, $3 \cdot 10^7$ PFU/mL to $5 \cdot 10^9$ PFU/mL, $3 \cdot 10^7$ PFU/mL to $10^9$ PFU/mL, $3 \cdot 10^7$ PFU/mL to $5 \cdot 10^8$ PFU/mL, $3 \cdot 10^7$ PFU/mL to $10^8$ PFU/mL, $4 \cdot 10^7$ PFU/mL to $10^{12}$ PFU/mL, $4 \cdot 10^7$ PFU/mL to $10^{11}$ PFU/mL, $4 \cdot 10^7$ PFU/mL to $10^{10}$ PFU/mL, $4 \cdot 10^7$ PFU/mL to $5 \cdot 10^9$ PFU/mL, $4 \cdot 10^7$ PFU/mL to $10^9$ PFU/mL, $4 \cdot 10^7$ PFU/mL to $5 \cdot 10^8$ PFU/mL, $4 \cdot 10^7$ PFU/mL to $10^8$ PFU/mL, $5 \cdot 10^7$ PFU/mL to $10^{12}$ PFU/mL, $5 \cdot 10^7$ PFU/mL to $10^{11}$ PFU/mL, $5 \cdot 10^7$ PFU/mL to $10^{10}$ PFU/mL, in particular $5 \cdot 10^7$ PFU/mL to $5 \cdot 10^9$ PFU/mL, $5 \cdot 10^7$ PFU/mL to $10^9$ PFU/mL, $5 \cdot 10^7$ PFU/mL to $5 \cdot 10^8$ PFU/mL, $5 \cdot 10^7$ PFU/mL to $10^8$ PFU/mL, $10^8$ PFU/mL to $10^{12}$ PFU/mL, $10^8$ PFU/mL to $10^{11}$ PFU/mL, $10^8$ PFU/mL to $10^{10}$ PFU/mL, $10^8$ PFU/mL to $5 \cdot 10^9$ PFU/mL, $10^8$ PFU/mL to $10^9$ PFU/mL, $10^8$ PFU/mL to $5 \cdot 10^8$ PFU/mL.

Poxvirus is preferably purified or semi purified to reduce host cell proteins and host cell DNA in order to be well tolerated after human administration. Moreover, a number of impurities could be at the origin of human allergy reaction after injection. Such semi purification or purification processes are conventional in the art and may vary as a function of various parameters such as the virus itself, the producer cell, the culture medium used, the enzymes and other components introduced during production and purification steps (e.g. nucleases, proteases, salts, etc). For example, impurities like egg ovalbumin and antibiotics are typically present when the virus is produced on primary cells like Chicken Embryo Fibrobast (CEF) whereas host cell nucleic acids and proteins are usual contaminants of virus preparation produced on immortalized cell lines such as duck cell lines and human cell lines. For general guidance, it is recommended that host cell DNA be reduced to less than 10 ng/dose (see regulatory specification) and host cell proteins be lower than 150 µg/dose. Representative examples of suitable techniques to achieve semi-purified or purified virus preparation include without limitation tangential flow filtration, enzymatic digestion, chromatography, frontal filtration and the like. Therefore, in a preferred embodiment, the poxvirus (in particular vaccinia virus) is at least semi-purified, comprising 5 to 500 µg/dose of host cell proteins and lower than 10 ng/dose of host cell DNA.

The inventors found that liquid formulations according to the invention are able to stabilize three distinct strains of vaccinia virus: MVA, Wyeth, and Copenhagen (see Example 4). Various strains of vaccinia virus may thus be stabilized using the liquid formulations according to the invention. In particular, said vaccinia virus may be selected from Elstree, Western Reserve, Wyeth, NYVAC, NYCBOH, Paris, Copenhagen, and modified Vaccinia Virus Ankara (MVA) strains. Said vaccinia virus may preferably be selected from modified Vaccinia Virus Ankara (MVA), Wyeth, and Copenhagen strains. In a preferred embodiment, vaccinia virus present in the formulation is a MVA virus, and in particular MVA 575 (ECACC V00120707) or MVA-BN (ECACC V00083008). In another preferred embodiment, vaccinia virus present in the formulation is a Wyeth vaccinia virus. In another preferred embodiment, vaccinia virus present in the formulation is a Copenhagen vaccinia virus.

The poxvirus, in particular vaccinia virus, comprised in the formulations according to the invention may be a wild-type, an attenuated, or a recombinant poxvirus, in particular vaccinia virus. The term "recombinant poxvirus" refers to a poxvirus comprising at least one exogenous sequence inserted in its genome. As used herein, an "exogenous sequence" refers to a nucleic acid which is not naturally present in the parent poxvirus.

When the poxvirus (in particular vaccinia virus) comprised in the formulations according to the invention is recombinant, the exogenous sequence(s) may be any exogenous sequence of interest.

In a first preferred embodiment, the recombinant poxvirus (in particular vaccinia virus) comprises an exogenous sequence encoding a molecule having a directly or indirectly cytotoxic function. By "directly or indirectly" cytotoxic, we mean that the molecule encoded by the exogenous sequence may itself be toxic (for example toxins; cytokines or enzymes such as ribonuclease, deoxyribonuclease) or it may be metabolised to form a toxic product, or it may act on something else to form a toxic product. In a preferred embodiment, the molecule encoded by the exogenous sequence may be a toxin such as ricin or *Pseudomonas* exotoxin A. The sequence of ricin cDNA is disclosed in LAMB et at (Eur. J. Biochem., 1985, 148:265-270). In another preferred embodiment, the molecule encoded by the exogenous sequence may be a cytokine. Such cytokine may notably be selected from tumor necrosis factor (TNF), interleukin-2 (IL-2), interferon-gamma (IFNγ), or granulocyte-macrophage colony-stimulating factor (GMCSF). In another preferred embodiment, the exogenous sequence encoding a molecule having a directly or indirectly cytotoxic function may be a suicide gene. A suicide gene encodes a protein able to convert a relatively non-toxic prodrug to a toxic drug. For example, the enzyme cytosine deaminase converts 5-fluorocytosine (5-FC) to 5-fluorouracil (5-FU) (MULLEN et al., 1922, PNAS 89:33); the herpes simplex enzyme thymidine kinase sensitises cells to treatment with the antiviral agent ganciclovir (GCV) or aciclovir (MOOLTEN, 1986, Cancer Res. 46:5276; EZZEDINE et al., 1991, New Biol 3:608). The cytosine deaminase of any organism, for example *E. coli* or *Saccharomyces cerevisiae*, may be used. Thus, in preferred embodiment of the invention, the suicide gene encodes a protein having a cytosine deaminase activity, and more preferably FCU 1 protein or FCU 1-8 protein disclosed in patent applications WO99/54481, WO2005/007857, WO2009/065546 and WO2009/065547, which are incorporated herein by reference. With this regard, preferred recombinant vaccinia viruses comprised in the liquid formulations according to the invention are:

MVA-FCU 1 (see WO99/54481), also called TG4023;
MVA-FCU 1-8 (see WO2005/007857); and
VV-FCU 1 wherein said vaccinia virus (VV) comprises more particularly a defective I4L and/or F4L gene, and a defective J2R gene (see WO2009/065546 and WO2009/065547).

In a second preferred embodiment, the recombinant vaccinia virus comprises an exogenous gene encoding a ribozyme capable of cleaving targeted RNA or DNA. The targeted RNA or DNA to be cleaved may be RNA or DNA which is essential to the function of the cell and cleavage thereof results in cell death or the RNA or DNA to be cleaved may be RNA or DNA which encodes an undesirable protein, for example an oncogene product, and cleavage of this RNA or DNA may prevent the cell from becoming cancerous.

In a third preferred embodiment, the recombinant poxvirus (in particular vaccinia virus) comprises an exogenous sequence encoding an antisense RNA. By "antisense RNA" we mean an RNA molecule which hybridises to, and interferes with the expression from an mRNA molecule encoding a protein or to another RNA molecule within the cell such as pre-mRNA or tRNA or rRNA, or hybridises to, and interferes with the expression from a gene.

In fourth preferred embodiment, the recombinant poxvirus (in particular vaccinia virus) comprises an exogenous sequence replacing the function of a defective gene in the target cell. There are several thousand inherited genetic diseases of mammals, including humans, which are caused by defective genes. Examples of such genetic diseases include cystic fibrosis, where there is known to be a mutation in the CFTR gene; Duchenne muscular dystrophy, where there is known to be a mutation in the dystrophin gene; sickle cell disease, where there is known to be a mutation in the HbA gene. Many types of cancer are caused by defective genes, especially protooncogenes, and tumor-suppressor genes that have undergone mutation. Examples of protooncogenes are ras, src, bcl and so on; examples of tumor-suppressor genes are p53 and Rb.

In a fifth preferred embodiment, the recombinant poxvirus (in particular vaccinia virus) comprises an exogenous sequence encoding a Tumor Associated Antigen (TAA). TAA refers to a molecule that is detected at a higher frequency or density in tumor cells than in non-tumor cells of the same tissue type. Examples of TAA includes but are not limited to CEA, MART1, MAGE1, MAGE3, GP-100, MUC1 (see WO92/07000, WO95/09241 and ROCHLITZ et al. J Gene Med. 2003 August; 5(8):690-9 incorporated herein by reference), MUC2, pointed mutated ras oncogene, normal or point mutated p53, overexpressed p53, CA-125, PSA, C-erb/B2, BRCA I, BRCA II, PSMA, tyrosinase, TRP1, TRP2, NY-ESO-1, TAG72, KSA, HER-2/neu, bcr-abl, pax3-fkhr, ews-fli-1, surviving and LRP. According to a more preferred embodiment the TAA is MUC1.

In a sixth preferred embodiment, the recombinant poxvirus (in particular vaccinia virus) comprises an exogenous gene encoding an antigen. As used herein, "antigen" refers to a ligand that can be bound by an antibody; an antigen need not itself be immunogenic. Preferably the antigen is derived from:

a virus
 For example, the antigen may be derived from:
  HIV-1, (such as gp 120 or gp 160),
  any of Feline Immunodeficiency virus,
  human or animal herpes viruses, such as gD or derivatives thereof or Immediate Early protein such as ICP27 from HSV1 or HSV2,
  cytomegalovirus (such as gB or derivatives thereof),
  Varicella Zoster Virus (such as gpI, II or III),
  a hepatitis virus such as hepatitis B virus (HBV) for example Hepatitis B Surface antigen or a derivative thereof, hepatitis A virus (HAV), hepatitis C virus (HCV; see WO2004/111082; preferentially nonstructural HCV protein from genotype 1 b strain ja), and hepatitis E virus (HEV),
  Respiratory Syncytial Virus,
  Human Papilloma Virus (HPV; see WO90/10459, WO95/09241, WO98/04705, WO99/03885 and WO2007/121894; E6 and E7 protein from the HPV16 strain are preferred; see also LIU et al., 2004 Oct. 5, Proc Natl Acad Sci USA, 101 Suppl 2:14567-71), or
  Influenza virus.
bacterial pathogens, such as *Salmonella*, *Neisseria*, *Borrelia* (for example OspA or OspB or derivatives thereof), *Chlamydia*, *Bordetella* (for example P.69, PT and FHA), or mycobacteria (in particular *mycobacterium tuberculosis* and *mycobacterium bovis*, see WO2014/009438 and WO2014/009433),
parasites, such as *Plasmodium* or *Toxoplasma*.
According to a more preferred embodiment the antigen is selected from antigens of HCV, HPV, or mycobacteria (in particular *mycobacterium tuberculosis* and *mycobacterium bovis*), and in particular those mentioned above. In this regard, a preferred recombinant vaccinia virus present in the liquid formulations according to the invention is MVA-HCV (see WO2004/111082) also called TG4040 encoding NS3, NS4 and NS5B HCV antigens.

Of course, the recombinant poxvirus (in particular vaccinia virus) present in the liquid formulations according to the invention can comprise more than one exogenous sequence and each exogenous sequence can encode more than one molecule.

For example, it can be useful to associate in a same recombinant poxvirus (in particular vaccinia virus):

an exogenous sequenced encoding e.g. a TAA (as previously described) or an antigen (as previously described), and an exogenous sequence encoding a cytokine (e.g. interleukin (IL as for instance IL-2); tumour necrosis factor (TNF); interferon (IFN); colony stimulating factor (CSF), or granulocyte-macrophage colony-stimulating factor (GMCSF)).

In this respect, preferred recombinant vaccinia viruses present in the liquid formulations according to the invention are:

MVA-[MUC1-IL2] (see WO92/07000 and WO95/09241) also called TG4010 encoding a MUC1 TAA and the human IL-2; and MVA-[HPV-IL2] (see WO90/10459, WO95/09241, WO98/04705, WO99/03885, WO2007/121894) also called TG4001 encoding non oncogenic HPV-16 E6 and E7 polypeptides and the human IL-2.

Another example of useful association of two exogenous sequences in the same poxvirus (in particular vaccinia virus) vector is a poxvirus (in particular vaccinia virus) vector comprising:

An exogenous sequence of interest, including all those described above (in particular a suicide gene, a cytokine, a TAA, or a pathogen antigen), and An exogenous sequence encoding a selection marker. Such selection marker may notably be selected from enzymes that may be easily assayed such as beta-galactosidase, green fluorescent protein and luciferase.

In this respect, a preferred recombinant vaccinia virus present in the liquid formulations according to the invention is a vaccinia virus (preferably Wyeth strain) defective for J2R gene, and comprising an exogenous sequence encoding granulocyte-macrophage colony-stimulating factor (GM-CSF) (see KIM J H et al., 2006 September, Mol Ther., 14(3):361-70 and BREITBACH C J et al., 2011, Curr Pharm Biotechnol. Vol 12. No 12).

Methods for preparing and purifying poxviruses and in particular vaccinia virus are known to those skilled in the art. For instance, processes for producing and purifying poxviruses and in particular vaccinia viruses are disclosed in WO2007/147528 and WO2010/130753, which are herein incorporated by reference.

Vaccinia virus may notably be firstly amplified by:
a) preparing a culture of packaging cells;
b) infecting the packaging cell culture with a vaccinia virus;
c) culturing the infected packaging cells until progeny vaccinia virus is produced, and
d) collecting produced vaccinia virus from the culture supernatant and/or the packaging cells.

In step a), suitable packaging cells depend on the type of vaccinia virus to be amplified.

MVA is strictly host-restricted and may be amplified on avian cells, either primary avian cells (such as chicken embryo fibroblasts or CEF) or an immortalized avian cell line, and in particular:

a *Cairina moschata* immortalized avian cell line comprising a nucleic acid sequence coding a telomerase reverse transcriptase (TERT) (see cell tines T3-17490 as deposited at the European Collection of Celt Cultures (ECACC) under accession number 08060502 and cell line T6-17490 as deposited at ECACC under accession number 08060501 disclosed in WO2007/077256), a *Cairina moschata* immortalized avian cell line comprising an E1A nucleic acid sequence and a nucleic acid sequence coding a telomerase reverse transcriptase (TERT), as disclosed in WO2009/004016, DF1 cell line disclosed in U.S. Pat. No. 5,879,924, which is a spontaneously immortalized chicken cell line derived from 10 day old East Lansing Line (ELL-O) eggs, Ebx chicken cell line disclosed in WO2005/007840, which derives from embryonic stem cells by progressive severance from growth factors and feeder layer; or DEC 99 cell line (IVANOV et al. Experimental Pathology and Parasitology, 4/2000 Bulgarian Academy of Sciences), which is duck embryo permanent cell line.

For other vaccinia virus or other poxvirus strains, in addition to avian primary cells (such as CEF—"chicken embryo fibroblasts"—also called CEC or "chicken embryo cells") and avian cell lines, many other non-avian cell lines are available for amplification, including Hela, BHK-21, MRC-5, HEK-293, and Vero cells. In a preferred embodiment, vaccinia virus other than MVA is amplified in Hela cells.

Packaging cells are preferably cultivated in a medium free from animal- or human-derived products, using a chemically defined medium with no product of animal or human origin. In particular, while growth factors may be present, they are preferably recombinantly produced and not purified from animal material. An appropriate animal-free medium may be easily selected by those skilled in the art depending on selected packaging cells. Such media are commercially available. In particular, when CEFs are used as packaging cells, they may be cultivated in VP-SFM cell culture medium (Invitrogen). CEFs are also preferably cultivated for between 1 and 5 days, more preferably between 1 and 2 days and even more preferably 2 days before infection. CEFs are further preferably cultivated at a temperature comprised between +30° C. and +37° C. When non-avian immortalized cell tines cells are used, they are preferably cultivated for between 2 and 7 days before infection. If a high number of non-avian immortalized cells is needed, several passages of 2 to 7 days may be made in order to increase the total number of cells. Non-avian immortalized cells are further preferably cultivated at a temperature comprised between +36° C. and +38° C., more preferably at about +37° C.

In step b), packaging cells are infected by poxvirus (in particular vaccinia virus) under appropriate conditions (in particular using an appropriate multiplicity of infection (MOI)) to permit productive infection of packaging cells. In particular, when vaccinia virus is MVA (in particular those disclosed in WO90/10459, WO92/07000, WO95/09241, WO98/04705, WO99/03885, WO2004/111082, WO2007/121894, WO2014/009438 and WO2014/009433) and is amplified using CEF, it may be seeded in the cell culture vessel containing CEFs at a MOI which is preferably comprised between 0.001 and 0.1, more preferably between 0.03 and 0.07 and even more preferably about 0.05. For other vaccinia virus strains, in particular oncolytic vaccinia virus such as Wyeth and Copenhagen strains (notably those disclosed in WO2007/030668, WO2008/113078, WO2009/065546, WO2009/065547), vaccinia virus may be seeded in the cell culture vessel containing packaging cells at a MOI which is preferably comprised between 0.0001 and 0.1, and more preferably about 0.0001. Infection step is also preferably performed in a medium (which may be the same as or different from the medium used for culture of packaging cells) free from animal- or human-derived products, using a chemically defined medium with no product of animal or human origin. For MVA in CEFs, the culture medium used in step b) is preferably a basal medium, notably Basal Medium Eagle cell culture medium (Invitrogen).

In step c), infected packaging cells are then cultured under appropriate conditions well known to those skilled in the art until progeny poxvirus (in particular vaccinia virus) is produced. Culture of infected packaging cells is also preferably performed in a medium (which may be the same as or different from the medium used for culture of packaging cells and/or for infection step) free from animal- or human-derived products, using a chemically defined medium with no product of animal or human origin. For MVA amplified on CEFs, CEFs may notably be cultured in basal medium, notably Basal Medium Eagle cell culture medium (Invitrogen), at a temperature between +33° C. and +37° C., during 1 to 4 days. For other vaccinia virus strains produced in a non-avian immortalized cell line, step c) may notably be performed between +35° C. and +38° C. during 1 to 4 days.

In step d), poxvirus (in particular vaccinia virus) produced in step c) is collected from the culture supernatant and/or the packaging cells. When poxvirus (in particular vaccinia virus) is collected from packaging cells (and optionally also from culture supernatant), step d) may be preceded by a step allowing the disruption of the packaging cell membrane. This step leads to the liberation of poxvirus (in particular vaccinia virus) from packaging cells. The disruption of packaging cells membrane can be induced by various techniques well known to those skilled in the art, including but not limited to: freeze/thaw, hypotonic lysis, sonication, microfluidization, or high speed homogenization.

Poxvirus (in particular vaccinia virus) may then be further purified, using purification steps well known in the art, such as:

Treatment with at least one nuclease in order to remove packaging cells DNA,

Treatment with at least one protease in order to remove packaging cells proteins, Separation of poxvirus (in particular vaccinia virus) from contaminants using ultracentrifugation (in particular through a cesium chloride gradient), filtration (in particular depth filtration) or chromatography (in particular ion exchange chromatography).

In a preferred embodiment of the present invention, vaccinia virus present in the formulation is a MVA virus (in particular those disclosed in WO90/10459, WO92/07000, WO95/09241, WO98/04705, WO99/03885, WO2004/111082, WO2007/121894, WO2014/009438 and WO2014/009433) amplified on CEFs, more preferably a MVA virus (in particular those disclosed in WO90/10459, WO92/07000, WO95/09241, WO98/04705, WO99/03885, WO2004/111082, WO2007/121894, WO2014/009438 and WO2014/009433) amplified on CEFs and which has not been submitted to a step of treatment with at least one protease.

In another preferred embodiment, vaccinia virus present in the formulation is a MVA virus (in particular those disclosed in WO90/10459, WO92/07000, WO95/09241, WO98/04705, WO99/03885, WO2004/111082, WO2007/121894, WO2014/009438 and WO2014/009433) amplified on an immortalized avian cell line (including a *Cairina moschata* immortalized avian cell line comprising a nucleic acid sequence coding a telomerase reverse transcriptase (TERT), a *Cairina moschata* immortalized avian cell line comprising an E1A nucleic acid sequence and a nucleic acid sequence coding a telomerase reverse transcriptase (TERT), a DF1 cell line, an Ebx cell line, or a DEC 99 cell line), more preferably a MVA virus (in particular those disclosed in WO90/10459, WO92/07000, WO95/09241, WO98/04705, WO99/03885, WO2007/111082, WO2007/121894, WO2014/009438 and WO2014/009433) amplified on an immortalized avian cell line (including those mentioned above) that has not been subjected to at least one step of treatment with at least one protease.

In another preferred embodiment, vaccinia virus present in the formulation is a Wyeth or Copenhagen vaccinia virus (in particular those disclosed in WO2007/030668, WO2008/113078, WO2009/065546, WO2009/065547) amplified in Hela cells, more preferably a Wyeth or Copenhagen vaccinia virus (in particular those disclosed in WO2007/030668, WO2008/113078, WO2009/065546, WO2009/065547) amplified in Hela cells that has been subjected to at least one step of treatment with at least one protease.

pH and Buffer

Liquid formulations according to the invention have a pH comprised between 6.5 and 8.5. In particular, liquid formulations according to the invention may have a pH comprised between 6.5 and 8.4, between 6.5 and 8.3, between 6.5 and 8.2, between 6.5 and 8.1, between 6.5 and 8.0, between 6.5 and 7.9, between 6.5 and 7.8, between 6.5 and 7.7, between 6.5 and 7.6, between 6.5 and 7.5, between 6.6 and 8.5, between 6.6 and 8.4, between 6.6 and 8.3, between 6.6 and 8.2, between 6.6 and 8.1, between 6.6 and 8.0, between 6.6 and 7.9, between 6.6 and 7.8, between 6.6 and 7.7, between 6.6 and 7.6, between 6.6 and 7.5, between 6.7 and 8.5, between 6.7 and 8.4, between 6.7 and 8.3, between 6.7 and 8.2, between 6.7 and 8.1, between 6.7 and 8.0, between 6.7 and 7.9, between 6.7 and 7.8, between 6.7 and 7.7, between 6.7 and 7.6, between 6.7 and 7.5, between 6.8 and 8.5, between 6.8 and 8.4, between 6.8 and 8.3, between 6.8 and 8.2, between 6.8 and 8.1, between 6.8 and 8.0, between 6.8 and 7.9, between 6.8 and 7.8, between 6.8 and 7.7, between 6.8 and 7.6, between 6.8 and 7.5, between 6.9 and 8.5, between 6.9 and 8.4, between 6.9 and 8.3, between 6.9 and 8.2, between 6.9 and 8.1, between 6.9 and 8.0, between 6.9 and 7.9, between 6.9 and 7.8, between 6.9 and 7.7, between 6.9 and 7.6, between 6.9 and 7.5, between 7 and 8.5, between 7 and 8.4, between 7 and 8.3, between 7 and 8.2, between 7 and 8.1, between 7 and 8, between 7 and 7.9, between 7 and 7.8, between 7 and 7.7, between 7 and 7.6, between 7 and 7.5, between 7.1 and 8.5, between 7.1 and 8.4, between 7.1 and 8.3, between 7.1 and 8.2, between 7.1 and 8.1, between 7.1 and 8, between 7.1 and 7.9, between 7.1 and 7.8, between 7.1 and 7.7, between 7.1 and 7.6, between 7.1 and 7.5, between 7.2 and 8.5, between 7.2 and 8.4, between 7.2 and 8.3, between 7.2 and 8.2, between 7.2 and 8.1, between 7.2 and 8, between 7.2 and 7.9, between 7.2 and 7.8, between 7.2 and 7.7, between 7.2 and 7.6, between 7.2 and 7.5, between 7.3 and 8.5, between 7.3 and 8.4, between 7.3 and 8.3, between 7.3 and 8.2, between 7.3 and 8.1, between 7.3 and 8, between 7.3 and 7.9, between 7.3 and 7.8, between 7.3 and 7.7, between 7.3 and 7.6, between 7.3 and 7.5, between 7.4 and 8.5, between 7.4 and 8.4, between 7.4 and 8.3, between 7.4 and 8.2, between 7.4 and 8.1, between 7.4 and 8, between 7.4 and 7.9, between 7.4 and 7.8, between 7.4 and 7.7, between 7.4 and 7.6, between 7.4 and 7.5, between 7.5 and 8.5, between 7.5 and 8.4, between 7.5 and 8.3, between 7.5 and 8.2, between 7.5 and 8.1, between 7.5 and 8, between 7.5 and 7.9, between 7.5 and 7.8, between 7.5 and 7.7, or between 7.5 and 7.6. Preferably, liquid formulations according to the invention have a pH between 7 and 8, and more particularly close to 7.5, in particular comprised between 7.2 and 7.8, between 7.3 and 7.7, between 7.4 and 7.6, or about 7.5.

In order to maintain this pH, the liquid formulations according to the invention comprise a buffer with buffering capacity at the pH of the formulation. Such buffers are well known to those skilled in the art, and notably include the following buffers:

TRIS-HCl (tris(hydroxymethyl)methylamine-HCl),
TRIS (tris(hydroxymethyl)methylamine),
HEPES (4-2-hydroxyethyl-1-piperazineethanesulfonic acid),
Phosphate buffer comprising a mixture of $Na_2HPO_4$ and $KH_2PO_4$ or a mixture of $Na_2HPO_4$ and $NaH_2PO_4$,
ACES (N-(2-Acetamido)-aminoethanesulfonic acid),
PIPES (Piperazine-N,N'-bis(2-ethanesulfonic acid)),
MOPSO (3-(N-Morpholino)-2-hydroxypropanesulfonic acid),
BIS-Tris-Propane (1,3-Bis[tris(hydroxymethyl)-methylamino]propane),
BES (N,N-bis(2-hydroxyethyl) 2-aminoethane sulphonic acid)
MOPS (3-(N-morpholino)propanesulfonic acid),
TES (2-{[tris(hydroxymethyl)methyl]amino}ethanesulfonic acid),
DIPSO (3-[bis(2-hydroxyethyl)amino]-2-hydroxypropane-1-sulfonic acid),
MOBS (4-(N-morpholino)butanesulfonic acid),
TAPSO (3-[N-Tris(hydroxymethyl)methylamino]-2-hydroxypropanesulfonic Acid),
HEPPSO (4-(2-Hydroxyethyl)-piperazine-1-(2-hydroxy)-propanesulfonic acid),
POPSO (2-hydroxy-3-[4-(2-hydroxy-3-sulfopropyl)piperazin-1-yl]propane-1-sulfonic acid),
TEA (triethanolamine),
EPPS (N-(2-Hydroxyethyl)-piperazine-N'-3-propanesulfonic acid), and
TRICINE (N-[Tris(hydroxymethyl)-methyl]-glycine).

Preferably, said buffer is selected from TRIS-HCl, TRIS, Tricine, HEPES and phosphate buffer comprising a mixture of $Na_2HPO_4$ and $KH_2PO_4$ or a mixture of $Na_2HPO_4$ and $NaH_2PO_4$. More preferably said buffer is selected from TRIS-HCl, TRIS, or Tricine buffer, and more preferably said buffer is TRIS-HCl or TRIS buffer, even more preferably said buffer is TRIS-HCl buffer.

Said buffer (in particular those mentioned above and notably TRIS-HCl) is preferably present in a concentration of 10 to 50 mM. It may notably be present in a concentration of 10 to 45 mM, 10 to 40 mM, 10 to 35 mM, 10 to 30 mM, 10 to 25 mM, 10 to 20 mM, 10 to 15 mM, 15 to 50 mM, 15 to 45 mM, 15 to 40 mM, 15 to 35 mM, 15 to 30 mM, 15 to 25 mM, 15 to 20 mM, 20 to 50 mM, 20 to 45 mM, 20 to 40 mM, 20 to 35 mM, 20 to 30 mM, 20 to 25 mM, 25 to 50 mM, 25 to 45 mM, 25 to 40 mM, 25 to 35 mM, 25 to 30 mM, 30 to 50 mM, 30 to 45 mM, 30 to 40 mM, 30 to 35 mM, 35 to 50 mM, 35 to 45 mM, 35 to 40 mM, 40 to 50 mM, 40 to 45 mM, or 45 to 50 mM. Preferably, said buffer (in particular those mentioned above and notably TRIS-HCl) is preferably present in a concentration of 10 to 40 mM, in particular of 10 to 30 mM.

Monovalent Salt

Liquid formulations according to the invention comprise a monovalent salt. This monovalent salt is believed to ensure an appropriate osmotic pressure. In addition, said monovalent salt is also believed to have inhibition properties of proteases that may be present in the formulation, thus improving stability. Such proteases include cell proteases liberated when disrupting packaging cells and also, when the vaccinia virus present in the formulation has been purified by a method involving the use of protease, remaining traces of said added protease. The inhibiting effect of significant monovalent salts concentration on proteases has been documented in the art (see TÕUGU V et al. Eur J Biochem. 1994 June, 222(2):475-81). For instance, for Pierce Trypsin Protease (Thermo Scientific), the manufacturer indicates in the Instruction notice that high monovalent salt concentrations, such as >100 mM NaCl, may interfere with trypsin activity.

Said monovalent salt may notably be selected from NaCl and KCl, preferably said monovalent salt is NaCl.

Said monovalent salt (in particular NaCl) is preferably present in a concentration of 10 to 1000 mM. It may notably be present in a concentration of 10 to 950 mM, 10 to 900 mM, 10 to 850 mM, 10 to 800 mM, 10 to 750 mM, 10 to 700 mM, 10 to 650 mM, 10 to 600 mM, 10 to 550 mM, 10 to 500 mM, 10 to 450 mM, 10 to 400 mM, 10 to 350 mM, 10 to 300 mM, 10 to 250 mM, 10 to 200 mM, 10 to 150 mM, 10 to 100 mM, 10 to 90 mM, 10 to 80 mM, 10 to 75 mM, 10 to 70 mM, 10 to 60 mM, 10 to 50 mM, 10 to 40 mM, 10 to 30 mM, 10 to 25 mM, 10 to 20 mM, 20 to 1000 mM, 20 to 950 mM, 20 to 900 mM, 20 to 850 mM, 20 to 800 mM, 20 to 750 mM, 20 to 700 mM, 20 to 650 mM, 20 to 600 mM, 20 to 550 mM, 20 to 500 mM, 20 to 450 mM, 20 to 400 mM, 20 to 350 mM, 20 to 300 mM, 20 to 250 mM, 20 to 200 mM, 20 to 150 mM, 20 to 100 mM, 20 to 90 mM, 20 to 80 mM, 20 to 75 mM, 20 to 70 mM, 20 to 60 mM, 20 to 50 mM, 20 to 40 mM, 20 to 30 mM, 20 to 25 mM, 25 to 1000 mM, 25 to 950 mM, 25 to 900 mM, 25 to 850 mM, 25 to 800 mM, 25 to 750 mM, 25 to 700 mM, 25 to 650 mM, 25 to 600 mM, 25 to 550 mM, 25 to 500 mM, 25 to 450 mM, 25 to 400 mM, 25 to 350 mM, 25 to 300 mM, 25 to 250 mM, 25 to 200 mM, 25 to 150 mM, 25 to 100 mM, 25 to 90 mM, 25 to 80 mM, 25 to 75 mM, 25 to 70 mM, 25 to 60 mM, 25 to 50 mM, 25 to 40 mM, 25 to 30 mM, 30 to 1000 mM, 30 to 950 mM, 30 to 900 mM, 30 to 850 mM, 30 to 800 mM, 30 to 750 mM, 30 to 700 mM, 30 to 650 mM, 30 to 600 mM, 30 to 550 mM, 30 to 500 mM, 30 to 450 mM, 30 to 400 mM, 30 to 350 mM, 30 to 300 mM, 30 to 250 mM, 30 to 200 mM, 30 to 150 mM, 30 to 100 mM, 30 to 90 mM, 30 to 80 mM, 30 to 75 mM, 30 to 70 mM, 30 to 60 mM, 30 to 50 mM, 30 to 40 mM, 40 to 1000 mM, 40 to 950 mM, 40 to 900 mM, 40 to 850 mM, 40 to 800 mM, 40 to 750 mM, 40 to 700 mM, 40 to 650 mM, 40 to 600 mM, 40 to 550 mM, 40 to 500 mM, 40 to 450 mM, 40 to 400 mM, 40 to 350 mM, 40 to 300 mM, 40 to 250 mM, 40 to 200 mM, 40 to 150 mM, 40 to 100 mM, 40 to 90 mM, 40 to 80 mM, 40 to 75 mM, 40 to 70 mM, 40 to 60 mM, 40 to 50 mM, 50 to 1000 mM, 50 to 950 mM, 50 to 900 mM, 50 to 850 mM, 50 to 800 mM, 50 to 750 mM, 50 to 700 mM, 50 to 650 mM, 50 to 600 mM, 50 to 550 mM, 50 to 500 mM, 50 to 450 mM, 50 to 400 mM, 50 to 350 mM, 50 to 300 mM, 50 to 250 mM, 50 to 200 mM, 50 to 150 mM, 50 to 100 mM, 50 to 90 mM, 50 to 80 mM, 50 to 75 mM, 50 to 70 mM, 50 to 60 mM, 60 to 1000 mM, 60 to 950 mM, 60 to 900 mM, 60 to 850 mM, 60 to 800 mM, 60 to 750 mM, 60 to 700 mM, 60 to 650 mM, 60 to 600 mM, 60 to 550 mM, 60 to 500 mM, 60 to 450 mM, 60 to 400 mM, 60 to 350 mM, 60 to 300 mM, 60 to 250 mM, 60 to 200 mM, 60 to 150 mM, 60 to 100 mM, 60 to 90 mM, 60 to 80 mM, 60 to 75 mM, 60 to 70 mM, 70 to 1000 mM, 70 to 950 mM, 70 to 900 mM, 70 to 850 mM, 70 to 800 mM, 70 to 750 mM, 70 to 700 mM, 70 to 650 mM, 70 to 600 mM, 70 to 550 mM, 70 to 500 mM, 70 to 450 mM, 70 to 400 mM, 70 to 350 mM, 70 to 300 mM, 70 to 250 mM, 70 to 200 mM, 70 to 150 mM, 70 to 100 mM, 70 to 90 mM, 70 to 80 mM, 70 to 75 mM, 75 to 1000 mM, 75 to 950 mM, 75 to 900 mM, 75 to 850 mM, 75 to 800 mM, 75 to 750 mM, 75 to 700 mM, 75 to 650 mM, 75 to 600 mM, 75 to 550 mM, 75 to 500 mM, 75 to 450 mM, 75 to 400 mM, 75 to 350 mM, 75 to 300 mM, 75 to 250 mM, 75 to 200 mM, 75 to 150 mM, 75 to 100 mM, 75 to 90 mM, 75 to 80 mM, 80 to 1000 mM, 80 to 950 mM, 80 to 900 mM, 80 to 850 mM, 80 to 800 mM, 80 to 750 mM, 80 to 700 mM, 80 to 650 mM, 80 to 600 mM, 80 to 550 mM, 80 to 500 mM, 80 to 450 mM, 80 to 400 mM, 80 to 350 mM, 80 to 300 mM, 80 to 250 mM, 80 to 200 mM, 80 to 150 mM, 80 to 100 mM, 80 to 90 mM, 90 to 1000 mM, 90 to 950 mM, 90 to 900 mM, 90 to 850 mM, 90 to 800 mM, 90 to 750 mM, 90 to 700 mM, 90 to 650 mM, 90 to 600 mM, 90 to 550 mM, 90 to 500 mM, 90 to 450 mM, 90 to 400 mM, 90 to 350 mM, 90 to 300 mM, 90 to 250 mM, 90 to 200 mM, 90 to 150 mM, 90 to 100 mM, 100 to 1000 mM, 100 to 950 mM, 100 to 900 mM, 100 to 850 mM, 100 to 800 mM, 100 to 750 mM, 100 to 700 mM, 100 to 650 mM, 100 to 600 mM, 100 to 550 mM, 100 to 500 mM, 100 to 450 mM, 100 to 400 mM, 100 to 350 mM, 100 to 300 mM, 100 to 250 mM, 100 to 200 mM, 100 to 150 mM, 150 to 1000 mM, 150 to 950 mM, 150 to 900 mM, 150 to 850 mM, 150 to 800 mM, 150 to 750 mM, 150 to 700 mM, 150 to 650 mM, 150 to 600 mM, 150 to 550 mM, 150 to 500 mM, 150 to 450 mM, 150 to 400 mM, 150 to 350 mM, 150 to 300 mM, 150 to 250 mM, 150 to 200, 200 to 1000 mM, 200 to 950 mM, 200 to 900 mM, 200 to 850 mM, 200 to 800 mM, 200 to 750 mM, 200 to 700 mM, 200 to 650 mM, 200 to 600 mM, 200 to 550 mM, 200 to 500 mM, 200 to 450 mM, 200 to 400 mM, 200 to 350 mM, 200 to 300 mM, 200 to 250 mM, 250 to 1000 mM, 250 to 950 mM, 250 to 900 mM, 250 to 850 mM, 250 to 800 mM, 250 to 750 mM, 250 to 700 mM, 250 to 650 mM, 250 to 600 mM, 250 to 550 mM, 250 to 500 mM, 250 to 450 mM, 250 to 400 mM, 250 to 350 mM, 250 to 300 mM, 300 to 1000 mM, 300 to 950 mM, 300 to 900 mM, 300 to 850 mM, 300 to 800 mM, 300 to 750 mM, 300 to 700 mM, 300 to 650 mM, 300 to 600 mM, 300 to 550 mM, 300 to 500 mM, 300 to 450 mM, 300 to 400 mM, 300 to 350 mM, 350 to 1000 mM, 350 to 950 mM, 350 to 900 mM, 350 to 850 mM, 350 to 800 mM, 350 to 750 mM, 350 to 700 mM, 350 to 650 mM, 350 to 600 mM, 350 to 550 mM, 350 to 500 mM, 350 to 450 mM, 350 to 400 mM, 400 to 1000 mM, 400 to 950 mM, 400 to 900 mM, 400 to 850 mM, 400 to 800 mM, 400 to 750 mM, 400 to 700 mM, 400 to 650 mM, 400 to 600 mM, 400 to 550 mM, 400 to 500 mM, 400 to 450 mM, 450 to 1000 mM, 450 to 950 mM, 450 to 900 mM, 450 to 850 mM, 450 to 800 mM, 450 to 750 mM, 450 to 700 mM, 450 to 650 mM, 450 to 600 mM, 450 to 550 mM, or 450 to 500 mM.

MVA (in particular those disclosed in WO90/10459, WO92/07000, WO95/09241, WO98/04705, WO99/03885, WO2004/111082, WO2007/121894, WO2014/009438 and WO2014/009433) is generally amplified in primary avian cells, in which case no protease treatment is necessary for elimination of primary avian cells proteins, since primary cells are not considered as dangerous. Thus, for MVA, and more generally when the poxvirus (preferably vaccinia virus) present in the formulation has been purified by a method that does not involve treatment by at least one protease, said monovalent salt (in particular NaCl) may be present in relatively low concentration, notably in a concentration of 10 to 200 mM, 10 to 150 mM, 10 to 100 mM, 10 to 90 mM, 10 to 80 mM, 10 to 75 mM, 20 to 200 mM, 20 to 150 mM, 20 to 100 mM, 20 to 90 mM, 20 to 80 mM, 20 to 75 mM, 25 to 200 mM, 25 to 150 mM, 25 to 100 mM, 25 to 90 mM, 25 to 80 mM, 25 to 75 mM, 30 to 200 mM, 30 to 150 mM, 30 to 100 mM, 30 to 90 mM, 30 to 80 mM, 30 to 75 mM, 40 to 200 mM, 40 to 150 mM, 40 to 100 mM, 40 to 90 mM, 40 to 80 mM, 40 to 75 mM, 50 to 200 mM, 50 to 150 mM, 50 to 100 mM, 50 to 90 mM, 50 to 80 mM, 50 to 75 mM, 60 to 200 mM, 60 to 150 mM, 60 to 100 mM, 60 to 90 mM, 60 to 80 mM, 60 to 75 mM, 70 to 200 mM, 70 to 150 mM, 70 to 100 mM, 70 to 90 mM, 70 to 80 mM, or 70 to 75 mM, more preferably in a concentration close to 75 mM, such as 50 to 100 mM, 60 to 90 mM, 70 to 80 mM, or about 75 mM.

Other strains of poxviruses, and in particular oncolytic vaccinia viruses, such as Wyeth or Copenhagen vaccinia virus (notably those disclosed in WO2007/030668, WO2008/113078, WO2009/065546, WO2009/065547), are generally amplified on various immortalized cell lines. Some of these cell lines may contain oncogenes and elimination or at least drastic reduction of producing cells DNA and proteins is in this case required by health authorities. For this purpose, the purification process generally includes at least one step of treatment with at least one protease. Remaining traces of protease(s) may, particularly in a liquid formulation, have deleterious effects of vaccinia virus stability. In this respect, the inventors found that increasing the concentration of said monovalent salt (in particular NaCl) results in improved stability of vaccinia virus. Without being bound by theory, it is believed that an increased concentration of said monovalent salt (in particular NaCl) has inhibitory effect on remaining traces of protease(s).

Therefore, when the poxvirus (in particular a vaccinia virus) present in the formulation has been purified by a method that involves at least one step of treatment with at least one protease, said monovalent salt (in particular NaCl) is preferably present in a concentration of 100 to 1000 mM, 100 to 950 mM, 100 to 900 mM, 100 to 850 mM, 100 to 800 mM, 100 to 750 mM, 100 to 700 mM, 100 to 650 mM, 100 to 600 mM, 100 to 550 mM, 100 to 500 mM, 100 to 450 mM, 100 to 400 mM, 100 to 350 mM, 100 to 300 mM, 100 to 250 mM, 100 to 200 mM, 150 to 1000 mM, 150 to 950 mM, 150 to 900 mM, 150 to 850 mM, 150 to 800 mM, 150 to 750 mM, 150 to 700 mM, 150 to 650 mM, 150 to 600 mM, 150 to 550 mM, 150 to 500 mM, 150 to 450 mM, 150 to 400 mM, 150 to 350 mM, 150 to 300 mM, 150 to 250 mM, 150 to 200, 200 to 1000 mM, 200 to 950 mM, 200 to 900 mM, 200 to 850 mM, 200 to 800 mM, 200 to 750 mM, 200 to 700 mM, 200 to 650 mM, 200 to 600 mM, 200 to 550 mM, 200 to 500 mM, 200 to 450 mM, 200 to 400 mM, 200 to 350 mM, 200 to 300 mM, 200 to 250 mM, 250 to 1000 mM, 250 to 950 mM, 250 to 900 mM, 250 to 850 mM, 250 to 800 mM, 250 to 750 mM, 250 to 700 mM, 250 to 650 mM, 250 to 600 mM, 250 to 550 mM, 250 to 500 mM, 250 to 450 mM, 250 to 400 mM, 250 to 350 mM, 250 to 300 mM, 300 to 1000 mM, 300 to 950 mM, 300 to 900 mM, 300 to 850 mM, 300 to 800 mM, 300 to 750 mM, 300 to 700 mM, 300 to 650 mM, 300 to 600 mM, 300 to 550 mM, 300 to 500 mM, 300 to 450 mM, 300 to 400 mM, 300 to 350 mM, 350 to 1000 mM, 350 to 950 mM, 350 to 900 mM, 350 to 850 mM, 350 to 800 mM, 350 to 750 mM, 350 to 700 mM, 350 to 650 mM, 350 to 600 mM, 350 to 550 mM, 350 to 500 mM, 350 to 450 mM, 350 to 400 mM, 400 to 1000 mM, 400 to 950 mM, 400 to 900 mM, 400 to 850 mM, 400 to 800 mM, 400 to 750 mM, 400 to 700 mM, 400 to 650 mM, 400 to 600 mM, 400 to 550 mM, 400 to 500 mM, 400 to 450 mM, 450 to 1000 mM, 450 to 950 mM, 450 to 900 mM, 450 to 850 mM, 450 to 800 mM, 450 to 750 mM, 450 to 700 mM, 450 to 650 mM, 450 to 600 mM, 450 to 550 mM, or 450 to 500 mM. For instance, said monovalent salt may be present in a concentration close to 200 mM, such as 100 to 300 mM, 150 to 250 mM, or about 200 mM. Alternatively, said monovalent salt may be present in a concentration close to 500 mM, such as 250 to 750 mM, 400 to 600 mM, or about 500 mM. In still another embodiment, said monovalent salt may be present in a concentration close to 750 mM, such as 500 to 1000 mM, 700 to 800 mM, or about 750 mM.

Disaccharide or Sugar Alcohol

Liquid formulations according to the invention comprise a pharmaceutically acceptable disaccharide or sugar alcohol.

This pharmaceutically acceptable disaccharide or sugar alcohol is a cryoprotectant and is believed to protect the poxvirus (in particular vaccinia virus) at low storage temperature, such as at about +5° C. In addition, such pharmaceutically acceptable disaccharide or sugar alcohol increases viscosity of the liquid formulation, which might limit interactions between poxvirus (in particular vaccinia virus) and potentially deleterious compounds.

The pharmaceutically acceptable disaccharide or sugar alcohol may notably be selected from sucrose, trehalose, maltose, lactose, mannitol, and sorbitol, preferably said pharmaceutically acceptable disaccharide or sugar alcohol is sucrose.

The pharmaceutically acceptable disaccharide or sugar alcohol (in particular those mentioned above and notably sucrose) is preferably present in a concentration of 5 to 20% (weight in g/volume in L, referred to as w/v). In particular, it may be present in a concentration of 5 to 19% (w/v), 5 to 18% (w/v), 5 to 17% (w/v), 5 to 16% (w/v), 5 to 15% (w/v), 5 to 14% (w/v), 5 to 13% (w/v), 5 to 12% (w/v), 5 to 11% (w/v), 5 to 10% (w/v), 6 to 20% (w/v), 6 to 19% (w/v), 6 to 18% (w/v), 6 to 17% (w/v), 6 to 16% (w/v), 6 to 15% (w/v), 6 to 14% (w/v), 6 to 13% (w/v), 6 to 12% (w/v), 6 to 11% (w/v), 6 to 10% (w/v), 7 to 20% (w/v), 7 to 19% (w/v), 7 to 18% (w/v), 7 to 17% (w/v), 7 to 16% (w/v), 7 to 15% (w/v), 7 to 14% (w/v), 7 to 13% (w/v), 7 to 12% (w/v), 7 to 11% (w/v), 7 to 10% (w/v), 8 to 20% (w/v), 8 to 19% (w/v), 8 to 18% (w/v), 8 to 17% (w/v), 8 to 16% (w/v), 8 to 15% (w/v), 8 to 14% (w/v), 8 to 13% (w/v), 8 to 12% (w/v), 8 to 11% (w/v), 8 to 10% (w/v), 9 to 20% (w/v), 9 to 19% (w/v), 9 to 18% (w/v), 9 to 17% (w/v), 9 to 16% (w/v), 9 to 15% (w/v), 9 to 14% (w/v), 9 to 13% (w/v), 9 to 12% (w/v), 9 to 11% (w/v), or 9 to 10% (w/v). Preferably, said pharmaceutically acceptable disaccharide or sugar alcohol (in particular those mentioned above and notably sucrose) is preferably present in a concentration of close to 10% (w/v), such as 5 to 15% (w/v), 6 to 14% (w/v), 7 to 13% (w/v), 8 to 12% (w/v), 9 to 11% (w/v), or about 10%.

Chelating Agent

Liquid formulations according to the invention comprise a pharmaceutically acceptable chelating agent, and in particular an agent chelating dications.

The reasons why said pharmaceutically acceptable chelating agent improves stability of poxvirus (in particular vaccinia virus) in the liquid state are not really understood.

Indeed, as explained in background art section, the effect of EDTA on virus stability significantly differs between different viruses, and no obvious classification of viruses for which EDTA has beneficial versus viruses for which EDTA has no beneficial or even deleterious effect can be easily made. In particular, while a significant beneficial effect has been found for adenovirus (non-enveloped DNA virus, see EVANS et al. J Pharm Sci. 2004 October, 93(10):2458-75; and U.S. Pat. No. 7,456,009), no significant beneficial effect has been found for influenza virus (enveloped RNA virus, see US2007/0161085), canine parvovirus (non-enveloped DNA virus), canine adenovirus type 2 (non-enveloped DNA virus), canine distemper virus (enveloped RNA paramyxovirus) and canine parainfluenza virus (enveloped RNA paramyxovirus) (see WO2014/029702). Finally, a deleterious effect has been found for Newcastle virus (enveloped RNA paramyxovirus, see U.S. Pat. No. 7,914,979).

However, as demonstrated in the experimental section, said pharmaceutically acceptable chelating agent has an essential role in stabilization of poxvirus (in particular vaccinia virus) in liquid formulations according to the present invention.

The pharmaceutically acceptable chelating agent may notably be selected from ethylenediaminetetraacetic acid (EDTA), 1,2-bis(o-aminophenoxy)ethane-N,N,N',N'-tetraacetic acid (BAPTA), ethylene glycol tetraacetic acid (EGTA), dimercaptosuccinic acid (DMSA), diethylene triamine pentaacetic acid (DTPA), and 2,3-Dimercapto-1-propanesulfonic acid (DMPS), preferably said pharmaceutically acceptable chelating agent is EDTA.

The pharmaceutically acceptable chelating agent (in particular those mentioned above and notably EDTA) is preferably present in a concentration of at least 50 µM. In particular, it may be present in a concentration of 50 to 1000 µM, 50 to 750 µM, 50 to 500 µM, 50 to 400 µM, 50 to 300 µM, 50 to 250 µM, 50 to 200 µM, 50 to 150 µM; 50 to 100 µM, 50 to 75 µM, 75 to 1000 µM, 75 to 750 µM, 75 to 500 µM, 75 to 400 µM, 75 to 300 µM, 75 to 250 µM, 75 to 200 µM, 75 to 150 µM; 75 to 100 µM, 100 to 1000 µM, 100 to 750 µM, 100 to 500 µM, 100 to 400 µM, 100 to 300 µM, 100 to 250 µM, 100 to 200 µM, 100 to 150 µM; 150 to 1000 µM, 150 to 750 µM, 150 to 500 µM, 150 to 400 µM, 150 to 300 µM, 150 to 250 µM, 150 to 200 µM. Said pharmaceutically acceptable chelating agent (in particular those mentioned above and notably EDTA) may notably be present in a concentration close to 150 µM, such as 50 to 250 µM, 100 to 200 µM, or about 150 µM. However, higher concentrations may be present, since no deleterious effect on stability has been observed, even at low concentrations.

Optional Additional Components

Liquid formulations according to the invention may further comprise additional compounds with stabilizing effect on vaccinia virus.

$C_2$-$C_3$ Alcohol

While the presence of a pharmaceutically acceptable buffer permitting to have a pH between 6.5 and 8.5, a monovalent salt, a pharmaceutically acceptable disaccharide or sugar-alcohol, and a pharmaceutically acceptable chelating agent has been found to be essential for stabilization of vaccinia virus in the liquid state, the inventors also found that the additional presence of a low concentration of a $C_2$-$C_3$ alcohol, while not necessary for stabilization of vaccinia virus, synergizes with the presence of a chelating agent to further improve stability of vaccinia virus in liquid state. In contrast, a too high concentration of the same $C_2$-$C_3$ alcohol has deleterious effects on vaccinia virus stability in the liquid state. Therefore, the liquid formulations according to the invention preferably further comprise a $C_2$-$C_3$ alcohol in a concentration of 0.05 to 5% (volume/volume or v/v). This finding was quite unexpected, because poxviruses, and in particular vaccinia viruses, are enveloped viruses, for which the addition of a polar solvent might be expected to alter the envelop, contrary to the case of non-enveloped viruses such as adenoviruses.

Said $C_2$-$C_3$ alcohol may notably be selected from ethanol and isopropanol, preferably said $C_2$-$C_3$ alcohol is ethanol.

Said $C_2$-$C_3$ alcohol (in particular those mentioned above and notably ethanol) may notably be present in a concentration of 0.05 to 5% (v/v), 0.05 to 4% (v/v), 0.05 to 3% (v/v), 0.05 to 2% (v/v), 0.05 to 1% (v/v), 0.05 to 0.9% (v/v), 0.05 to 0.8% (v/v), 0.05 to 0.7% (v/v), 0.05 to 0.6% (v/v), 0.05 to 0.5% (v/v), 0.1 to 5% (v/v), 0.1 to 4% (v/v), 0.1 to 3% (v/v), 0.1 to 2% (v/v), 0.1 to 1% (v/v), 0.1 to 0.9% (v/v), 0.1 to 0.8% (v/v), 0.1 to 0.7% (v/v), 0.1 to 0.6% (v/v), 0.1 to 0.5% (v/v), 0.2 to 5% (v/v), 0.2 to 4% (v/v), 0.2 to 3% (v/v), 0.2 to 2% (v/v), 0.2 to 1% (v/v), 0.2 to 0.9% (v/v), 0.2 to 0.8% (v/v), 0.2 to 0.7% (v/v), 0.2 to 0.6% (v/v), 0.2 to 0.5% (v/v), 0.3 to 5% (v/v), 0.3 to 4% (v/v), 0.3 to 3% (v/v), 0.3 to 2% (v/v), 0.3 to 1% (v/v), 0.3 to 0.9% (v/v), 0.3 to 0.8% (v/v), 0.3 to 0.7% (v/v), 0.3 to 0.6% (v/v), 0.3 to 0.5% (v/v), 0.4 to 5% (v/v), 0.4 to 4% (v/v), 0.4 to 3% (v/v), 0.4 to 2% (v/v), 0.4 to 1% (v/v), 0.4 to 0.9% (v/v), 0.4 to 0.8% (v/v), 0.4 to 0.7% (v/v), 0.4 to 0.6% (v/v), 0.4 to 0.5% (v/v), 0.5 to 5% (v/v), 0.5 to 4% (v/v), 0.5 to 3% (v/v), 0.5 to 2% (v/v), 0.5 to 1% (v/v), 0.5 to 0.9% (v/v), 0.5 to 0.8% (v/v), 0.5 to 0.7% (v/v), or 0.5 to 0.6% (v/v). Preferably, said $C_2$-$C_3$ alcohol (in particular those mentioned above and notably ethanol) is present in a concentration not exceeding 2% (v/v) (in particular any range disclosed above with a higher value of at most 2%) and more preferably close to 0.5% (v/v), such as 0.1 to 1% (v/v), 0.1 to 0.9% (v/v), 0.2 to 0.8% (v/v), 0.3 to 0.7% (v/v), 0.4 to 0.6% (v/v), most preferably about 0.5% (v/v).

Sodium Glutamate

White its stabilizing effect is less pronounced, the liquid formulations according to the invention may also comprise sodium glutamate in a concentration tower than 10 mM, such as 0 to 10 mM, 0 to 9 mM, 0 to 8 mM, 0 to 7.5 mM, 0 to 7 mM, 0 to 6.5 mM, 0 to 6 mM, 0 to 5.5 mM, 0 to 5 mM, 1 to 10 mM, 1 to 9 mM, 1 to 8 mM, 1 to 7.5 mM, 1 to 7 mM, 1 to 6.5 mM, 1 to 6 mM, 1 to 5.5 mM, 1 to 5 mM, 2 to 10 mM, 2 to 9 mM, 2 to 8 mM, 2 to 7.5 mM, 2 to 7 mM, 2 to 6.5 mM, 2 to 6 mM, 2 to 5.5 mM, 2 to 5 mM, 2.5 to 10 mM, 2.5 to 9 mM, 2.5 to 8 mM, 2.5 to 7.5 mM, 2.5 to 7 mM, 2.5 to 6.5 mM, 2.5 to 6 mM, 2.5 to 5.5 mM, 2.5 to 5 mM, 3 to 10 mM, 3 to 9 mM, 3 to 8 mM, 3 to 7.5 mM, 3 to 7 mM, 3 to 6.5 mM, 3 to 6 mM, 3 to 5.5 mM, 3 to 5 mM, 3.5 to 10 mM, 3.5 to 9 mM, 3.5 to 8 mM, 3.5 to 7.5 mM, 3.5 to 7 mM, 3.5 to 6.5 mM, 3.5 to 6 mM, 3.5 to 5.5 mM, 3.5 to 5 mM, 4 to 10 mM, 4 to 9 mM, 4 to 8 mM, 4 to 7.5 mM, 4 to 7 mM, 4 to 6.5 mM, 4 to 6 mM, 4 to 5.5 mM, 4 to 5 mM, 4.5 to 10 mM, 4.5 to 9 mM, 4.5 to 8 mM, 4.5 to 7.5 mM, 4.5 to 7 mM, 4.5 to 6.5 mM, 4.5 to 6 mM, 4.5 to 5.5 mM, 4.5 to 5 mM, 5 to 10 mM, 5 to 9 mM, 5 to 8 mM, 5 to 7.5 mM, 5 to 7 mM, 5 to 6.5 mM, 5 to 6 mM, or 5 to 5.5 mM.

In particular, the inventors have found that, notably for MVA, the presence of sodium glutamate in a concentration of about 5 mM is optimal. When sodium glutamate is present in liquid formulations according to the invention, it is thus preferably present in a concentration close to 5 mM, such as 2.5 to 7.5 mM, 3 to 7 mM, 3.5 to 6.5 mM, 4 to 6 mM, 4.5 to 5.5 mM, more preferably about 5 mM.

Potentially Excluded Compounds

Surfactant

Non-ionic surfactants have been shown to induce stabilization of various viruses in the liquid state (see EVANS et al. J Pharm Sci. 2004 October, 93(10):2458-75, U.S. Pat. No. 7,456,009, SHI et al. J Pharm Sci. 2005 July, 94(7): 1538-51, US2007/0161085).

However, for vaccinia virus, the inventors found that the presence of a surfactant such as non-ionic surfactant Tween 80 (also known as polysorbate 80) at low concentration has no beneficial effect and that concentrations above 0.02% v/v or even above 0.005% v/v are deleterious to the stability of vaccinia virus (see Example 1).

If polysorbate, or more generally a non-ionic surfactant or even any surfactant is present in a liquid composition according to the invention, it should be present in a concentration lower than 0.1%, preferably lower than 0.05% (v/v), lower than 0.04% (v/v), lower than 0.03% (v/v), lower than 0.02% (v/v), lower than 0.01% (v/v), lower than 0.009% (v/v), lower than 0.008% (v/v), lower, than 0.007% (v/v), tower than 0.006% (v/v), lower than 0.005% (v/v), lower than 0.004% (v/v), lower than 0.003% (v/v), lower than 0.002% (v/v), or even lower than 0.001% (v/v).

In another preferred embodiment of a liquid composition according to the invention, the liquid composition is free of polysorbate, or more generally free of non-ionic surfactants, or even more generally free of any surfactant.

In a preferred embodiment, the liquid formulation according to the invention is free of a surfactant or comprises a surfactant at a concentration lower than 0.1%, preferably lower than 0.05% (v/v), lower than 0.04% (v/v), lower than 0.03% (v/v), tower than 0.02% (v/v), lower than 0.01% (v/v), lower than 0.009% (v/v), lower than 0.008% (v/v), lower than 0.007% (v/v), tower than 0.006% (v/v), lower than 0.005% (v/v), lower than 0.004% (v/v), lower than 0.003% (v/v), lower than 0.002% (v/v), or even lower than 0.001% (v/v).

Divalent Salts

Divalent salts such as $MgCl_2$ or $CaCl_2$ have been found to induce stabilization of various viruses in the liquid state (see EVANS et al. J Pharm Sci. 2004 October, 93(10):2458-75 and U.S. Pat. No. 7,456,009). In such cases, divalent cations were present in the liquid formulation at a concentration of at least 0.5 mM, and preferably at least 1 mM.

The inventors however found that the presence of divalent salts does not have high beneficial effect on vaccinia virus stability (see Example 1), and rather has deleterious effects at higher concentrations (at least 75 mM). Liquid formulations according to the invention may thus be free of $MgCl_2$ and/or $CaCl_2$, or more generally of divalent salts. However, since divalent cations appear to have no deleterious effect on vaccinia virus stability at low concentration, such divalent cations may be present in liquid formulations according to the invention, in particular in low concentration. When such divalent cations (in particular $MgCl_2$ or $CaCl_2$) are present in liquid formulations according to the invention, they are nevertheless preferably present at a concentration lower than 100 mM, preferably lower than 90 mM, lower than 80 mM, lower than 75 mM, lower than 70 mM, lower than 60 mM, tower than 50 mM, lower than 45 mM, lower than 40 mM, lower than 35 mM, lower than 30 mM, lower than 25 mM, lower than 20 mM, lower than 15 mM, lower than 10 mM, lower than 9 mM, lower than 8 mM, lower than 7 mM, lower than 6 mM, lower than 5 mM, lower than 4 mM, lower than 3 mM, lower than 2 mM, more preferably lower than 1 mM, lower than 0.9 mM, lower than 0.8 mM, lower than 0.7 mM, lower than 0.6 mM, lower than 0.5 mM.

In a preferred embodiment, the liquid formulation according to the invention is free of divalent salts or comprises divalent salts at a concentration lower than 100 mM, preferably lower than 90 mM, lower than 80 mM, lower than 75 mM, lower than 70 mM, lower than 60 mM, lower than 50 mM, lower than 45 mM, lower than 40 mM, lower than 35 mM, lower than 30 mM, lower than 25 mM, lower than 20 mM, lower than 15 mM, lower than 10 mM, lower than 9 mM, lower than 8 mM, lower than 7 mM, lower than 6 mM, lower than 5 mM, lower than 4 mM, lower than 3 mM, lower than 2 mM, more preferably lower than 1 mM, lower than 0.9 mM, lower than 0.8 mM, lower than 0.7 mM, lower than 0.6 mM, lower than 0.5 mM.

Amino Acids Other than Glutamic Acid

Amino acids, and in particular histidine, arginine or methionine, have been found to induce stabilization of various viruses in the liquid state (see EVANS et al. J Pharm Sci. 2004 October, 93(10):2458-75, U.S. Pat. No. 7,456,009, US2007/0161085, U.S. Pat. No. 7,914,979, WO2014/029702, WO2014/053571). When histidine is present in a liquid formulation in order to improve stability, histidine is generally present in a concentration of at least 5 mM, and preferably at least 10 mM (see EVANS et al. J Pharm Sci. 2004 October, 93(10):2458-75, U.S. Pat. No. 7,456,009, WO2014/029702). When arginine is present in a liquid formulation in order to improve stability, arginine is generally present in a concentration of at least 50 mM (see US2007/0161085, at least 1% w/v arginine corresponding to at least about 57.4 mM), and sometimes preferably at least 150 mM, and in particular about 300 mM (see WO2014/029702). When methionine is present in a liquid formulation in order to improve stability, methionine is generally present in a concentration of at least 25 mM, and preferably about 67 mM (see WO2014/029702). The inventors however found that the presence of amino acids other than glutamic acid (arginine, histidine or amino acids in general) has no beneficial effect on vaccinia virus stability (see Example 1).

Liquid formulations according to the invention may thus be free of histidine. Alternatively or in addition, liquid formulations according to the invention may be free of arginine. Alternatively or in addition, liquid formulations according to the invention may be free of methionine. In particular, liquid formulations according to the invention may be free of arginine and methionine, or even free of histidine, arginine and methionine. More generally, liquid formulations according to the invention may be free of amino acids other than glutamic acid.

However, while having no beneficial effect, such amino acids other than sodium glutamate were not found to have deleterious effect, and may thus be present in liquid formulations according to the invention, in particular in tow concentration.

When histidine is present in liquid formulations according to the invention, it is nevertheless preferably present at a concentration lower than 10 mM, preferably lower than 9 mM, lower than 8 mM, lower than 7.5 mM, lower than 7 mM, tower than 6 mM, or even lower than 5 mM.

Similarly, when arginine is present in liquid formulations according to the invention, it is nevertheless preferably present at a concentration tower than 300 mM, preferably lower than 150 mM, lower than 100 mM, lower than 75 mM, or even lower than 50 mM. Also, when methionine is present in liquid formulations according to the invention, it is nevertheless preferably present at a concentration lower than 60 mM, preferably lower than 50 mM, tower than 40 mM, lower than 30 mM, or even lower than 25 mM. More generally, when one or more amino acids other than sodium glutamate is/are present in liquid formulations according to the invention, it/they is/are preferably present at a concentration tower than 300 mM, preferably lower than 150 mM, lower than 100 mM, lower than 75 mM, lower than 50 mM, lower than 40 mM, lower than 30 mM, lower than 25 mM, lower than 20 mM, lower than 10 mM, lower than 9 mM, lower than 8 mM, lower than 7.5 mM, lower than 7 mM, lower than 6 mM, or even lower than 5 mM.

In a preferred embodiment, the liquid formulation according to the invention is free of histidine or comprises histidine at a concentration lower than 10 mM, preferably lower than 9 mM, lower than 8 mM, lower than 7.5 mM, lower than 7 mM, lower than 6 mM, or even lower than 5 mM.

In a preferred embodiment, the liquid formulation according to the invention is free of arginine or comprises arginine at a concentration lower than 300 mM, preferably tower than 150 mM, lower than 100 mM, lower than 75 mM, or even lower than 50 mM.

In a preferred embodiment, the liquid formulation according to the invention is free of methionine or comprises methionine at a concentration lower than 60 mM, preferably lower than 50 mM, lower than 40 mM, lower than 30 mM, or even lower than 25 mM.

In a preferred embodiment, the liquid formulation according to the invention is free of amino acids other than sodium glutamate or comprises amino acids other than sodium glutamate at a concentration lower than 300 mM, preferably lower than 150 mM, lower than 100 mM, lower than 75 mM, lower than 50 mM, lower than 40 mM, lower than 30 mM, lower than 25 mM, lower than 20 mM, lower than 10 mM, lower than 9 mM, lower than 8 mM, lower than 7.5 mM, lower than 7 mM, lower than 6 mM, or even lower than 5 mM.

Urea

The inventors also found that urea has no beneficial effect on vaccinia virus stability (see Example 1).

Liquid formulations according to the invention may thus preferably be free of urea.

High Molecular Weight Polymers

Freeze-dried virus formulations generally contain high molecular weight polymers such as dextran or polyvinylpyrrolidone (PVP), which assist in the formation of the cake during freeze-drying (see EP1418942 and WO2014/053571).

However, such high molecular weight polymers are not useful for stabilization of vaccinia virus in the liquid state and liquid formulations according to the invention may thus be free of such high molecular weight polymers. If present in liquid formulations according to the invention, they are preferably present at a concentration lower than 10 g/L, preferably lower than 7.5 g/L, lower than 5 g/L, lower than 2.5 g/L, or even lower than 1 g/L.

In a preferred embodiment, the liquid formulation according to the invention is thus free of dextran, PVP or more generally of high molecular weight polymers or comprises dextran, PVP or more generally of high molecular weight polymers at a concentration lower than 10 g/L, preferably lower than 7.5 g/L, lower than 5 g/L, lower than 2.5 g/L, or even lower than 1 g/L.

Animal- or Human-derived Stabilizers

Animal- or human-derived stabilizers such as serum or gelatin have been used for a long time for stabilization of live viruses (see US2007/0161085). However, such animal- or human-derived stabilizers of animal or human origin potentially involve a health risk, due to potential contamination by viral or non-conventional agents.

Such animal- or human-derived stabilizers are not necessary for stability of vaccinia virus in liquid formulations according to the invention, and liquid formulations according to the invention are thus preferably free of animal- or human-derived stabilizers, such as serum or gelatin.

Preferred Formulations

Various specific compounds belonging to the family of each essential or optional element of the formulations according to the invention have been described above in the section specifically relating to this element. In the context of the invention, each list of appropriate compounds for a particular element and each specific compound disclosed for a particular element may be combined with any generic other element, list of appropriate compounds for said other element or any specific compound disclosed for said other element.

In particular, preferred embodiments of an essential or optional element of the formulations according to the invention may be combined with any generic other element or with preferred embodiments of said other element.

Particularly preferred formulations according to the invention include formulations comprising, consisting essentially of, or consisting of elements mentioned in Table 1 below:

TABLE 1

Preferred formulations according to the invention comprise, essentially consist of or consist of the above elements.

| N° | Poxvirus | Buffer | Monovalent salt | Disaccharide/ sugar alcohol | Chelating agent | Other compounds | Other features |
|---|---|---|---|---|---|---|---|
| 1 | vaccinia virus | buffer with buffering capacity between pH 7 and 8 | monovalent salt | disaccharide/ sugar alcohol | chelating agent | / | / |
| 2 | | | | | | $C_2$-$C_3$ alcohol | |
| 3 | | | | | | $C_2$-$C_3$ alcohol + Na glutamate | |
| 4 | vaccinia virus $10^7$ PFU/mL to $10^{12}$ PFU/mL | buffer with buffering capacity between pH 7 and 8 10 to 50 mM | monovalent salt 10 to 50 mM | disaccharide/ sugar alcohol 5 to 20% (w/v) | chelating agent at least 50 μM | / | / |
| 5 | | | | | | $C_2$-$C_3$ alcohol 0.05 to 5% (v/v) | |
| 6 | | | | | | $C_2$-$C_3$ alcohol 0.05 to 5% (v/v) + Na glutamate 0 to 10 mM | |
| 7 | vaccinia virus | Tris-HCl | NaCl | sucrose | EDTA | / | / |
| 8 | | | | | | ethanol | |
| 9 | | | | | | ethanol + Na glutamate | |
| 10 | vaccinia virus $10^7$ PFU/mL to $10^{12}$ PFU/mL | Tris-HCl 10 to 50 mM | NaCl 10 to 500 mM | Sucrose 5 to 20% (w/v) | EDTA at least 50 μM | / | / |
| 11 | | | | | | ethanol 0.05 to 5% (v/v) | |
| 12 | | | | | | ethanol 0.05 to 5% (v/v) + Na glutamate 0 to 10 mM | |
| 13 | vaccinia virus purified by a method that does not involve treatment by at least one protease | Tris-HCl | NaCl | sucrose | EDTA | / | / |
| 14 | | | | | | ethanol | |
| 15 | | | | | | ethanol + Na glutamate | |
| 16 | vaccinia virus purified by a method that does not involve treatment by at least one protease $10^7$ PFU/mL to $10^{12}$ PFU/mL | Tris-HCl 10 to 50 mM | NaCl 10 to 200 mM | Sucrose 5 to 20% (w/v) | EDTA at least 50 μM | / | / |
| 17 | | | | | | ethanol 0.05 to 5% (v/v) | |
| 18 | | | | | | ethanol 0.05 to 5% (v/v) + Na glutamate 0 to 10 mM | |
| 19 | vaccinia virus purified by a method that involves at least one step of treatment with at least one protease | Tris-HCl | NaCl | sucrose | EDTA | / | / |
| 20 | | | | | | ethanol | |
| 21 | | | | | | ethanol + Na glutamate | |
| 22 | vaccinia virus purified by a method that involves at least one step of treatment with at least one protease $10^7$ PFU/mL to $10^{12}$ PFU/mL | Tris-HCl 10 to 50 mM | NaCl 100 to 500 mM | Sucrose 5 to 20% (w/v) | EDTA at least 50 μM | / | / |
| 23 | | | | | | ethanol 0.05 to 5% (v/v) | |
| 24 | | | | | | ethanol 0.05 to 5% (v/v) + Na glutamate 0 to 10 mM | |
| 25 | vaccinia virus | Tris-HCl | NaCl | Trehalose | EDTA | / | / |
| 26 | | | | | | ethanol | |
| 27 | | | | | | ethanol + Na glutamate | |
| 28 | vaccinia virus $10^7$ PFU/mL to $10^{12}$ PFU/mL | Tris-HCl 10 to 50 mM | NaCl 10 to 500 mM | Trehalose 5 to 20% (w/v) | EDTA at least 50 μM | / | / |
| 29 | | | | | | ethanol 0.05 to 5% (v/v) | |
| 30 | | | | | | ethanol 0.05 to 5% (v/v) + Na glutamate 0 to 10 mM | |

TABLE 1-continued

Preferred formulations according to the invention comprise, essentially consist of or consist of the above elements.

| N° | Poxvirus | Buffer | Monovalent salt | Disaccharide/ sugar alcohol | Chelating agent | Other compounds | Other features |
|---|---|---|---|---|---|---|---|
| 31 | vaccinia virus | Tris-HCl | NaCl | Trehalose | EDTA | / | / |
| 32 | purified by a | | | | | ethanol | |
| 33 | method that does not involve treatment by at least one protease | | | | | ethanol + Na glutamate | |
| 34 | vaccinia virus | Tris-HCl | NaCl | Trehalose | EDTA | / | / |
| 35 | purified by a | 10 to 50 mM | 10 to 200 mM | 5 to 20% (w/v) | at least 50 μM | ethanol 0.05 to 5% (v/v) | |
| 36 | method that does not involve treatment by at least one protease $10^7$ PFU/mL to $10^{12}$ PFU/mL | | | | | ethanol 0.05 to 5% (v/v) + Na glutamate 0 to 10 mM | |
| 37 | vaccinia virus | Tris-HCl | NaCl | Trehalose | EDTA | / | / |
| 38 | purified by a | | | | | ethanol | |
| 39 | method that involves at least one step of treatment with at least one protease | | | | | ethanol + Na glutamate | |
| 40 | vaccinia virus | Tris-HCl | NaCl | Trehalose | EDTA | / | / |
| 41 | purified by a | 10 to 50 mM | 100 to 500 mM | 5 to 20% (w/v) | at least 50 μM | ethanol 0.05 to 5% (v/v) | |
| 42 | method that involves at least one step of treatment with at least one protease $10^7$ PFU/mL to $10^{12}$ PFU/mL | | | | | ethanol 0.05 to 5% (v/v) + Na glutamate 0 to 10 mM | |
| 43-84 | | | Anyone of n°1-42 | | | | formulation free of a surfactant or comprises a surfactant at a concentration lower than 0.1% |
| 85-126 | | | Anyone of n°1-42 | | | | formulation free of divalent salts or comprises divalent salts at a concentration lower than 1 mM |
| 127-168 | | | Anyone of n°1-42 | | | | formulation free of histidine or comprises histidine at a concentration lower than 10 mM |
| 169-210 | | | Anyone of n°1-42 | | | | formulation free of arginine or comprises arginine at a concentration lower than 50 mM |
| 211-252 | | | Anyone of n°1-42 | | | | formulation free of methionine or comprises methionine at a concentration lower than 25 mM |
| 253-294 | | | Anyone of n°1-42 | | | | formulation free of amino acids other than sodium glutamate or comprises amino acids other than sodium glutamate at a concentration lower than 10 mM |
| 295-336 | | | Anyone of n°1-42 | | | | formulation free of a surfactant or comprises a surfactant at a concentration lower than 0.1% + formulation free of divalent salts or comprises divalent salts at a concentration lower than 1 mM + formulation free of histidine or comprises histidine at a concentration lower than 10 mM + formulation free of arginine or comprises arginine at a concentration lower than 50 mM + formulation free of methionine or comprises methionine at a concentration lower than 25 mM |
| 337-378 | | | Anyone of n°1-42 | | | | formulation free of a surfactant or comprises a surfactant at a concentration lower than 0.1% + formulation free of divalent salts or comprises divalent salts at a concentration lower than 1 mM + |

TABLE 1-continued

Preferred formulations according to the invention comprise, essentially consist of or consist of the above elements.

| N° | Poxvirus | Buffer | Monovalent salt | Disaccharide/ sugar alcohol | Chelating agent | Other compounds | Other features |
|---|---|---|---|---|---|---|---|
| | | | | | | | formulation free of amino acids other than sodium glutamate or comprises amino acids other than sodium glutamate at a concentration lower than 10 mM |
| 379 380 381 | vaccinia virus $10^7$ PFU/mL to $10^{12}$ PFU/mL | buffer with buffering capacity between pH 7 and 8 10 to 50 mM | monovalent salt 10 to 1000 mM | disaccharide/ sugar alcohol 5 to 20% (w/v) | chelating agent at least 50 µM | / $C_2$-$C_3$ alcohol 0.05 to 5% (v/v) $C_2$-$C_3$ alcohol 0.05 to 5% (v/v) + Na glutamate 0 to 10 mM | / |
| 382 383 384 | vaccinia virus $10^7$ PFU/mL to $10^{12}$ PFU/mL | Tris-HCl 10 to 50 mM | NaCl 10 to 100 mM | Sucrose 5 to 20% (w/v) | EDTA at least 50 µM | / ethanol 0.05 to 5% (v/v) ethanol 0.05 to 5% (v/v) + Na glutamate 0 to 10 mM | / |
| 385 386 387 | vaccinia virus purified by a method that involves at least one step of treatment with at least one protease $10^7$ PFU/mL to $10^{12}$ PFU/mL | Tris-HCl 10 to 50 mM | NaCl 100 to 1000 mM | Sucrose 5 to 20% (w/v) | EDTA at least 50 µM | / ethanol 0.05 to 5% (v/v) ethanol 0.05 to 5% (v/v) + Na glutamate 0 to 10 mM | / |
| 388 389 390 390 | vaccinia virus $10^7$ PFU/mL to $10^{12}$ PFU/mL | Tris-HCl 10 to 50 mM | NaCl 10 to 1000 mM | Trehalose 5 to 20% (w/v) | EDTA at least 50 µM | / ethanol 0.05 to 5% (v/v) ethanol 0.05 to 5% (v/v) + Na glutamate 0 to 10 mM | / |
| 391 392 393 | vaccinia virus purified by a method that involves at least one step of treatment with at least one protease $10^7$ PFU/mL to $10^{12}$ PFU/mL | Tris-HCl 10 to 50 mM | NaCl 100 to 1000 mM | Trehalose 5 to 20% (w/v) | EDTA at least 50 µM | / ethanol 0.05 to 5% (v/v) ethanol 0.05 to 5% (v/v) + Na glutamate 0 to 10 mM | / |
| 394-408 | | | Anyone of n°379-393 | | | | formulation free of a surfactant or comprises a surfactant at a concentration lower than 0.1% |
| 409-423 | | | Anyone of n°379-393 | | | | formulation free of divalent salts or comprises divalent salts at a concentration lower than 1 mM |
| 424-438 | | | Anyone of n°379-393 | | | | formulation free of histidine or comprises histidine at a concentration lower than 10 mM |
| 439-453 | | | Anyone of n°379-393 | | | | formulation free of arginine or comprises arginine at a concentration lower than 50 mM |
| 454-468 | | | Anyone of n°379-393 | | | | formulation free of methionine or comprises methionine at a concentration lower than 25 mM |
| 469-483 | | | Anyone of n°379-393 | | | | formulation free of amino acids other than sodium glutamate or comprises amino acids other than sodium glutamate at a concentration lower than 10 mM |
| 484-498 | | | Anyone of n°379-393 | | | | formulation free of a surfactant or comprises a surfactant at a concentration lower than 0.1% + formulation free of divalent salts or comprises divalent salts at a |

TABLE 1-continued

Preferred formulations according to the invention comprise, essentially consist of or consist of the above elements.

| N° | Poxvirus | Buffer | Monovalent salt | Disaccharide/ sugar alcohol | Chelating agent | Other compounds | Other features |
|---|---|---|---|---|---|---|---|
| 499-513 | | | | | | Anyone of n°379-393 | concentration lower than 1 mM + formulation free of histidine or comprises histidine at a concentration lower than 10 mM + formulation free of arginine or comprises arginine at a concentration lower than 50 mM + formulation free of methionine or comprises methionine at a concentration lower than 25 mM formulation free of a surfactant or comprises a surfactant at a concentration lower than 0.1% + formulation free of divalent salts or comprises divalent salts at a concentration lower than 1 mM + formulation free of amino acids other than sodium glutamate or comprises amino acids other than sodium glutamate at a concentration lower than 10 mM |

Use of a Pharmaceutically Acceptable Chelating Agent for Stabilizing a Vaccinia Virus Against UV Damage Vaccinia virus is particularly sensitive to UV damage (see LYTLE et al. J. Virol. 2005, 79 (22): 14244).

Surprisingly, the inventors found that EDTA has a protecting effect on vaccinia virus against UV damage (see Example 6). The present invention thus also relates to the use of a pharmaceutically acceptable chelating agent for stabilizing a poxvirus (in particular a vaccinia virus) against UV damage.

For stabilization of poxvirus (in particular vaccinia virus) against UV damage, the chelating agent is preferably selected from ethylenediaminetetraacetic acid (EDTA), 1,2-bis(o-aminophenoxy)ethane-N,N,N',N'-tetraacetic acid (BAPTA), ethylene glycol tetraacetic acid (EGTA), dimercaptosuccinic acid (DMSA), diethylene triamine pentaacetic acid (DTPA), and 2,3-Dimercapto-1-propanesulfonic acid (DMPS), preferably said pharmaceutically acceptable chelating agent is EDTA.

When using a pharmaceutically acceptable chelating agent for stabilizing a poxvirus (in particular a vaccinia virus) against UV damage, said poxvirus (in particular vaccinia virus) is preferably in a liquid composition and said pharmaceutically acceptable chelating agent (in particular those mentioned above and notably EDTA) is preferably present in a concentration of at least 50 µM, preferably 50 to 1000 µM, 50 to 750 µM, 50 to 500 µM, 50 to 400 µM, 50 to 300 µM, 50 to 250 µM, 50 to 200 µM, 50 to 150 µM; 50 to 100 µM, 50 to 75 µM, 75 to 1000 µM, 75 to 750 µM, 75 to 500 µM, 75 to 400 µM, 75 to 300 µM, 75 to 250 µM, 75 to 200 µM, 75 to 150 µM; 75 to 100 µM, 100 to 1000 µM, 100 to 750 µM, 100 to 500 µM, 100 to 400 µM, 100 to 300 µM, 100 to 250 µM, 100 to 200 µM, 100 to 150 µM; 150 to 1000 µM, 150 to 750 µM, 150 to 500 µM, 150 to 400 µM, 150 to 300 µM, 150 to 250 µM, or 150 to 200 µM.

Even more preferably, for stabilizing a poxvirus (in particular a vaccinia virus) against UV damage, a liquid formulation according to the invention (as disclosed above) is used.

The following examples merely intend to illustrate the present invention.

EXAMPLES

Example 1: Screening of Candidate Stabilizing Compounds

The effect of various candidate compounds for stabilizing MVA virus in a liquid formulation at +5° C. has been tested based on compounds known from prior art to have stabilizing effect of other types of viruses.

Materials and Methods

Viruses

The following MVA viruses were used:

MVA-MUC1 (TG4010), a recombinant MVA virus expressing MUC1 tumor associated antigen and interleukin 2 (see WO92/07000 and WO95/09241), which was diluted to an initial target concentration of 1-4 $10^8$ PFU/mL.

MVA-HCV (TG4040), a recombinant MVA virus expressing nonstructural HCV proteins (NS3, NS4 and NS5B) from HCV genotype 1 b strain ja (see WO2004/111082), which was diluted to an initial target concentration of 1-4 $10^7$ PFU/mL.

MVA-HPV (TG4001), a recombinant MVA virus expressing human papillomavirus E6 and E7 antigens and interleukin 2 (see WO90/10459, WO95/09241, WO98/04705, WO99/03885, WO2007/121894), which was diluted an initial target concentration of 0.5-2 $10^8$ PFU/mL.

The three MVA viruses were produced in chicken embryo fibroblast, and recovered and purified by a method comprising recovery of infected CEF culture, breakage of cells my mechanical means, and various purification steps that do not involve any step of treatment with a protease.

A recombinant vaccinia virus of strain Wyeth, produced in a human continuous cell line and purified by a method that involves at least one step of treatment with at least one protease (VV Wyeth) was also used, at an initial target titer of 2 $10^8$ to 2 $10^9$ PFU/mL.

Tested Formulations

Tested formulations are represented in Tables 2 to 11 below:

Beneficial Effect of the presence of a monovalent salt:

TABLE 2

Formulations with and without NaCl tested for MVA-MUC1

|  | 0 mM NaCl | 50 mM NaCl |
|---|---|---|
| Tris-HCl (mM) | 10 | 10 |
| Sucrose (% w/v) | 5 | 5 |
| Na Glutamate (mM) | 10 | 10 |
| NaCl (mM) | 0 | 50 |
| pH | 8.0 | 8.0 |

Beneficial effect of the presence of EDTA, EtOH or EDTA/EtOH:

TABLE 3

First formulations with EDTA, EtOH or EDTA/EtOH tested for MVA-HCV

|  | Control DS | Control DS2 | 0.5% EtOH | 1% EtOH | 2% EtOH | 4% EtOH |
|---|---|---|---|---|---|---|
| Tris-HCl (mM) | 10 | 20 | 20 | 20 | 20 | 20 |
| Na Glutamate (mM) | 10 | 5 | 5 | 5 | 5 | 5 |
| Sucrose (% w/v) | 5 | 10 | 10 | 10 | 10 | 10 |
| NaCl (mM) | 50 | 75 | 75 | 75 | 75 | 75 |
| EDTA (µM) | / | / | / | / | / | / |
| EtOH (% v/v) | / | / | 0.5 | 1 | 2 | 4 |
| pH | 7.5 | 7.5 | 7.5 | 7.5 | 7.5 | 7.5 |

|  | 50 µM EDTA | 250 µM EDTA | 500 µM EDTA | 1000 µM EDTA | 50 µM EDTA 1% EtOH | 1000 µM EDTA 1% EtOH |
|---|---|---|---|---|---|---|
| Tris-HCl (mM) | 20 | 20 | 20 | 20 | 20 | 20 |
| Na Glutamate (mM) | 5 | 5 | 5 | 5 | 5 | 5 |
| Sucrose (% w/v) | 10 | 10 | 10 | 10 | 10 | 10 |
| NaCl (mM) | 75 | 75 | 75 | 75 | 75 | 75 |
| EDTA (µM) | 50 | 250 | 500 | 1000 | 50 | 1000 |
| EtOH (% v/v) | / | / | / | / | 1 | 1 |
| pH | 7.5 | 7.5 | 7.5 | 7.5 | 7.5 | 7.5 |

TABLE 4

Further formulations with EDTA, EtOH or EDTA/EtOH tested for MVA-HCV

|  | Control DS | Control DS2 | 250 µM EDTA 0.5% ETOH | 250 µM EDTA 2.5% ETON | 50 µM EDTA 0.5% ETOH | 50 µM EDTA 2.5% ETOH |
|---|---|---|---|---|---|---|
| Tris-HCl (mM) | 10 | 20 | 20 | 20 | 20 | 20 |
| Na Glutamate (mM) | 10 | 2.5 | 2.5 | 2.5 | 2.5 | 2.5 |
| Sucrose (% w/v) | 5 | 10 | 10 | 10 | 10 | 10 |
| NaCl (mM) | 50 | 75 | 75 | 75 | 75 | 75 |
| EDTA (µM) | / | / | 250 | 250 | 50 | 50 |
| EtOH (% v/v) | / | / | 0.5 | 2.5 | 0.5 | 2.5 |
| pH | 7.5 | 7.5 | 7.5 | 7.5 | 7.5 | 8.5 |

|  | 150 µM EDTA 0.5% ETOH | 50 µM EDTA 1.5% ETOH | 150 µM EDTA 2.5% ETOH | 250 µM EDTA 1.5% ETOH | 150 µM EDTA 1.5% ETOH |
|---|---|---|---|---|---|
| Tris-HCl (mM) | 20 | 20 | 20 | 20 | 20 |
| Na Glutamate (mM) | 2.5 | 2.5 | 2.5 | 2.5 | 2.5 |
| Sucrose (% w/v) | 10 | 10 | 10 | 10 | 10 |
| NaCl (mM) | 75 | 75 | 75 | 75 | 75 |
| EDTA (µM) | 150 | 50 | 150 | 250 | 150 |
| EtOH (% v/v) | 0.5 | 1.5 | 2.5 | 1.5 | 1.5 |
| pH | 7.5 | 7.5 | 7.5 | 7.5 | 7.5 |

Beneficial effect of low concentrations of Na glutamate:

TABLE 5

Formulations with Na glutamate tested for MVA-HCV

|  | Control DS | Control D52 | Inv 0 mM | Inv 2.5 mM | Inv 5 mM | Inv 7.5 mM | Inv 10 mM |
|---|---|---|---|---|---|---|---|
| Tris-HCl (mM) | 10 | 10 | 20 | 20 | 20 | 20 | 20 |
| Na Glutamate (mM) | 10 | 0 | 0 | 2.5 | 5 | 7.5 | 10 |
| Sucrose (% w/v) | 5 | 5 | 10 | 10 | 10 | 10 | 10 |
| NaCl (mM) | 50 | 50 | 75 | 75 | 75 | 75 | 75 |
| EDTA (µM) | / | / | 150 | 150 | 150 | 150 | 150 |
| EtOH (% v/v) | / | / | 0.5 | 0.5 | 0.5 | 0.5 | 0.5 |
| pH | 7.5 | 7.5 | 7.5 | 7.5 | 7.5 | 7.5 | 7.5 |

Beneficial effect of a low concentration of sucrose:

TABLE 6

Formulations with sucrose tested for MVA-MUC1

|  | sucrose 1.25% | sucrose 2.5% | sucrose 5% | sucrose 7.5% | sucrose 10% |
|---|---|---|---|---|---|
| Tris-HCl (mM) | 10 | 10 | 10 | 10 | 10 |
| Na Glutamate (mM) | 10 | 10 | 10 | 10 | 10 |
| Sucrose (% w/v) | 1.25 | 2.5 | 5 | 7.5 | 10 |
| NaCl (mM) | 50 | 50 | 50 | 50 | 50 |
| pH | 8.0 | 8.0 | 8.0 | 8.0 | 8.0 |

No beneficial effect and even deleterious effect of polysorbate:

MVA virus:

TABLE 7A

Formulations with or without polysorbate tested for MVA-HPV

|  | DS control | 0.005% PS80 | 0.02% PS80 | 1% PS80 | 1% PS40 |
|---|---|---|---|---|---|
| Tris-HCl (mM) | 10 | 5 | 10 | 10 | 10 |
| Na Glutamate (mM) | 10 | 5 | 5 | 5 | 5 |
| Sucrose (% w/v) | 5 | 5 | 5 | 5 | 5 |
| NaCl (mM) | 50 | 75 | 50 | 75 | 75 |
| Polysorbate-80 (% v/v) | / | 0.005 | 0.02 | 1 | / |
| Polysorbate-40 (% v/v) | / | / | / | / | 1 |
| pH | 7.5 | 7.5 | 7.5 | 7.5 | 7.5 |

VV Wyeth:

TABLE 7B

Formulations with or without polysorbate tested for VV Wyeth

|  | Tris + sucrose | Tris + sucrose + polysorbate 80 |
|---|---|---|
| Tris-HCl (mM) | 30 | 30 |
| Sucrose (% w/v) | 10 | 10 |
| Polysorbate-80 (µg/mL) | 0 | 150 |

No beneficial effect of MgCl$_2$:

MVA virus:

TABLE 8A

Formulations with or without MgCl$_2$ tested for MVA-MUC1.

|  | Control (0M MgCl2) | 0.5M MgCl2 | 1M MgCl2 |
|---|---|---|---|
| Tris-HCl (mM) | 10 | 10 | 10 |
| Na Glutamate (mM) | 10 | 10 | 10 |
| Sucrose (% w/v) | 5 | 5 | 5 |
| NaCl (mM) | 50 | 50 | 50 |
| MgCl2 (M) | 0 | 0.5 | 1 |
| pH | 8.0 | 8.0 | 8.0 |

VV Wyeth:

TABLE 8B

Formulations with or without MgCl$_2$ tested for VV Wyeth

|  | Tris + sucrose | Tris + sucrose + polysorbate 80 |
|---|---|---|
| Tris-HCl (mM) | 30 | 30 |
| Sucrose (% w/v) | 10 | 10 |
| MgCl2 (mM) | 0 | 1000 |

No beneficial effect of arginine:

MVA virus:

TABLE 9A

Formulations with or without arginine tested for MVA-MUC1

|  | Control (0 mM arginine) | 30 mM arginine | 50 mM arginine | 100 mM arginine | 200 mM arginine |
|---|---|---|---|---|---|
| Tris-HCl (mM) | 10 | 10 | 10 | 10 | 10 |
| Na Glutamate (mM) | 10 | 10 | 10 | 10 | 10 |
| Sucrose (% w/v) | 5 | 5 | 5 | 5 | 5 |
| NaCl (mM) | 50 | 50 | 50 | 50 | 50 |
| arginine (mM) | 0 | 30 | 50 | 100 | 200 |
| pH | 8.0 | 8.0 | 8.0 | 8.0 | 8.0 |

VV Wyeth:

TABLE 9B

Formulations with or without arginine tested for VV Wyeth

|  | Tris + sucrose | Tris + sucrose + arginine |
|---|---|---|
| Tris-HCl (mM) | 30 | 30 |
| Sucrose (% w/v) | 10 | 10 |
| arginine (mM) | 0 | 50 |

No beneficial effect of a mixture of amino acids:

TABLE 10

Formulations with or without a mixture of amino acids tested for MVA-MUC1

|  | Control (0% aa) | 1% aa |
|---|---|---|
| Tris-HCl (mM) | 10 | 10 |
| Na Glutamate (mM) | 10 | 10 |
| Sucrose (% w/v) | 5 | 5 |
| NaCl (mM) | 50 | 50 |
| Mixture of amino acids (aa, wt %) | 0 | 1 |
| pH | 8.0 | 8.0 |

No beneficial effect of histidine:

TABLE 11

Formulations with or without histidine tested for MVA-HPV

|  | DS control | 10 mM histidine |
|---|---|---|
| Tris-HCl (mM) | 10 | 20 |
| Na Glutamate (mM) | 10 | 5 |
| Sucrose (% w/v) | 5 | 10 |

TABLE 11-continued

Formulations with or without histidine tested for MVA-HPV

|  | DS control | 10 mM histidine |
|---|---|---|
| NaCl (mM) | 50 | 75 |
| Histidine (mM) | 0 | 10 |
| pH | 7.5 | 7.5 |

Analysis of Stability

Stability was analyzed at +37° C. (±2° C.), +25° C. (±2° C.), and/or +5° C. (±3° C.) (see results section).

At +37° C. (±2° C.) (accelerated stability test), samples were kept in relative humidity of 75% and stability was analyzed by measuring infectious losses during at least 28 days (with intermediate measures at days 7 and 14).

At +25° C. (±2° C.) (accelerated stability test), samples were kept in relative humidity of 60% and stability was analyzed by measuring infectious losses during at least 6 months (with intermediate measures at about 1 month, and at 2 and 3 months).

At +5° C. (±3° C.) (target storage temperature test), samples were kept without any control of relative humidity and stability was analyzed by measuring infectious losses during at least 24 months (with intermediate measures at about 1 month, and at 3, 6, 12, 18 and 24 months).

Infectious losses were calculated by subtracting the number of infectious genomes or particle forming units per mL (IG/mL or PFU/mL) at the time measure to the initial number of IG/mL or PFU/mL at day 0, and expressed as decimal logarithm ($\log_{10}$ (IG/mL or PFU/mL)), abbreviated in the present description as log (IG/mL or PFU/mL).

Measure of Infectious Titers

Infectious titers at a given time may be measured either by measuring the number of infectious genomes (IG) per mL (IG/mL) or by using a plaque assay on BHK-21 cells (infectious vaccinia virus titer is then expressed in Plaque forming units (PFU) per mL (PFU/mL)). Measure of the number of infectious genomes per mL (IG/mL) has been preferred here, since this method is more rapid and more precise. However, while no specific data is shown using plaque assay on BHK-21 cells, it should be noted that infectious titers were at some points measured also using plaque assay on BHK-21 cells and that results were always found to be consistent with results obtained using the infectious genomes method.

Measure of the number of infectious genomes per mL (IG/mL) is performed as follows:

D Day: Infection and Cell Seeding
Virus sample is serially diluted in DMEM culture medium supplemented with 5% Fetal Calf Serum (FCS) in a culture 96-well plate (100 µL per well).
BHK-21 cells are harvested in culture medium (DMEM+ 5% FCS) and seeded at a ratio of 1:100 (100 µL per well) in the 96-well plate containing the viral dilutions.
The culture plate is then incubated at +37° C., 5% $CO_2$ for 24 hours+/−4 hours.

D+1 Day: Lysis of Infected Cells
20-28 h post-infection, supernatants are discarded and cell monolayers are washed 2 times with PBS. 100 µL of the lysis buffer containing proteinase K is added into each well. The plate is incubated at +56° for at least 30 minutes (up to 420 minutes), and then heated at +95° C. for 5 minutes in order to inactivate the proteinase K.

From Day D+1 Up to D+30 (at −20° C.): qPCR Analysis
Cell lysates are 49-time diluted in water and are submitted to qPCR with specific primers and probe set targeting the Secreted Chemokine Binding Protein (SCBP) region of Vaccinia virus genome.
The number of test sample infectious genomes (IG/mL) is quantified by Parallel Line Assay (PLA) method using a virus standard calibrated in infectious titer (PFU/mL) (established using the standard plaque forming unit assay).
This method can measure infectious genomes (IG/mL) for any value of at least $1\cdot10^5$ IG/mL.
Measure of infectious titers using plaque assay on BHK-21 cells is performed as follows:

1. Cells Spreading
Host cells BHK-21 were grown in monolayers in DMEM. At confluency, the cells were washed with 10 mL PBS and then trypsinated. After removing trypsine, cells were then resuspended in 10 mL DMEM with 10% SFV at 37° C.
Then, cells suspension were homogenized and distributed in the multi-well plates (2 mL in each of the 6 wells of the plate). Then, said plates were incubated at 37° C., 5% CO2.

2. Cells Infection
About 1 day after cells spreading, aliquots of virus suspensions were added in each well comprising the BHK-21 cells of step 1. If necessary, said suspensions were firstly diluted serially in PBS, cations 100× and 1% fetal calf serum (FCS), according to method well known by the person skilled in the art. Depending on the case, the virus suspensions which were added to BHK-21 cells of step 1 were either liquid virus-containing compositions before freeze-drying or reconstituted virus-containing composition (i.e after lyophilization, at different time periods and temperatures).
Culture medium was then removed and after stirring during 60 minutes at room temperature, 2 mL of the infection medium (DMEM+5% FCS) were distributed in each well. Plates were then incubated at 37° C., 5% CO2.

3. Cells Fixation
After the medium has been removed, cells were washed with PBS (about 1 mL per well). Then, 1 mL of a solution methanol/acetone (50/50) was added and the resulting mixture was gently stirred at room temperature.
The plates were then let to be dried at room temperature.

4. Detection and Titer Determination
Virus titer determination was performed according to well-known peroxydase reaction using anti-vaccine antibodies and anti-rabbit antibodies combined with peroxydase. More precisely, before reaction anti-vaccine antibodies were diluted 100 times in PBS+2% FCS. Then, 500 µL of said antibodies were added in each well and incubated at 37° C. during about 30 minutes and then washed 3 times with 1 mL PBS+1% Triton X-100.
The reaction with anti-rabbit antibodies combined with peroxydase was carried out in the same manner, except that before reaction, said antibodies are diluted 200 times in PBS+2% FCS.
The DAB solution was prepared by dissolving one commercial DAB tablet in 15 mL of TRIS-HCL 0.05M. Then, the obtained solution was filtrated on a filtration unit NAL-GENE of 2 µm and the resulting filtrated solution was added to 15 µL of aqueous solution of $H_2O_2$ 30%. Once prepared, 1 mL of the DAB solution was added to each well and let until a brown coloration has appeared. The coloration solution was subsequently removed and results are visually interpreted.
Then, the infectious titer was calculated in PFU/mL, using the following formula:

[mean of viral plaques numbers×4]×dilution factor=number of PFU/mL

Each of these methods has similar variability, of about ±0.30 $\log_{10}$ for a single determination. However, variability of both methods decreases when increasing the number of determinations (i.e. the number of replicates tested). For a double determination (use of duplicate samples), a variability of ±0.25 $\log_{10}$ is expected. For a triple determination (use of triplicate samples), a variability of ±0.20 $\log_{10}$ is expected. In alt examples, a single determination has been made when measuring the number of infectious genomes (IG) per mL (IG/mL), while determination of Plaque forming units (PFU) per mL (PFU/mL) has been done in triplicates.

Results

Necessity of a Monovalent Salt

The stability of MVA-MUC1 has been tested in formulations containing Tris-HCl, Na glutamate, sucrose, pH 8.0, and containing either 0 mM or 50 mM of NaCl (see Table 2 above).

Infectious losses after 7, 14, or 28 days at 37° C. are presented in FIG. 1. While none of the two tested formulations is very stable, results clearly show that addition of 50 mM NaCl significantly improves stability at day 14 (about 1 log loss versus almost 2 log loss) and at day 28 (about 3 log loss versus more than 6 log loss).

Therefore, addition of NaCl to the formulation significantly improves stability.

Beneficial Effect of EDTA, a Low Concentration of EtOH or EDTA/EtOH

Figure 2:
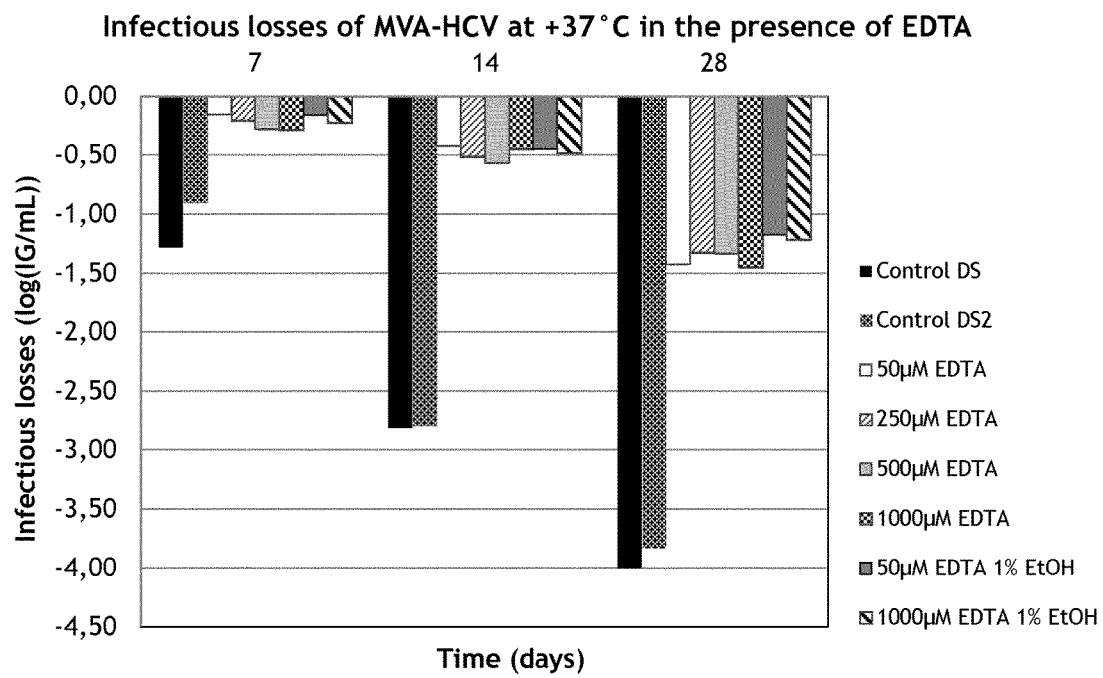
FIG. 2. Beneficial effect of the presence of EDTA or EDTA/EtOH. Infectious losses of MVA-HCV in a control DS formulation containing Tris-HCl 10 mM, sucrose 5% (w/v), Na glutamate 10 mM, NaCl 50 mM, pH 7.5; in a control DS2 formulation containing Tris-HCl 20 mM, sucrose 10% (w/v), Na glutamate 5 mM, NaCl 75 mM, pH 7.5; or in formulations containing Tris-HCl 20 mM, sucrose 10% (w/v), Na glutamate 5 mM, NaCl 75 mM, pH 7.5, and various concentrations of EDTA (50, 250, 500 and 1000 µM) and optionally EtOH 1% v/v after 7, 14 or 28 days at +37° C. Infectious virus have been measured in infectious genomes (IG)/mL, and infectious losses are expressed in log(IG/mL).

The influence of EDTA on stability of MVA-HCV at +37° C. and +5° C. in a formulation containing Tris-HCl, Na glutamate, sucrose, NaCl, pH 7.5 has been tested using various concentrations of EDTA (see Table 3). Results are presented in FIG. 2.

At +37° C. (accelerated stability test), all formulations containing EDTA show less than 1 log infectious loss at 7 and 14 days, and less than 1.5 log infectious loss at 28 days. In marked contrast, formulations without EDTA (control DS and control DS2) showed a very weak stability profile (about 1, 2.5 and 4 log infectious loss at 7, 14 and 28 days, respectively). The concentration of EDTA used (from 50 µM to 1000 µM) does not seem to impact the stabilizing effect. At day 28, formulations containing EtOH in addition to EDTA appear to be further stabilized (see FIG. 2).

Figure 3:
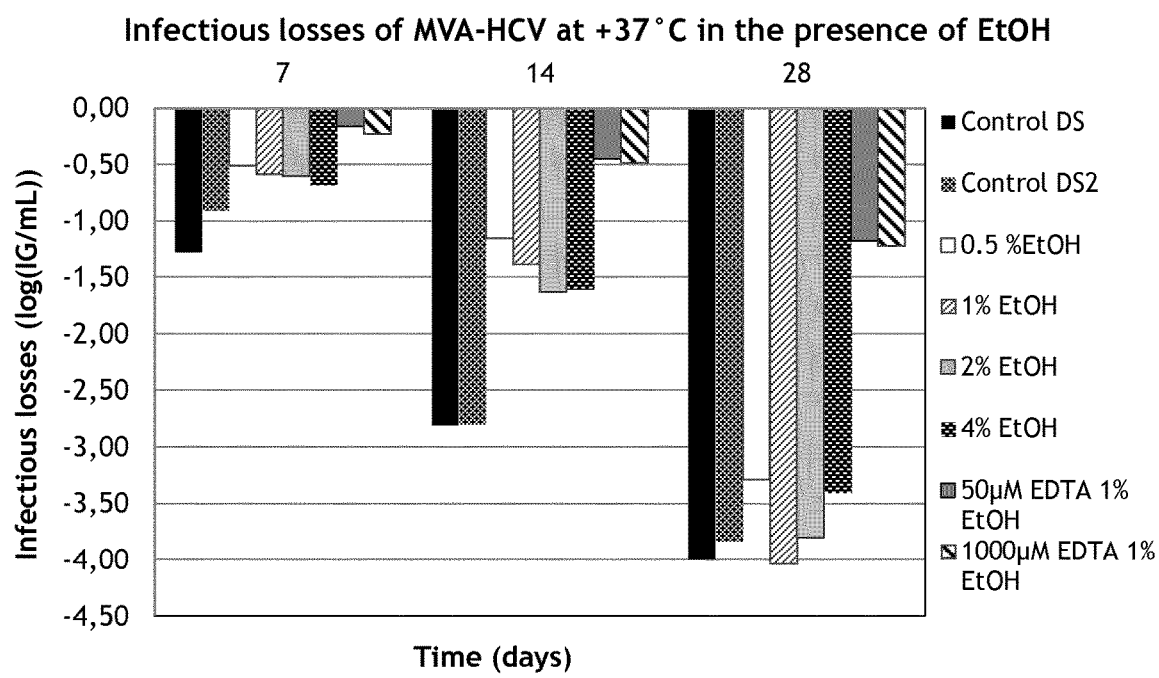
FIG. 3. Beneficial effect of the presence of EtOH or EDTA/EtOH. Infectious losses of MVA-HCV in a control DS formulation containing Tris-HCl 10 mM, sucrose 5% (w/v), Na glutamate 10 mM, NaCl 50 mM, pH 7.5; in a control DS2 formulation containing Tris-HCl 20 mM, sucrose 10% (w/v), Na glutamate 5 mM, NaCl 75 mM, pH 7.5; or in formulations containing Tris-HCl 20 mM, sucrose 10% (w/v), Na glutamate 5 mM, NaCl 75 mM, pH 7.5, and various concentrations of EtOH (0.5; 1; 2 or 4% v/v) and optionally EDTA (50 or 1000 µM) after 7, 14 or 28 days at +37° C. Infectious virus have been measured in infectious genomes (IG)/mL, and infectious losses are expressed in log(IG/mL).

The influence of ethanol (EtOH) on stability of MVA-HCV at +37° C. and +5° C. in a formulation containing Tris-HCl, Na glutamate, sucrose, NaCl, pH 7.5 has been tested using various concentrations of EtOH (see Table 3). Results are presented in FIG. 3. At 37° C. (accelerated stability test), all formulations containing EtOH show significantly lower infectious losses than controls without EtOH at days 7 and 14. In addition, some trend towards a higher stabilization of lower EtOH concentrations can be observed. In marked contrast, formulations without EtOH (control DS and control DS2) showed a very weak stability profile (about 1, 2.5 and 4 log infectious loss at 7, 14 and 28 days, respectively). Moreover, formulations containing EDTA in addition to EtOH show significantly lower infectious losses than those containing only EtOH (see FIG. 3).

Therefore, primary tests using EDTA and EtOH show that both compounds independently increase stability of MVA-HCV in liquid formulations, the stabilizing effect of EDTA being higher than the stabilizing effect of EtOH. Moreover, combination of both compounds further increases stability.

Figure 4A:
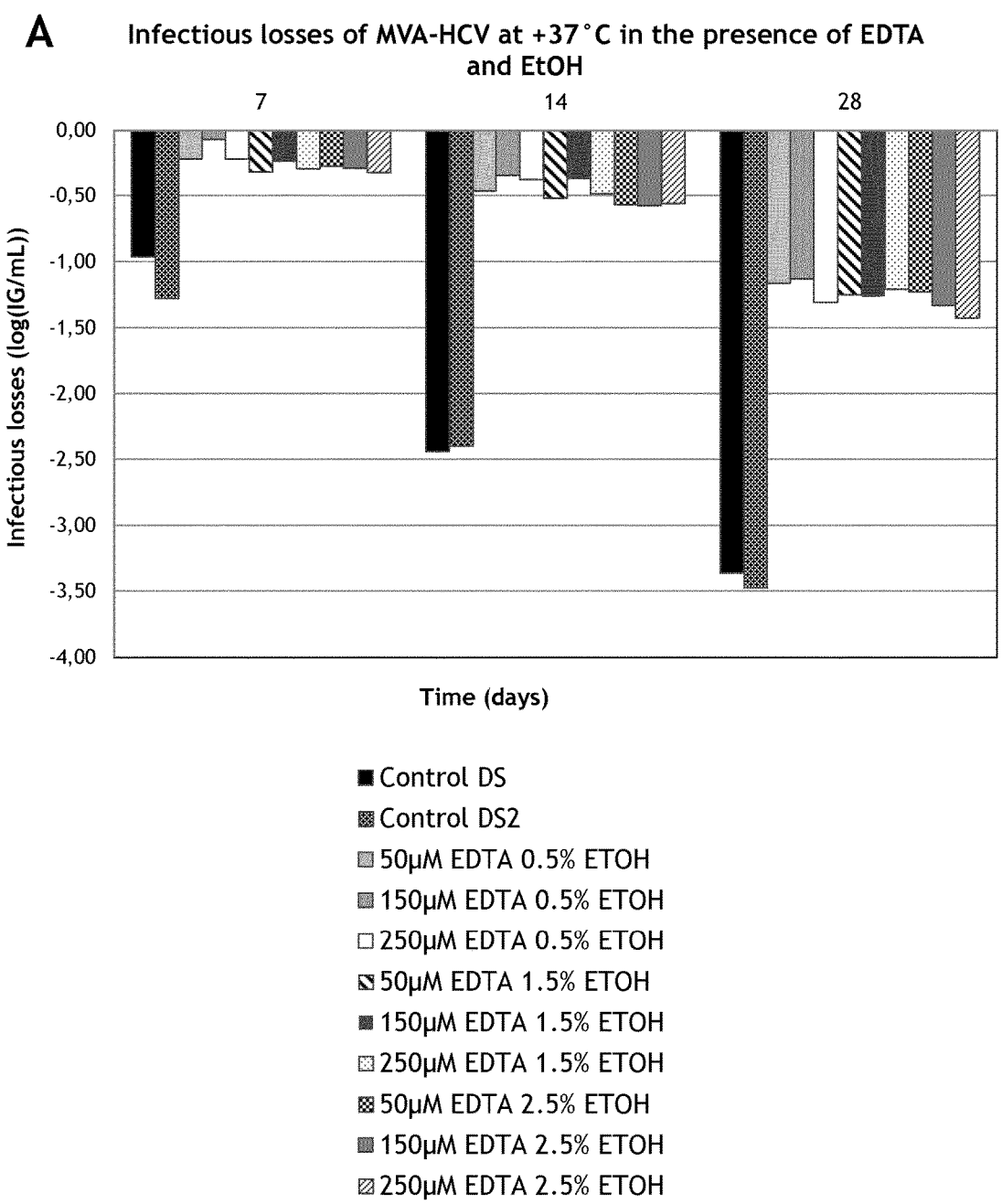
FIG. 4. Beneficial effect of the presence of EDTA/EtOH. Infectious losses of MVA-HCV in a control DS formulation containing Tris-HCl 10 mM, sucrose 5% (w/v), Na glutamate 10 mM, NaCl 50 mM, pH 7.5; in a control DS2 formulation containing Tris-Ha 20 mM, sucrose 10% (w/v), Na glutamate 2.5 mM, NaCl 75 mM, pH 7.5; or in formulations containing Tris-HCl 20 mM, sucrose 10% (w/v), Na glutamate 2.5 mM, NaCl 75 mM, pH 7.5, and various concentrations of EDTA (50, 150, or 250 µM) and EtOH (0.5; 1.5; or 2.5% v/v) (A) after 7, 14 or 28 days at +37° C.; (B) after 28 days, or 2, 3 or 6 months at +25° C.; or (C) after 35 days, or 3, 6, 12, 18, or 24 months at 5° C. Infectious virus have been measured in infectious genomes (IG)/mL, and infectious losses are expressed in log(IG/mL). (D) Desirability curves for EDTA (µM) and EtOH (%) concentrations based on the combined analysis of infectious losses after 7 days at +37° C., infectious losses after 28 days at +37° C., and infectious losses after 24 months at +5° C. Curves representing values of EDTA and EtOH concentrations for which a particular desirability value is obtained are presented. EDTA and EtOH resulting in higher desirability values are preferred.
Figure 4B:
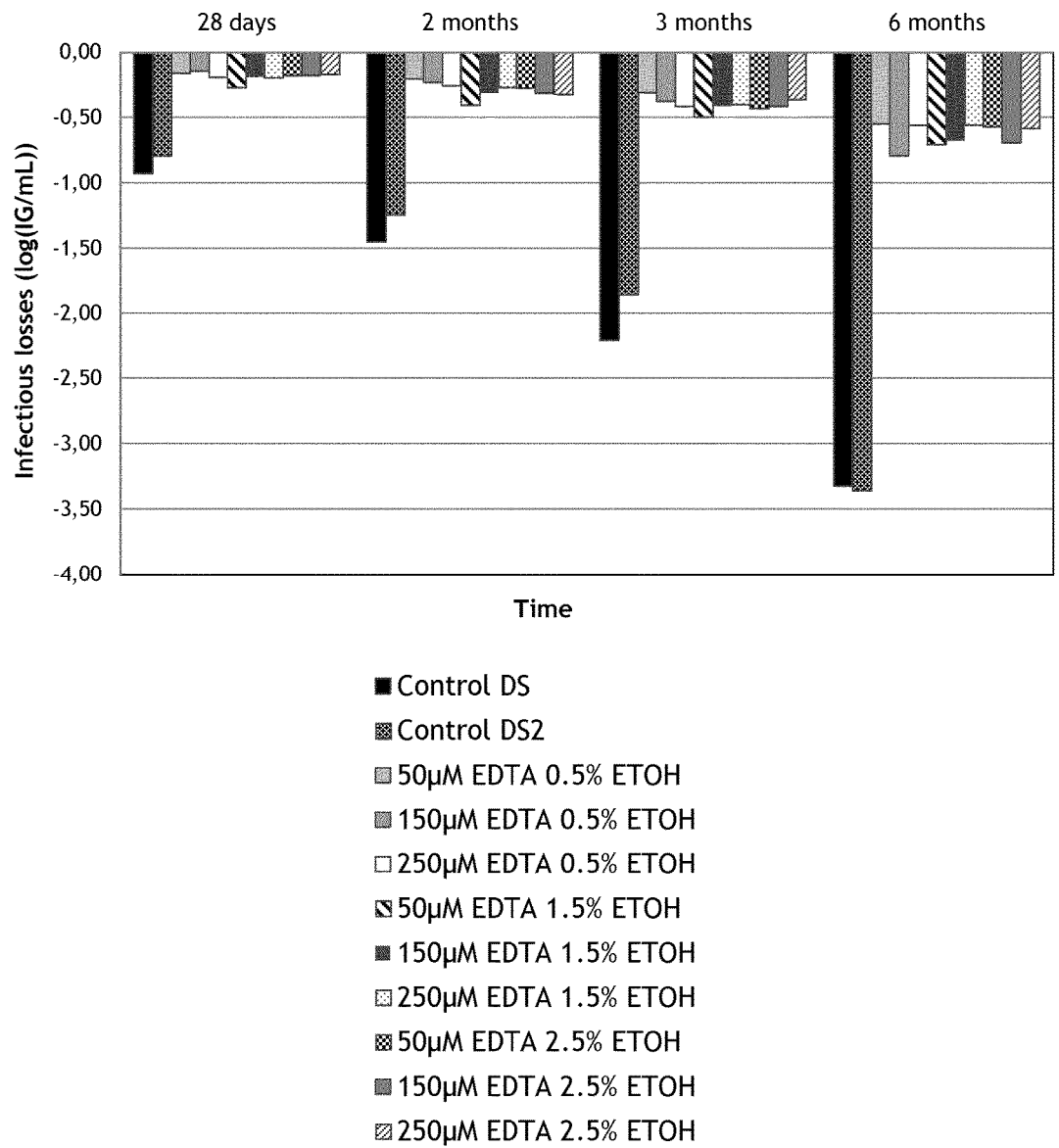
Figure 4C:
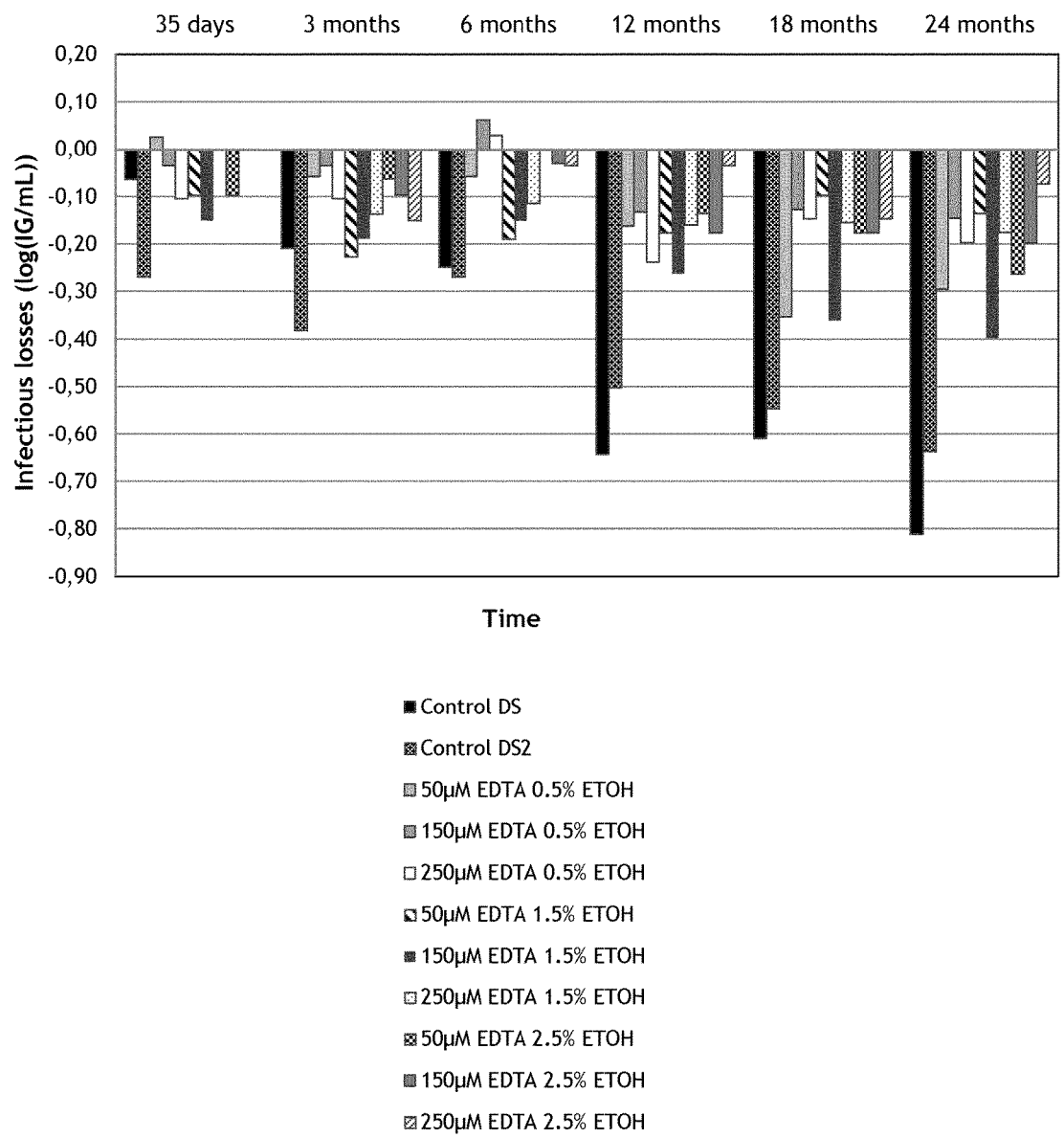

Further experiments were performed to confirm stability of MVA-HCV in formulations containing varying EDTA (50 to 250 µM) and EtOH (0.5 to 2.5%) concentrations (see Table 4) at +37° C., 25° C. and 5° C. Results are presented in FIGS. 4A, 4B and 4C. At all tested temperatures, good stability was observed for all formulations. In particular, for all formulations containing EDTA and EtOH, infectious losses were close to 1 log after 28 days at 37° C. (see FIG. 4A), and infectious losses were lower than 0.3 after 12 months at +5° C. At +5° C., most formulations containing EDTA and EtOH further show infectious losses lower than 0.3 $\log_{10}$ after 18 and 24 months. In contrast, the stability of control DS and DS2 formulations without EDTA and EtOH decreased very rapidly, especially at 37° C. and 25° C. (e.g. about 1 log infectious loss at 7 days at 37° C. and 28 days at 25° C.).

Figure 4D:
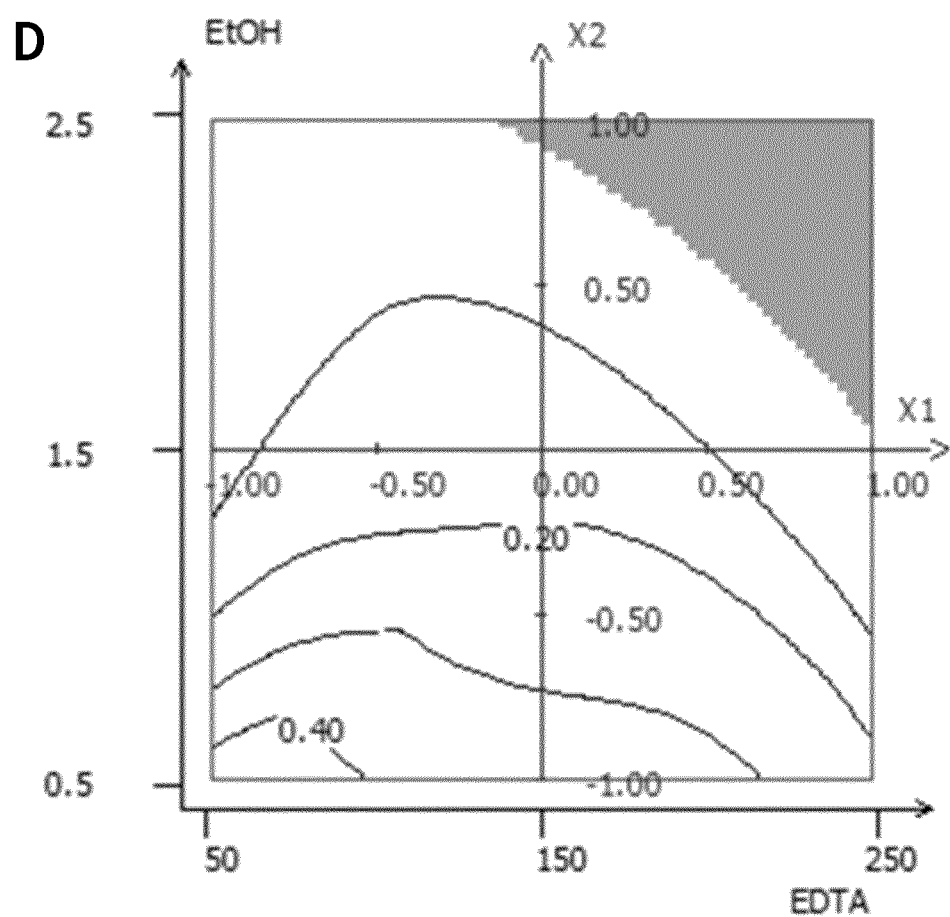

Another representation of the results obtained at +37° C. and +5° C. is presented in FIG. 4D, by using matrix of experiment to define the design space of the formulation according the amounts of EDTA and Ethanol, in order to define optimal EDTA and EtOH concentrations, based on results obtained both at +37° C. (at days 7 and 28) and +5° C. (at 24 months). In this figure, EDTA concentration (µM) is represented as x-axis and EtOH concentration (%) as y-axis. Curves corresponding to desirability of the formulation are then represented in this 2-dimensional area, the higher the value of the desirability, the better is the formulation.

FIG. 4D shows that the best formulations are obtained for 50-150 µM EDTA and 0.5-1% v/v EtOH.

Based on this analysis, an optimal formulation using 150 µM EDTA and 0.5% v/v EtOH was defined.

Beneficial Effect of a Low Concentration of Sodium Glutamate

The influence of Na glutamate on stability of MVA-HCV at +37° C. and +25° C. in a formulation containing Tris-HCl, Na glutamate, sucrose, NaCl, pH 7.5 has been tested with or without various concentrations of Na glutamate from 0 to 10 mM (see Table 5). Results are presented in FIGS. 5A, 5B and 5C respectively.

At +37° C., the three formulations containing at least 5 mM of Na glutamate show infectious losses lower than 1 at day 28, while the two formulations containing 0 mM or 2.5 mM of Na glutamate have infectious losses higher than but close to 1. This shows that Na glutamate does not have high stabilizing effect, but that a low concentration of Na glutamate, between 5 and 10 mM, may have a minor stabilizing effect. In addition, FIG. 5A suggests that the optimal concentration is around 5 mM, since formulations with Na glutamate at 7.5 and 10 mM have slightly lower stability than the formulation with Na glutamate at 5 mM (FIG. 5A).

At +25° C., infectious losses at 12 months confirm that Na glutamate has a small stabilizing effect, and that a concentration of about 5 mM is optimal (FIG. 5B).

At +5° C., infectious losses from 12 months to 30 months confirm that Na glutamate has a small stabilizing effect, and that a concentration of about 5 mM is optimal (FIG. 5C). Results obtained at +5° C. show infectious losses so small at 12 months that it is difficult to demonstrate a beneficial effect of Na glutamate. In fact, the presence in the formulations of other compounds, in particular EDTA and EtOH, might explain the stabilizing effect, and a small effect of Na glutamate is difficult to evidence at this low temperature. However, this does not contradict the small effect and the optimal concentration of about 5 mM observed at higher temperatures of +25 and +37° C.

Beneficial Effect of a Low Concentration of Sucrose

The influence of sucrose on stability of MVA-MUC1 at +37° C. in a formulation containing Tris-HCl, Na glutamate, sucrose, NaCl, pH 8.0 has been tested with various concentrations of sucrose (see Table 6). Results are presented in FIG. 6, and show that the concentration of sucrose does not significantly impact the level of stability.

No Beneficial Effect and Even Deleterious Effect of Polysorbate 80 or Polysorbate 40

The influence of polysorbate 80 or polysorbate 40 on stability of MVA-HPV at +25° C. and +5° C. in a formulation containing Tris-HCl, Na glutamate, sucrose, NaCl, pH 7.5 (see Table 7) has been tested using various concentrations of polysorbate 80 or polysorbate 40 shown to have stabilizing effect on other viruses (see EVANS et al. J Pharm Sci. 2004 October, 93(10):2458-75, U.S. Pat. No. 7,456,009, SHI et al. J Pharm Sci. 2005 July, 94(7):1538-51, US2007/0161085). Results are presented in FIGS. 7A and 7B.

At +25° C. and +5° C., no concentration of polysorbate permits to increase stability compared to control formulation without polysorbate, so that no stabilizing effect is observed.

In contrast, at both temperatures, for concentrations of polysorbate of at least 0.02% v/v, a destabilizing effect can be noted, which increases with the concentration of polysorbate used. At +5° C., even the very low concentration of 0.005% v/v results in some destabilizing effect.

It must therefore be concluded that polysorbate does not have stabilizing effect, and that concentrations of at least 0.02% v/v rather have destabilizing effect. Polysorbate should thus preferably be excluded or present at very low concentrations in liquid formulations of vaccinia virus.

Similarly, stability of a vaccinia virus Wyeth strain produced in a human continuous cell line and purified by a method that involves at least one step of treatment with at least one protease, in a control formulation containing Tris-HCl 30 mM, sucrose 10% (w/v), or in a formulation further containing 150 μg/mL polysorbate 80 was tested after 7, 14, 21, or 28 days at +37° C. Results are presented in FIG. 7C and clearly show that, for this vaccinia virus strain also, polysorbate does not have a positive effect on stability.

No Beneficial Effect and Even Deleterious Effect at High Concentrations of $MgCl_2$ The influence of $MgCl_2$ on stability of MVA-MUC1 at +37° C. during 14 days in a formulation containing Tris-HCl, Na glutamate, sucrose, NaCl, pH 8.0 (see Table 8) has been tested with or without various concentrations of $MgCl_2$ shown to have stabilizing effect on other viruses (see EVANS et al. J Pharm Sci. 2004 October, 93(10):2458-75 and U.S. Pat. No. 7,456,009). Results are presented in FIG. 8 and clearly show that $MgCl_2$ has no beneficial effect on MVA stability even have deleterious effects on MVA stability at concentrations of at least 0.5M.

$MgCl_2$ should thus preferably be excluded or present at low concentrations in liquid formulations of vaccinia virus.

This is all the more true because optimized formulations according to the invention contain a chelating agent (in particular a divalent cations chelating agent and, more preferably EDTA), which may thus interfere with any low beneficial effect of $MgCl_2$ on poxviruses, and more particularly vaccinia viruses, stability.

Further evidence of deleterious effect of $MgCl_2$ in formulations according to the invention is presented in Example 5 below (see also FIG. 16).

Similarly, stability of a vaccinia virus Wyeth strain produced in a human continuous cell line and purified by a method that involves at least one step of treatment with at least one protease, in a control formulation containing Tris-HCl 30 mM, sucrose 10% (w/v), or in a formulation further containing 1000 mM (1M) $MgCl_2$ was tested after 7 or 14 days at +37° C. Results are presented in FIG. 8B and clearly show that, for this vaccinia virus strain also, $MgCl_2$ does not have a positive effect on stability.

No Beneficial Effect and Rather Deleterious Effect of Arginine

The influence of arginine on stability of MVA-MUC1 at +37° C. in a formulation containing Tris-HCl, Na glutamate, sucrose, NaCl, pH 8.0 (see Table 9) has been tested with or without various concentrations of arginine shown to have stabilizing effect on other viruses (see US2007/0161085). Results are presented in FIG. 9 and clearly show that arginine has no beneficial effect on MVA stability. In contrast, after 28 days at 37° C., the presence of arginine is rather deleterious, in particular at high concentration.

Arginine should thus preferably be excluded or present at very low concentrations in liquid formulations of vaccinia virus.

Similarly, stability of a vaccinia virus Wyeth strain produced in a human continuous cell line and purified by a method that involves at least one step of treatment with at least one protease, in a control formulation containing Tris-HCl 30 mM, sucrose 10% (w/v), or in a formulation further containing 50 mM arginine was tested after 7, 14, 21, or 28 days at +37° C. Results are presented in FIG. 9B and clearly show that, for this vaccinia virus strain also, arginine does not have a positive effect on stability.

No Beneficial Effect of a Mixture of Amino Acids

The influence of a mixture of amino acids on stability of MVA-MUC1 at +37° C. and +25° C. in a formulation containing Tris-HCl, Na glutamate, sucrose, NaCl, pH 8.0 (see Table 10) has been tested with or without said mixture of amino acids. Results are presented in FIG. 10 and clearly show that the presence of a mixture of amino acids has no significant effect on MVA stability.

While a mixture of amino acids may be present in liquid formulations of vaccinia virus, it is clearly not essential and does not need to be present.

No Beneficial Effect and Rather Deleterious Effect of Histidine

The influence of histidine on stability of MVA-HPV at +25° C. and +5° C. in a formulation containing Tris-HCl, Na glutamate, sucrose, NaCl, pH 7.5 has been tested with or without 10 mM histidine (see Table 11), a concentration shown to have stabilizing effect on other viruses (see EVANS et al. J Pharm Sci. 2004 October, 93(10):2458-75, U.S. Pat. No. 7,456,009, US2007/0161085, U.S. Pat. No. 7,914,979, WO2014/029702, WO2014/053571).

Figure 11A:
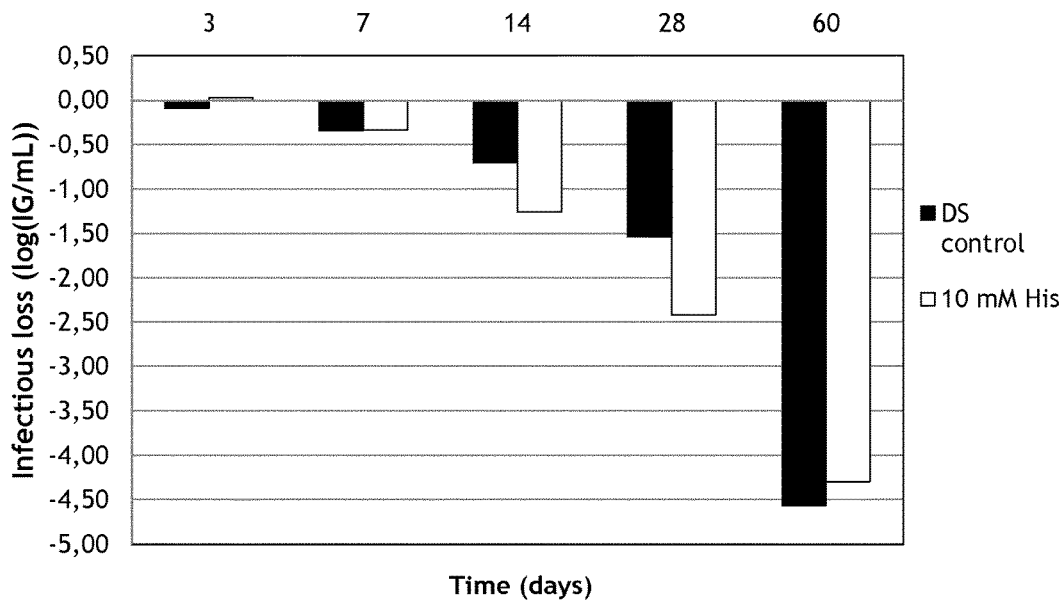
Figure 11B:
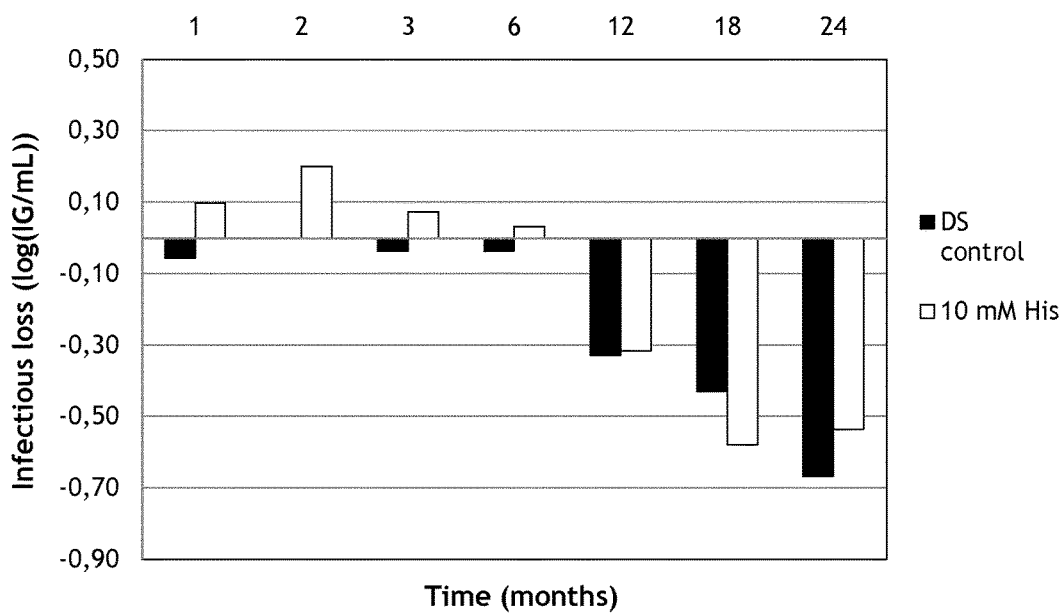

Results are presented in FIGS. 11A and 11B.

No stabilizing effect of histidine has been observed at +25° C. or at 5° C. In contrast, a trend towards a destabilizing effect can be observed at both temperatures.

Histidine should thus preferably be excluded or present at very low concentrations in liquid formulations of vaccinia virus.

Conclusions

The above results clearly show that:

The following compounds have significant beneficial effect on vaccinia virus stability in a liquid formulation:
Monovalent salts such as NaCl.
Disaccharides such as sucrose at low percentages. Such components are cryoprotectant and are thus believed to protect the vaccinia virus at low storage temperature, such as at about +5° C. In addition, such compounds increase viscosity of the liquid formulation, which might limit interactions between vaccinia virus and potentially deleterious compounds.
EDTA, which has a strong stabilizing effect.
Ethanol, which has a significant stabilizing effect, although less than EDTA.

A combination of EDTA and ethanol, this combination providing further stabilizing effect compared to each compound alone.

One or more of these compounds may thus be present in stable liquid vaccinia virus formulations.

In particular, the above results show that a buffered liquid formulation containing sucrose, a monovalent salt and EDTA, and preferably also containing ethanol, shows particularly good stability.

The following compounds have no significant beneficial effect but no deleterious effect on vaccinia virus stability in a liquid formulation:

Na glutamate. While this compound is not essential to stability, a low concentration may have a small stabilizing effect on MVA.

A mixture of amino acids. While this compound is not essential to stability, a low concentration may have a small stabilizing effect on MVA.

Such compounds may or not be present in formulations according to the invention.

The following compounds have no beneficial effect at low concentration and deleterious effect at higher concentration on vaccinia virus stability in a liquid formulation, and should thus preferably be absent or present at very low concentrations in stable liquid vaccinia virus formulations:

Surfactants such as polysorbate. At low concentrations, no effect is observed. However, at concentrations of at least 0.02% v/v, a destabilizing effect increasing with polysorbate concentration is observed.

Histidine: at 10 mM, a weak destabilizing effect may be observed.

$MgCl_2$: at 0.5 or 1 M, or even at 75 mM (see Example 5 below), a destabilizing effect is observed, Arginine: a weak destabilizing effect is observed at concentrations of at least 30 mM and destabilization increases with arginine concentration.

Example 2: Influence of pH on MVA Virus Stability

The influence of the pH of the liquid formulation on vaccinia virus stability has been tested, in order to determine a suitable pH range for stable liquid formulations.

Materials and Methods

MVA Viruses

The MVA virus used was MVA-HCV (TG4040), a recombinant MVA virus expressing nonstructural HCV proteins (NS3, NS4 and NS5B) from HCV genotype 1 b strain ja (see WO2004/111082), which was diluted to an initial target concentration of $4$-$8 \ 10^7$ IG/mL. MVA-HCV was produced in chicken embryo fibroblast (CEF), and recovered and purified by a method comprising recovery of infected CEF culture, breakage of cells by mechanical means, and various purification steps that do not involve any step of treatment with a protease.

Tested Formulations

Tested formulations are represented in Table 12 below:

TABLE 12

| Formulations tested with varying pH | | | | | |
|---|---|---|---|---|---|
| | pH 6.0 | pH 7.0 | pH 7.5 | pH 8.0 | pH 9.0 |
| Tris-HCl (mM) | 20 | 20 | 20 | 20 | 20 |
| Na Glutamate (mM) | 5 | 5 | 5 | 5 | 5 |

TABLE 12-continued

| Formulations tested with varying pH | | | | | |
|---|---|---|---|---|---|
| | pH 6.0 | pH 7.0 | pH 7.5 | pH 8.0 | pH 9.0 |
| Sucrose (% w/v) | 10 | 10 | 10 | 10 | 10 |
| NaCl (mM) | 75 | 75 | 75 | 75 | 75 |
| EDTA (µM) | 150 | 150 | 150 | 150 | 150 |
| EtOH (% v/v) | 0.5 | 0.5 | 0.5 | 0.5 | 0.5 |
| pH | 6.0 | 7.0 | 7.5 | 8.0 | 9.0 |

Analysis of Stability

Analysis of stability was done as described in Example 1.

Measure of Infectious Titers

Measure of infectious titers was done as described in Example 1.

Results

The influence of pH on stability of MVA-HCV at +37° C. and +5° C. in a formulation containing Tris-HCl, Na glutamate, sucrose, NaCl, EDTA and ethanol has been tested at various pH values. Results are presented in FIGS. 12A and 12B.

At +37° C. (FIG. 12A), it is clear already after 7 days that it is important that pH be comprised between more than 6 and less than 9. In particular, good results are obtained when the pH is comprised between 7 and 8.

At +5° C. also (FIG. 12B), results at 12 months suggest it is better that pH be comprised between more than 6 and less than 9. In particular, good results are obtained when the pH is comprised between 7 and 8.

Conclusions

The above results show that pH of a liquid formulation of vaccinia virus should preferably be comprised between more than 6 and less than 9. In particular, good results are obtained when the pH is comprised between 7 and 8. A pH comprised between 6.5 and 8.5 might thus be acceptable.

Example 3: Influence of MVA Virus Initial Titer on Stability

Then influence of vaccinia virus initial titer on subsequent stability in a liquid formulation was also tested.

Materials and Methods

MVA Viruses

The MVA virus used was MVA-HCV (TG4040), a recombinant MVA virus expressing nonstructural HCV proteins (NS3, NS4 and NS5B) from HCV genotype 1 b strain ja (see WO2004/111082), which was diluted to varying initial target concentrations: $1.0 \cdot 10^8$ PFU/mL, $5.0 \ 10^7$ PFU/mL, $1.0 \ 10^7$ PFU/mL, and $5.0 \ 10^6$ PFU/mL.

MVA-HCV was produced in chicken embryo fibroblast, and recovered and purified by a method comprising recovery of infected CEF culture, breakage of cells by mechanical means, and various purification steps that do not involve any step of treatment with a protease.

Tested Formulations

Tested formulations are represented in Table 13 below:

TABLE 13

| Formulations tested with varying MVA initial titers | | |
|---|---|---|
| | Control DS | Invention |
| Tris-HCl (mM) | 10 | 20 |
| Na Glutamate (mM) | 10 | 2.5 |
| Sucrose (% w/v) | 5 | 10 |

TABLE 13-continued

Formulations tested with varying MVA initial titers

|  | Control DS | Invention |
|---|---|---|
| NaCl (mM) | 50 | 75 |
| EDTA (mM) | 0 | 150 |
| EtOH (% v/v) | 0 | 0.5 |
| pH | 7.5 | 7.5 |

Analysis of Stability

Analysis of stability was done as described in Example 1.

Measure of Infectious Titers

Measure of infectious titers was done as described in Example 1.

Results

Evolution of infectious losses of MVA-HCV at varying initial titers at +37° C., +25° C. and +5° C. are presented in FIGS. 13A, 13B and 13C respectively.

At +37° C., infectious titers of all formulations according to the invention were lower than 1 log after 7 days. However, a trend towards higher stability of formulations with higher initial MVA-HCV titer may be observed. At day 14, infectious titers of all formulations according to the invention excepted the formulation containing an initial MVA-HCV titer of $5.0\ 10^6$ PFU/mL were still lower than 1 log, but a clear trend of higher stability of formulations with higher initial MVA-HCV titer is observed. This observation is confirmed at day 28, only formulations according to the invention containing an initial MVA-HCV titer of $5.0\ 10^7$ PFU/mL or $1.0\ 10^8$ PFU/mL showing a infectious loss lower than 1 log (FIG. 13A).

The same type of observations can be made at +25° C. (FIG. 13B). However, the difference of stability of formulations according to the invention depending on MVA-HCV initial titer rather distinguish two subfamilies: the three formulations with at least $1.0\ 10^7$ PFU/mL (which show less than 1 log loss of infectious titer at 7 months) and the only formulation with less than $1.0\ 10^7$ PFU/mL ($5.0\ 10^6$ PFU/mL, which shows more than 1 log loss of infectious titer at 7 months, and already shows almost 1 log loss of infectious titer at 3 months).

At +5° C., the difference of stability of formulations according to the invention depending on MVA-HCV initial titer distinguishes the same two subfamilies as at 25° C. (FIG. 13C): the three formulations with at least $1.0\ 10^7$ PFU/mL (which show less than 0.2 log loss of infectious titer at 18 months) and the only formulation with less than $1.0\ 10^7$ PFU/mL ($5.0\ 10^6$ PFU/mL, which shows more than 0.5 log loss of infectious titer already at 12 months, and more than the defined limit of 0.3 log already at 2 months).

Conclusions

In view of the above results, it appears that an initial titer of at least $1.0\ 10^7$ PFU/mL is highly preferable for guaranteeing stability of a liquid formulation of MVA.

Example 4: Stability of Various Vaccinia Virus Strains

In order to confirm the stability of optimized formulations defined in previous examples, such optimized formulations were tested on various vaccinia virus strains, in two distinct experiments.

Materials and Methods

Viruses

The following vaccinia viruses were used:

Experiment 1:
  MVA-MUC1 (TG4010), a recombinant MVA virus expressing MUC1 tumor associated antigen and interleukin 2 (see WO92/07000 and WO95/09241), which was diluted to an initial target concentration of 5 to $8\ 10^8$ IG/mL.
  MVA-HCV (TG4040), a recombinant MVA virus expressing nonstructural HCV proteins (NS3, NS4 and NS5B) from HCV genotype 1 b strain ja (see WO2004/111082), which was diluted to an initial target concentration of 4 to $6\ 10^7$ IG/mL.
  MVA-HPV (TG4001), a recombinant MVA virus expressing human papillomavirus E6 and E7 antigens and interleukin 2 (see WO90/10459, WO95/09241, WO98/04705, WO99/03885, WO2007/121894), which was diluted to an initial target concentration of 2 to $3\ 10^8$ IG/mL.
  The three MVA viruses were produced in chicken embryo fibroblast, and recovered and purified by a method comprising recovery of infected CEF culture, breakage of cells by mechanical means, and various purification steps that do not involve any step of treatment with a protease.

Experiment 2:
  MVA-HCV (TG4040), a recombinant MVA virus expressing nonstructural HCV proteins (NS3, NS4 and NS5B) from HCV genotype 1 b strain ja (see WO2004/111082), produced in:
    chicken embryo cells (MVA-HCV/CEC) (initial target titer of 2.5 to $3\ 10^7$ IG/mL), or
    an immortalized duck embryonic cell line (MVA-HCV/duck cell line) (initial target titer of 3 to $4\ 10^7$ IG/mL),
  MVA-FCU1 (TG4023), a recombinant MVA virus expressing a fusion protein with cytosine deaminase activity 1 (see WO99/54481), produced in chicken embryo cells (MVA-FCU1/CEC) (initial target titer of 1 to $1.5\ 10^8$ IG/mL),
  Copenhagen-FCU1 (TG6002), a recombinant vaccinia virus strain Copenhagen, expressing a Fan fusion protein with cytosine deaminase activity and comprising a defective I4L and a defective J2R gene (see WO2009/065546 and WO2009/065547) produced in chicken embryo cells (Copenhagen-FCU1/CEC) (initial target titer of 2 to $3.0\ 10^8$ IG/mL). Methods used for production/purification of MVA-HCV/CEC, MVA-HCV/duck cell line, MVA-FCU1/CEC, and Copenhagen-FCU1/CEC viruses did not comprise any step with addition of a protease enzyme.

Experiment 3:
  A recombinant vaccinia virus of strain Wyeth, produced in a human continuous cell line and purified by a method that involves at least one step of treatment with at least one protease (VV Wyeth) was also used, at an initial target titer of 5 to $8\ 10^8$ PFU/mL.

Tested Formulations

Experiment 1:

Tested formulations for MVA viruses are represented in Table 14 below:

TABLE 14

Formulations tested for 3 MVA viruses.

|  | Control DS | Invention |
|---|---|---|
| Tris-HCl (mM) | 10 | 20 |
| Na Glutamate (mM) | 10 | 5 |

TABLE 14-continued

Formulations tested for 3 MVA viruses.

|  | Control DS | Invention |
|---|---|---|
| Sucrose (% w/v) | 5 | 10 |
| NaCl (mM) | 50 | 75 |
| EDTA (µM) | / | 150 |
| EtOH (% v/v) | / | 0.5 |
| pH | 7.5 or 8.0* | 7.5 |

*pH 7.5 for MVA-HPV and pH 8.0 for MVA-HCV and MVA-MUC1

Experiment 2:

Tested formulations for MVA-HCV/CEC, MVA-HCV/duck cell line, MVA-FCU1/CEC, and Copenhagen-FCU1/CEC viruses are represented in Table 15A below:

TABLE 15A

Formulations tested for MVA-HCV/CEC, MVA-HCV/cell line, MVA-FCU1/CEC, and Copenhagen-FCU1/CEC viruses.

|  | Control | Formulated |
|---|---|---|
| Tris-HCl (mM) | 10 | 20 |
| Na glutamate (mM) | 10 | 5 |
| Sucrose (% w/v) | 5 | 10 |
| NaCl (mM) | 50 | 75 |
| EDTA (µM) | / | 150 |
| EtOH (% v/v) | / | 0.5 |
| pH | 8.0 | 7.5 |

Experiment 3:

Tested formulations for VV Wyeth virus are represented in Table 156 below:

TABLE 15B

Formulations tested for VV Wyeth virus.

|  | Control | Formulation 1 | Formulation 2 |
|---|---|---|---|
| Tris-HCl (mM) | 30 | 30 | 30 |
| Sucrose (% w/v) | 10 | 10 | 10 |
| NaCl (mM) | 0 | 200 | 500 |
| EDTA (µM) | 0 | 150 | 150 |
| EtOH (% v/v) | 0 | 0.5 | 0.5 |
| pH | 7.5 | 7.5 | 7.5 |

Analysis of Stability

Analysis of stability was done as described in Example 1.

Measure of Infectious Titers

Measure of infectious titers was done as described in Example 1.

Results

Figure 14A:
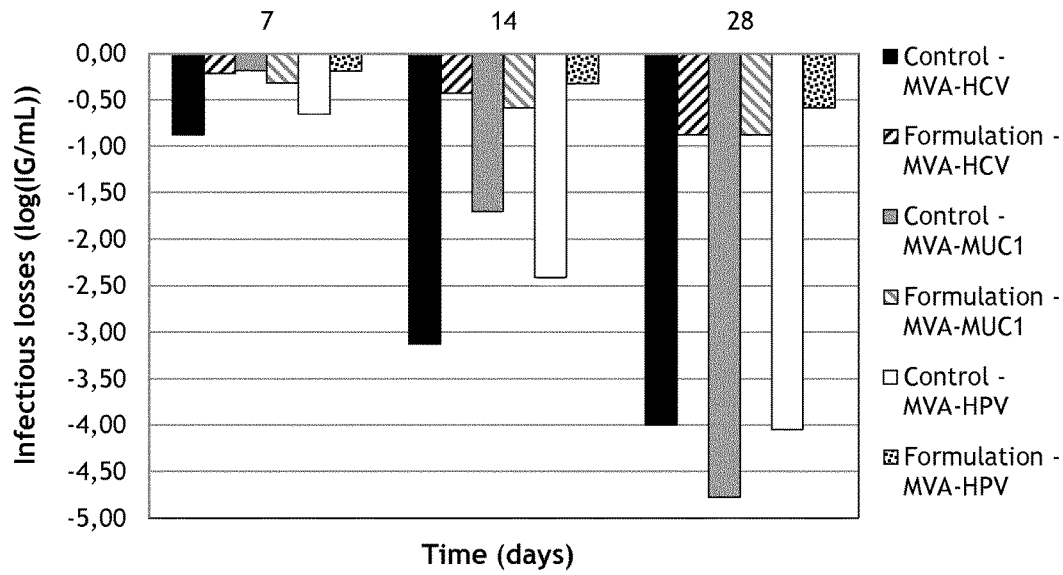
Figure 14B:
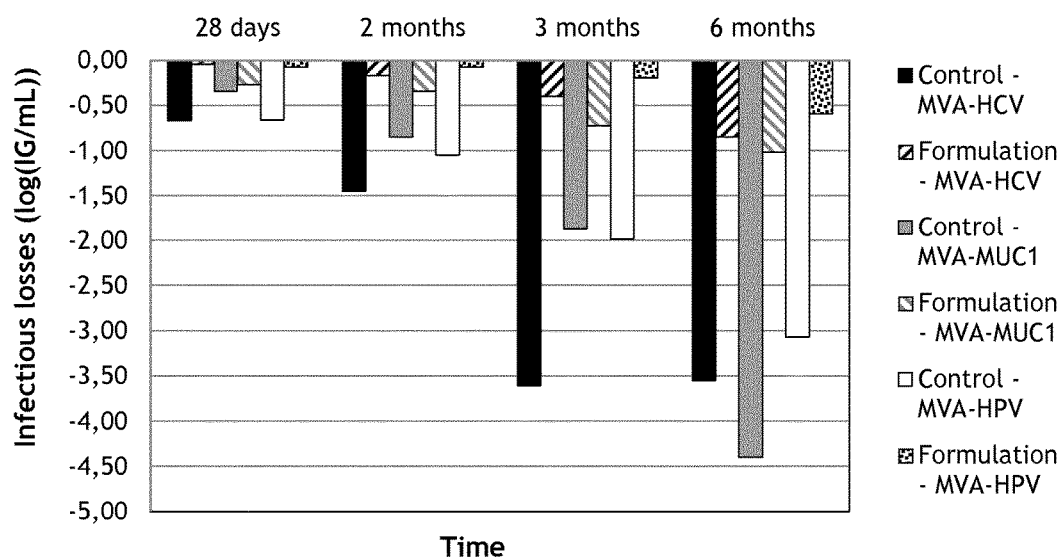
Figure 14C:
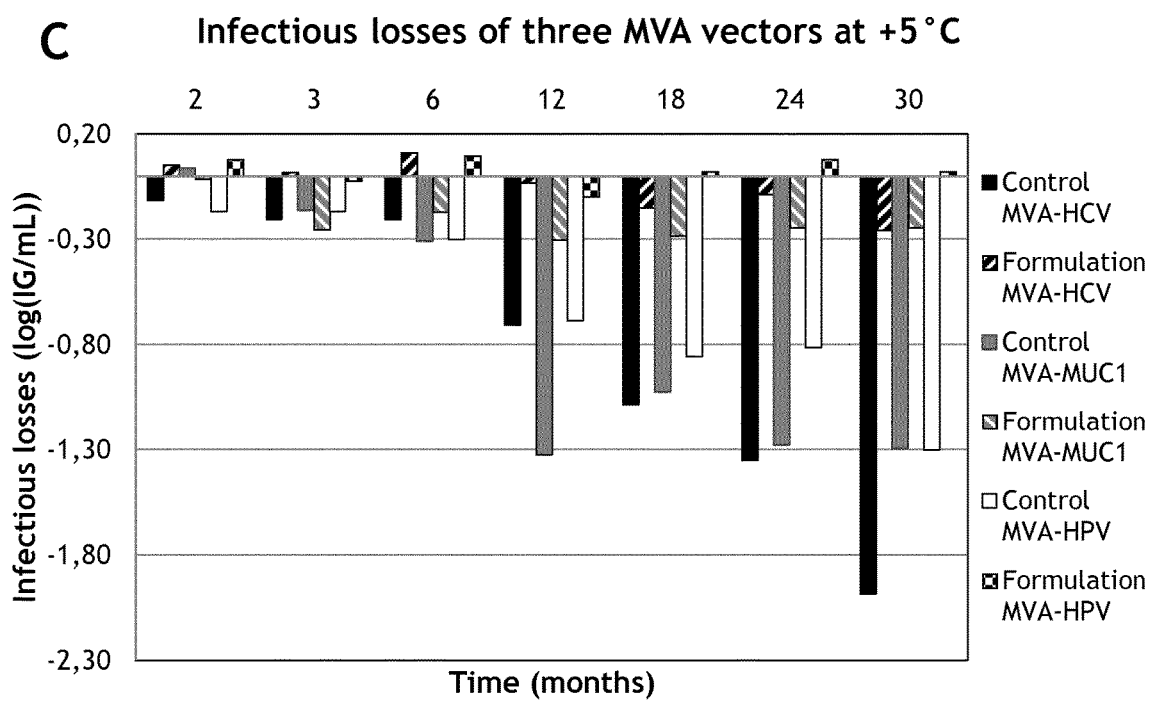

Experiment 1:

Stability of the three MVA viruses in the optimized formulation of the invention at +37° C., +25° C. and +5° C. is presented in FIGS. 14A, 14B and 14C respectively.

At +37° C., all three MVA vectors showed less than 1 log loss of infectious titer at day 28, thus showing very good stability at this elevated temperature.

At +25° C., all three MVA vectors also showed less than 1 log loss of infectious titer at 6 months, thus also showing very good stability at this temperature.

Finally, all three MVA vectors also showed less than 0.3 log loss of infectious titer after 30 months at +5° C., thus showing very high stability at this targeted storage temperature.

While some minor variations may be observed depending on the MVA vector used, the above results clearly show that the optimized formulation designed in preceding examples is applicable to any MVA vector, no matter what is/are the heterogeneous sequences inserted into it.

Experiment 2:

In this second experiment, the same formulation previously optimized for MVA was tested on several MVA viruses obtained by various methods, and on another vaccinia virus strain: Copenhagen (vector TG6002).

Results are presented in FIG. 15A, and show that the tested formulation according to the invention, which had been optimized on MVA viruses, also permits stabilization of other vaccinia virus strains, such as Copenhagen. In particular, less than 1 log loss is observed at day 14 for all tested viruses.

The less stabilized virus is MVA-HCV/CEC. This may be explained by the fact that this virus is the virus used at the lowest initial titer.

Experiment 3:

In this third experiment, the same formulation previously optimized for MVA was tested on another strain of vaccinia virus (Wyeth strain), which had been produced in a human continuous cell line and purified by a method that involves at least one step of treatment with at least one protease.

Figure 15B:
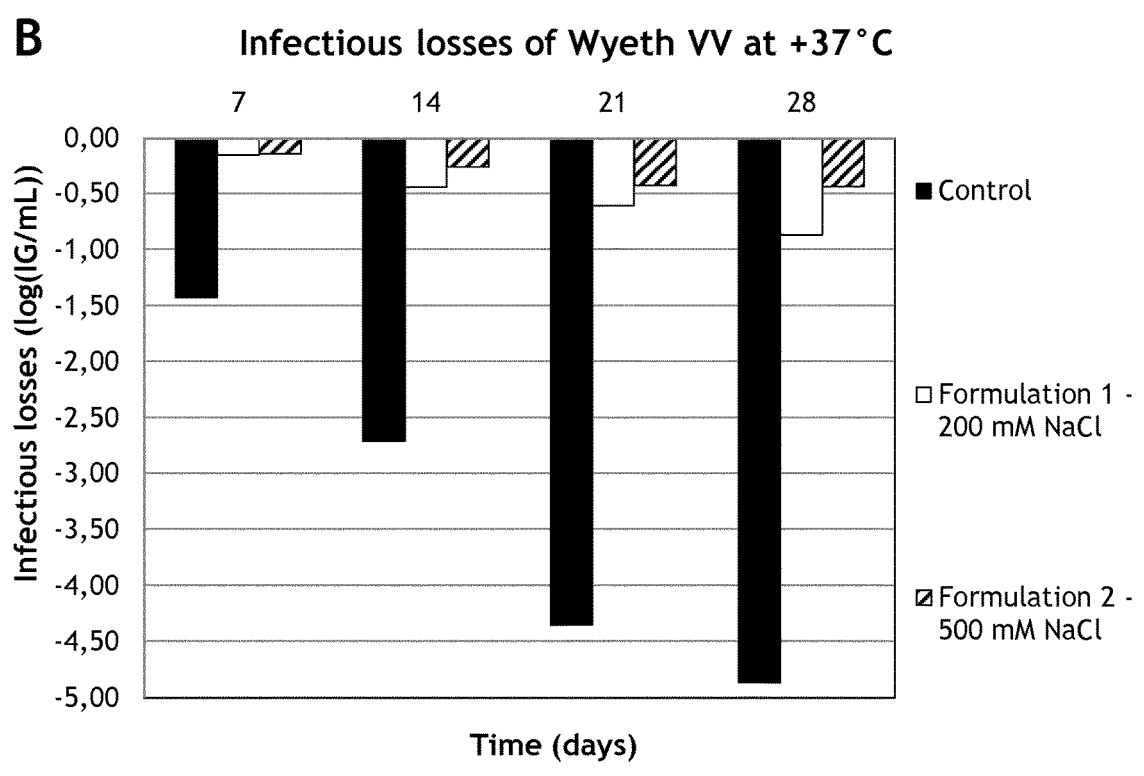

Results are presented in FIG. 15B, and show that the tested formulation according to the invention, which had been optimized on MVA viruses, also permits stabilization of the Wyeth vaccinia virus strain, despite the potential residual presence of some protease in the virus environment. In particular, less than 1 log loss is observed at day 28.

It should also be noted that, in the context of a virus environment that may contain some residual protease, increasing the monovalent salt (NaCl) from 200 to 500 mM further increases stability of the virus.

Conclusions

The above results clearly demonstrate that the optimized formulations designed by the inventors are applicable to various vaccinia viruses strains, and that the heterogeneous constructions that may be inserted in such viruses do not significantly influence the stabilization provided by the optimized formulations according to the invention.

The above results also show that optimized formulations designed by the inventors are applicable even when the purification process involves treatment with at least one protease and thus when the virus environment may contain residual protease. In this particular case, increasing the monovalent salt concentration of the formulation over 200 mM further improves stability.

Example 5: Substitution of Preferred Compounds by Compounds of the Same Family or Other Families In order to confirm whether the individual compounds tested before could be replaced by other compounds of the same family of or other families, an experiment was performed, in which each of the previously tested individual compounds of an optimized formulation was replaced by a compound of the same family of or other families:

Buffer: previously tested buffer Tris-HCl was replaced by Tricine or HEPES Buffer at the same concentration of 20 mM. Both replacement buffer also have buffering capacity between pH 7 and pH 8.

Salt: previously tested monovalent salt NaCl was replaced either by another monovalent salt (KCl) or by a divalent salt ($MgCl_2$) at the same concentration of 75 mM.

Disaccharide or sugar alcohol: previously tested disaccharide sucrose was replaced either by another disaccharide (trehalose) or by a sugar alcohol (mannitol) at the same concentration of 10% w/v.

Chelating agent: previously tested chelating agent EDTA was replaced by EGTA or DTPA, two other chelating agents, at the same concentration of 150 μM.

$C_2$-$C_3$ alcohol: previously tested $C_2$-$C_3$ alcohol ethanol was replaced by isopropanol, at the same concentration of 0.5%.

Materials and Methods

Virus

The MVA virus used was MVA-MUC1 (TG4010), a recombinant MVA virus expressing MUC1 tumor associated antigen and interleukin 2 (see WO92/07000 and WO95/09241), diluted to an initial target titer between 8.0 $10^7$ and 2 $10^8$ IG/mL.

MVA-MUC1 was produced in chicken embryo fibroblast, and recovered and purified by a method comprising recovery of infected CEF culture, breakage of cells by mechanical means, and various purification steps that do not involve any step of treatment with a protease.

Tested Formulations

Tested formulations are represented in Table 16 below:

Analysis of Stability

Analysis of stability was done as described in Example 1.

Measure of Infectious Titers

Measure of infectious titers was done as described in Example 1.

Results

Figure 16A:
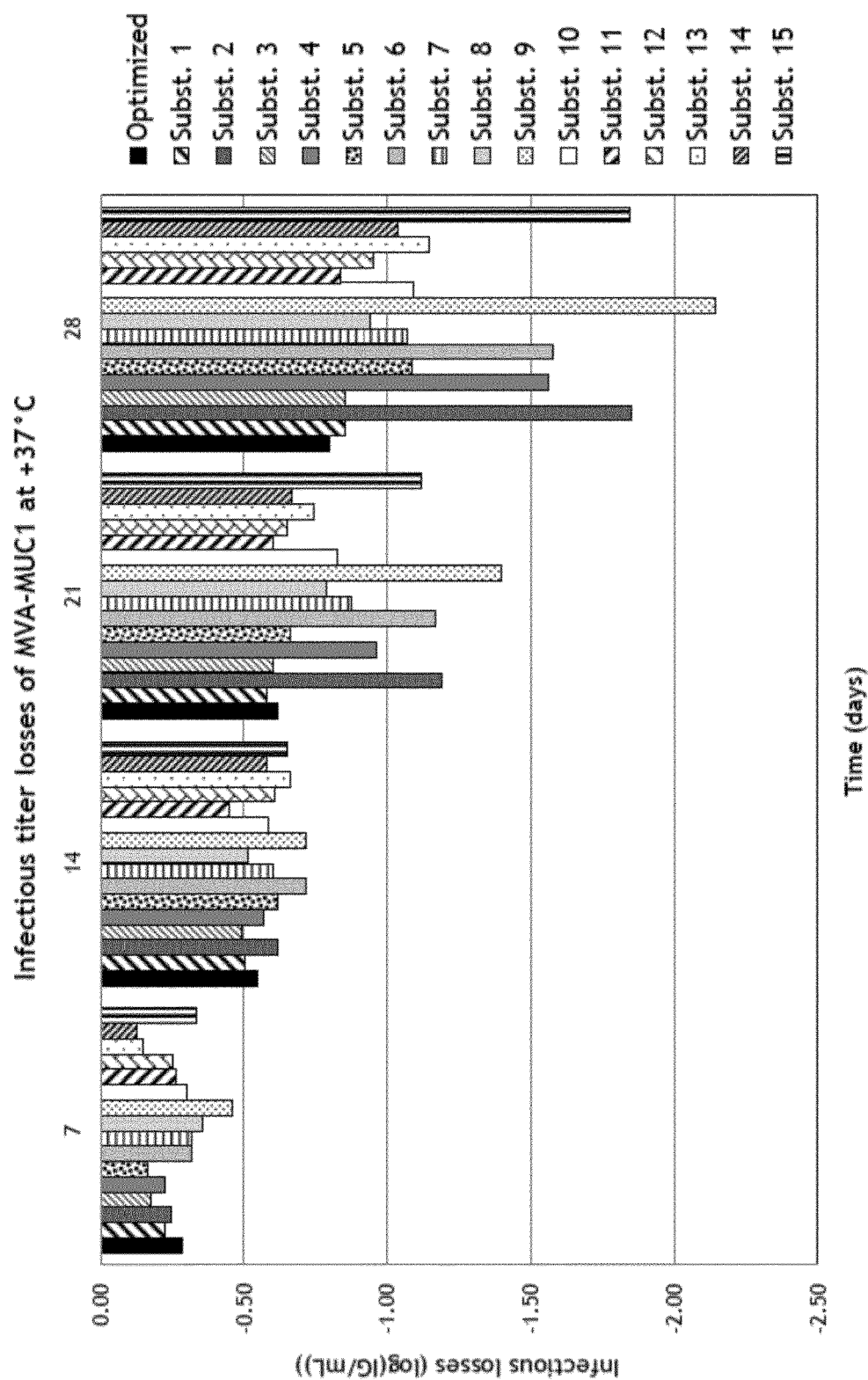
Figure 16B:
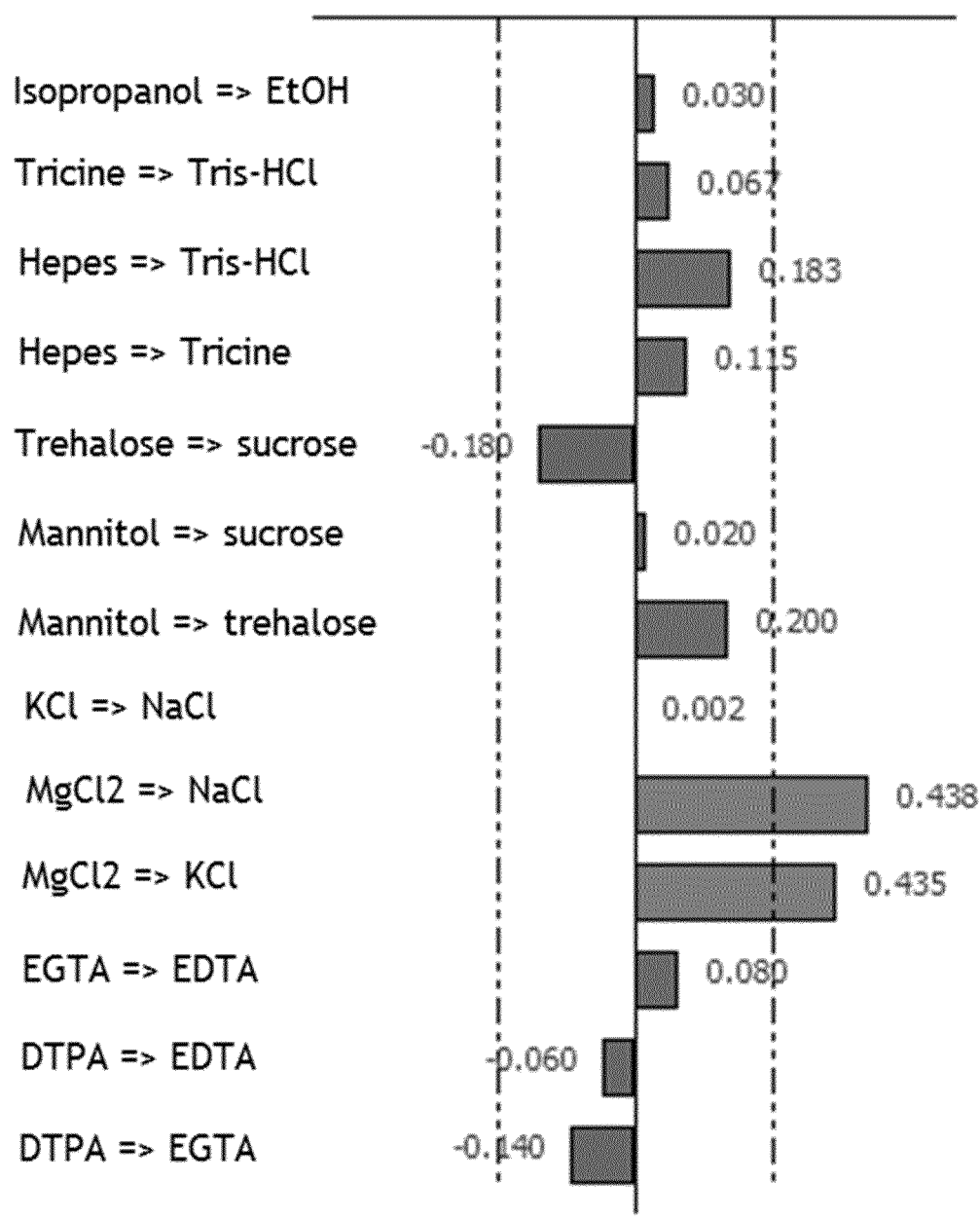
Figure 16C:
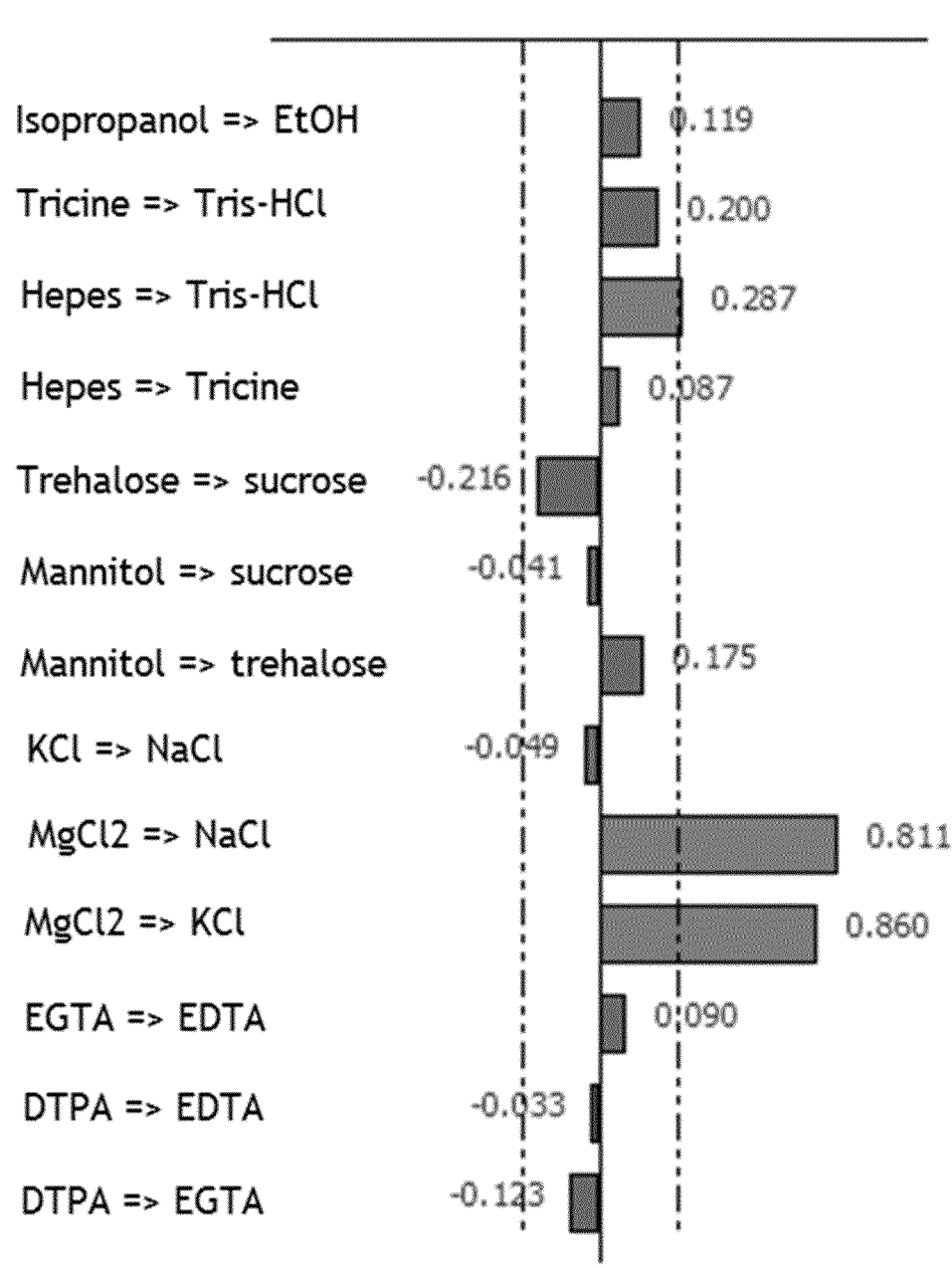

Infectious losses of the various tested formulations at +37° C. are represented in FIG. 16A.

The statistical significance of replacing the initially tested compound by one of the other compounds mentioned above was analyzed using NemrodW® software after 21 (FIG. 16B) or 28 (FIG. 16C) days at +37° C. Results show that:

Buffer: at day 21, replacing Tris-HCl by Tricine or HEPES buffer does not significantly impact MVA virus stability, although Tris-HCl appears to be slightly better for stabilizing MVA-MUC1. At day 28, replacing Tris-HCl by Tricine does not significantly impact MVA virus stability, although Tris-HCl appears to be slightly better, and HEPES buffer is less effective than Tris-HCl and Tricine.

Salt: replacing NaCl by KCl does not significantly impact MVA virus stability, after 21 or 28 days. In contrast, replacing NaCl or KCl by $MgCl_2$ has significant deleterious effect on MVA stability, both at day 21 and at day 28, further confirming that $MgCl_2$ may be deleterious at concentrations as low as 75 mM.

TABLE 16

Formulations tested for MVA-MUC1

| Formulation | Optimized | Subst. 1 | Subst. 2 | Subst. 3 | Subst. 4 | Subst. 5 |
|---|---|---|---|---|---|---|
| Alcohol (0.5% v/v) | EtOH | EtOH | EtOH | EtOH | isopropanol | isopropanol |
| Buffer (20 mM) | Tris-HCl | Tricine | Hepes | Tris-HCl | Tris-HCl | Tricine |
| Disaccharide or sugar alcohol (10% w/v) | Sucrose | Trehalose | Mannitol | Sucrose | Trehalose | Sucrose |
| Salt (75 mM) | NaCl | KCl | MgCl2 | NaCl | MgCl2 | NaCl |
| Chelating agent (150 μM) | EDTA | EGTA | DTPA | EDTA | EDTA | DTPA |
| Na Glutamate | 5 mM | 5 mM | 5 mM | 5 mM | 5 mM | 5 mM |

| Formulation | Subst. 6 | Subst. 7 | Subst. 8 | Subst. 9 | Subst. 10 |
|---|---|---|---|---|---|
| Alcohol (0.5% v/v) | isopropanol | isopropanol | EtOH | EtOH | EtOH |
| Buffer (20 mM) | Hepes | Tris-HCl | Tris-HCl | Tricine | Hepes |
| Disaccharide or sugar alcohol (10% w/v) | Sucrose | Mannitol | Mannitol | Sucrose | Sucrose |
| Salt (75 mM) | NaCl | KCl | NaCl | MgCl2 | KCl |
| Chelating agent (150 μM) | EGTA | EDTA | EGTA | EDTA | EDTA |
| Na Glutamate | 5 mM | 5 mM | 5 mM | 5 mM | 5 mM |

| Formulation | Subst. 11 | Subst. 12 | Subst. 13 | Subst. 14 | Subst. 15 |
|---|---|---|---|---|---|
| Alcohol (0.5% v/v) | EtOH | isopropanol | isopropanol | isopropanol | isopropanol |
| Buffer (20 mM) | Tris-HCl | Tris-HCl | Tricine | Hepes | Tris-HCl |
| Disaccharide or sugar alcohol (10% w/v) | Trehalose | Sucrose | Mannitol | Trehalose | Sucrose |
| Salt (75 mM) | NaCl | KCl | NaCl | NaCl | MgCl2 |
| Chelating agent (150 μM) | DTPA | DTPA | EDTA | EDTA | EGTA |
| Na Glutamate | 5 mM | 5 mM | 5 mM | 5 mM | 5 mM |

Disaccharide or sugar alcohol: replacing sucrose by mannitol does not significantly impact MVA virus stability. When replacing sucrose by trehalose, a small effect towards improved stability of MVA is noticed at days 21 and 28.

Chelating agent: replacing EDTA by DTPA or EGTA does not significantly impact MVA virus stability at days 21 and 28.

$C_2$-$C_3$ alcohol: replacing ethanol (EtOH) by isopropanol does not significantly impact MVA virus stability at days 21 and 28.

Figure 16D:
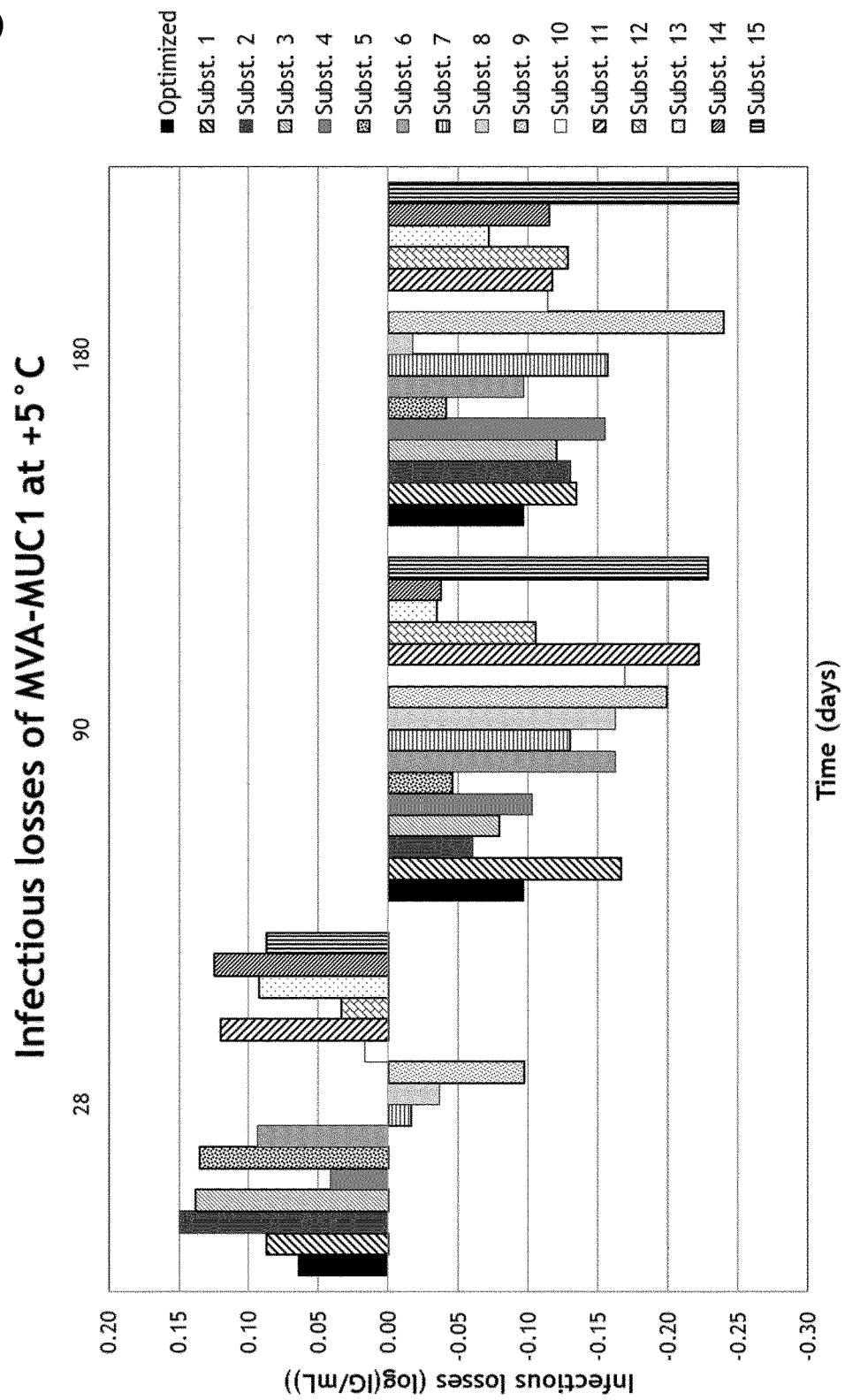

Infectious losses of the various tested formulations at +5° C. are represented in FIG. 16D. Results show that, at day 180, all tested formulations show very low infectious losses, all being inferior to 0.3 $\log_{10}$.

Conclusions

The above results clearly demonstrate that, in an optimized formulation according to the invention, initially tested compounds may be replaced by other compounds of the same family (Tris-HCl by another buffer with buffering capacity between pH 7 and 8, NaCl by another monovalent salt, sucrose by another disaccharide or a sugar alcohol, EDTA by another chelating agent, EtOH by another $C_2$-$C_3$ alcohol), without significantly altering the stability of vaccinia virus.

In contrast, NaCl or another monovalent salt should not be replaced by a divalent salt, thus confirming previous results showing deleterious effects of divalent salts when present at significant concentration (here 75 mM).

Example 6: Immunizing Properties In Vivo of a Stable Liquid MVA Formulation According to the Invention It was further verified if a stabilized liquid MVA formulation according to the invention had similar immunogenicity in vivo after 12 months storage than a just obtained MVA formulation.

Materials and Methods

MVA Virus

The MVA virus used was MVA-MUC1 (TG4010), a recombinant MVA virus expressing MUC1 tumor associated antigen and interleukin 2 (see WO92/07000 and WO95/09241), diluted to an initial target titer of 1 to 3 $10^8$ PFU/mL MVA-MUC1 was produced in chicken embryo fibroblast, and recovered and purified by a method comprising recovery of infected CEF culture, breakage of cells by mechanical means, and various purification steps that do not involve any step of treatment with a protease.

Tested Formulation and Storage

MVA-MUC1 was formulated in a liquid formulation containing Tris-HCl 20 mM, sucrose 10% w/v, NaCl 75 mM, EDTA 150 µM, EtOH 0.5% v/v, and Na glutamate 5 mM. For the immunogenicity test, were used either a just formulated MVA stored at −80° C. (T=0), or a formulated MVA stored during 12 months at +5° C.±3° C. (T=12 months).

Immunogenicity Test

The model used is a prophylactic model, in which the MVA-MUC1 vector is injected to mice before further administration of tumor cells expressing MUC1 antigen. Further details are given below:

$1^{st}$ Experiment:

Mice: C57BL/6 mice were used. Each group was composed of 20 animals:
Groups 1: formulation alone,
Group 2-4: MVA-MUC1 T=0 ($10^4$, $10^5$, or $10^6$ PFU),
Group 5-7: MVA-MUC1 T=12 months ($10^4$, $10^5$, or $10^6$ PFU).

Administration of products to be tested: each product was subcutaneously injected three times at one week interval (D0/D7/D14) for each condition (T=0/T=12 months). For each product, three doses ($10^4$, $10^5$, or $10^6$ PFU) were tested. In addition, as a negative control, formulation alone (without any MVA-MUC1 virus) was administered with the same protocol.

Administration of tumoral cells: one week after the last injection of virus/formulation, i.e. at day 21 (D21), RMA-MUC1 cells were injected subcutaneously.

Survival of mice, tumor presence and size were monitored, until day 107 (D107) or until the tumor volume was 2000 mm$^3$, at which time mice were sacrificed).

$2^{nd}$ Experiment:

The same model has been used to compare immunogenicity of formulation alone or MVA-MUC1 in formulation at T=0 and T=24 months, for a dose of $10^4$ PFU.

Results $1^{st}$ Experiment:

Table 17A below presents the percentage of mice that were tumor-free at day 86, depending on product (formulation alone or MVA-MUC1 after 0 or 12 months storage) and dose injected.

TABLE 17A

Percentage of mice that were tumor-free at day 86 depending on product (formulation or MVA-MUC1 after 0 or 12 months storage) and dose injected

| Product injected | Storage time | |
|---|---|---|
| | T = 0 | T = 12 months |
| Formulation alone | | 0% |
| MVA-MUC1 $10^4$ PFU | 40% | 45% |
| MVA-MUC1 $10^5$ PFU | 35% | 55% |
| MVA-MUC1 $10^6$ PFU | 35% | 30% |

The above results show that:
The tested liquid formulation does not, as such, induce an immune response protecting mice against RMA-MUC1 tumor cells, and
Storage for 12 months at +5° C.±3° C. of MVA-MUC1 in the tested formulation does not significantly affect the ability of MVA-MUC1 to induce an immune response protecting mice against RMA-MUC1 tumor cells.

$2^{nd}$ Experiment:

Table 17B below presents the percentage of mice that were tumor-free at day 65, depending on product (formulation alone or MVA-MUC1 after 0 or 24 months storage).

TABLE 17B

Percentage of mice that were tumor-free at day 65, depending on product (formulation alone or MVA-MUC1 after 0 or 24 months storage).

| Product injected | Storage time | |
|---|---|---|
| | T = 0 | T = 24 months |
| Formulation alone | | 0% |
| MVA-MUC1 $10^4$ PFU | 20% | 40% |

The above results show that:
The tested liquid formulations do not, as such, induce an immune response protecting mice against RMA-MUC1 tumor cell challenge, and Storage for 24 months at +5° C.±3° C. of MVA-MUC1 in the tested formulations do not significantly affect the ability of MVA-MUC1 to induce an immune response protecting mice against RMA-MUC1 tumor cells challenge.

Conclusion

The above data confirm that optimized formulations according to the invention not only maintain infectious virus titers during storage for two years, but also maintain the ability to induce a protective immune response in vivo.

Example 7: Protecting Effect of EDTA Against UV Damage

Vaccinia virus is known to be sensitive to UV damage (see LYTLE et al. J. Virol. 2005, 79(22):14244). The ability of various formulations to protect vaccinia virus against UV damage was tested in two independent experiments.

Materials and Methods

MVA Viruses

The MVA virus used was MVA-HCV (TG4040), a recombinant MVA virus expressing nonstructural HCV proteins (NS3, NS4 and NS5B) from HCV genotype 1 b strain ja (see WO2004/111082), which was diluted to an initial target titer of between $5 \cdot 10^7$ and $7 \cdot 10^7$ IG/mL for experiment 1 and between $3 \cdot 10^8$ and $5 \cdot 10^8$ IG/mL for experiment 2.

MVA-HCV was produced in chicken embryo fibroblast, and recovered and purified by a method comprising recovery of infected CEF culture, breakage of cells by mechanical means, and various purification steps that do not involve any step of treatment with a protease.

Tested Formulations

Tested formulations for MVA-HCV in experiment 1 are represented in Table 18 below:

TABLE 18

Formulations tested for MVA-HCV in varying light conditions (experiment 1).

|  | Control formulation | Optimized formulation |
|---|---|---|
| Tris-HCl (mM) | 10 | 10 |
| Sucrose (% w/v) | 5 | 5 |
| Na Glutamate (mM) | 10 | 10 |
| NaCl (mM) | 50 | 50 |
| EDTA (μM) | 0 | 150 |
| EtOH (% v/v) | 0 | 0.5 |
| pH | 7.5 | 7.5 |

Tested formulations for MVA-HCV in experiment 2 are represented in Table 19 below:

TABLE 19

Formulations tested for MVA-HCV in ICH light conditions (experiment 2).

|  | Control | EDTA + EtOH | EDTA | EtOH |
|---|---|---|---|---|
| Tris (mM) | 20 | 20 | 20 | 20 |
| Sucrose (% w/v) | 10 | 10 | 10 | 10 |
| Na Glutamate (mM) | 5 | 5 | 5 | 5 |
| NaCl (mM) | 75 | 75 | 75 | 75 |
| EDTA (μM) | 0 | 150 | 150 | 0 |
| EtOH (% v/v) | 0 | 0.5 | 0 | 0.5 |
| pH | 7.5 | 7.5 | 7.5 | 7.5 |

Light Conditions

Samples were stored in the following light conditions:
Without light,
Under PSM (Any light source that is designed to produce an output similar to the D65/ID65 emission standard such as an artificial daylight fluorescent lamp combining visible and ultraviolet (UV) outputs, xenon, or metal halide lamp. D65 is the internationally recognized standard for outdoor daylight as defined in ISO 10977 (1993). ID65 is the equivalent indoor indirect daylight standard. For a light source emitting significant radiation below 320 nm, an appropriate filter(s) may be fitted to eliminate such radiation) at room temperature, or Under ICH light (A near UV fluorescent lamp having a spectral distribution from 320 nm to 400 nm with a maximum energy emission between 350 nm and 370 nm; a significant proportion of UV should be in both bands of 320 to 360 nm and 360 to 400 nm. See ICH Q1B Photostability Testing of New Drug Substances and Products)

Analysis of Stability

Stability was analyzed at +25° C. (±2° C.) during 28 days.

Infectious tosses were calculated by subtracting the number of infectious genomes per mL (IG/mL) at the time measure to the initial number of IG/mL at day 0, and expressed as decimal logarithm ($\log_{10}$ (IG/mL)), abbreviated in the present description as log (IG/mL).

Measure of Infectious Titers

Measure of infectious titers was done as described in Example 1.

Results

Results are presented in FIGS. 17A and 17B for experiments 1 and 2, respectively.

In FIG. 17A, the effect of various light conditions (no light, PSM, or ICH) on stability of a control and an optimized formulation according to the invention has been tested. For all formulations, ICH light conditions result in significant destabilization, which is not surprising knowing the light sensitivity of vaccinia virus and the very strong lighting of ICH conditions. However, despite destabilization of all formulations, it is clear from FIG. 17A that using a liquid formulation according to the invention results in decreased destabilization of MVA-HCV (see infectious losses at days 2, 3 and 7 notably). It has to be noted that under these drastic light conditions, infectious titer losses observed with the control formulation were amplified, reaching 1 log at day 2.

In addition, in the case of more reasonable light conditions (PSM conditions), using a liquid formulation according to the invention also results in significantly decreased destabilization of MVA-HCV, the infectious losses after 28 days at +25° C. being largely lower than 0.5 log whereas exceeding 1 log after 21 days at 25° C. with the control formulation.

In FIG. 17B, the stabilizing effect under ICH light conditions of various formulations has been tested. As in FIG. 17A, an optimized formulation containing Tris-HCl, NaCl, Na glutamate, sucrose, EDTA and EtOH improves stability under ICH light conditions, better than a control formulation without EDTA and EtOH. In addition, FIG. 17B shows that the stabilizing effect is due to EDTA, since a formulation with EDTA but without EtOH has a similar stabilizing effect, while a formulation with EtOH but without EDTA is not better than the control formulation.

Conclusions

The above results clearly show that formulations according to the invention not only stabilize vaccinia virus in the absence of light, but also further protect vaccinia virus against degradation due to UV damage. This may be very helpful for limiting constraints on vaccinia virus storage in a liquid formulation.

Example 8: Robust Stabilization Effect of Claimed Formulations at Varying Ingredients Concentrations In order to test the robustness of the stabilizing effect of formulations according to the invention, several formulations containing varying concentrations of the distinct ingredients have been tested for their ability to stabilize an MVA vector.
Materials and Methods
Virus The MVA virus used was MVA-MUC1 (TG4010), a recombinant MVA virus expressing MUC1 tumor associated antigen and interleukin 2 (see WO92/07000 and WO95/09241), diluted to an initial target titer of 1 to 4 $10^8$ PFU/mL.

MVA-MUC1 was produced in chicken embryo fibroblast, and recovered and purified by a method comprising recovery of infected CEF culture, breakage of cells by mechanical means, and various purification steps that do not involve any step of treatment with a protease.
Tested Formulations Tested formulations are represented in Table 20 below:

TABLE 20

Formulations tested for MVA-MUC1

| Ingredient | Formulation n° | | | | | | | |
|---|---|---|---|---|---|---|---|---|
| | A | B | C | D | E | F | G | H |
| Tris-HCl (mM) | 30 | 50 | 50 | 10 | 10 | 50 | 30 | 30 |
| Na glutamate (mM) | 10 | 10 | 15 | 15 | 10 | 15 | 15 | 5 |
| Sucrose (% w/v) | 10 | 15 | 10 | 15 | 10 | 5 | 10 | 15 |
| NaCl (mM) | 50 | 100 | 150 | 50 | 100 | 100 | 50 | 100 |
| EDTA (µM) | 350 | 350 | 200 | 200 | 50 | 350 | 50 | 200 |
| EtOH (% v/v) | 0.55 | 0.1 | 1 | 0.55 | 0.1 | 0.55 | 1 | 1 |
| pH | 7.5 | | | | | | | |

Analysis of Stability

Analysis of stability was done as described in Example 1.
Measure of Infectious Titers Measure of infectious titers was done as described in Example 1.
Results Infectious losses of the various tested formulations at +37° C. are represented in FIG. 18.

At day 21 after formulation, all tested formulations had infectious losses inferior to 1 $\log_{10}$. At day 28, most tested formulations also had infectious losses inferior to 1 $\log_{10}$.
Conclusion The above data confirm that optimized formulations according to the invention have a robust stabilizing effect over a range of concentrations of ingredients contained in the formulation.

Example 9: Stabilization Effect of Claimed Formulations on Another Type of Poxvirus Materials and Methods
Virus A non recombinant pseudocowpox virus (parapoxvirus family) was used at an initial target titer of 1 to 3 $10^8$ PFU/mL.

Tested Formulations

Tested formulations are represented in Table 21 below:

TABLE 21

Formulations tested for pseudocowpox virus

| | Control | Formulation |
|---|---|---|
| Tris-HCl (mM) | 10 | 20 |
| Na glutamate (mM) | 10 | 5 |
| Sucrose (% w/v) | 5 | 10 |
| NaCl (mM) | 50 | 75 |
| EDTA (µM) | 0 | 150 |
| EtOH (% v/v) | 0 | 0.5 |
| pH | 8.0 | 7.5 |

Analysis of Stability

Analysis of stability was done as described in Example 1 at 37° C.
Measure of Infectious Titers Measure of infectious titers was done as described in Example 1.
Results Results are presented in FIG. 19, and show that the tested formulation according to the invention greatly stabilizes pseudocowpox virus. In particular, while infectious losses after 28 days at 37° C. are over 2.5 $\log_{10}$ for the control pseudocowpox virus in Tris and sucrose only, infectious losses after 28 days at 37° C. are only about 0.5 $\log_{10}$ for the formulated pseudocowpox virus.
Conclusion The above results clearly show that formulations according to the invention are also suitable to stabilize pseudocowpox virus, a poxvirus of the parapoxvirus family.

BIBLIOGRAPHIC REFERENCES

ANTOINE et al., 1998, Virol. 244, 365-396;
BREITBACH C J et al., 2011, Curr Pharm Biotechnol. Vol 12. No 12;
EVANS et al. 2004 October, J Pharm Sci., 93(10):2458-75;
EZZEDINE et al., 1991, New Biol 3:608;
GOEBEL et al., 1990, Virol. 179:247-266;
GOEBEL et al., 1990, Virol. 179:517-563;
GOMEZ et al., 2008, Current Gene Therapy, 8:97-120;
IVANOV et al., Experimental Pathology and Parasitology, 4/2000 Bulgarian Academy of Sciences;
JOHNSON et al., 1993, Virol. 196:381-401;
KIM J H et al., 2006 September, Mol Ther. 14(3):361-70;
KIRN et al., 2009 January, Nat Rev Cancer, 9(1):64-71;
LAMB et al., 1985, Eur. J. Biochem., 148:265-270;
LIU et al., 2004 Oct. 5, Proc Natl Acad Sci USA, 101 Suppl 2:14567-71;
LYTLE et al., 2005, J. Virol. 79(22):14244;
MASSEY R. et al., 1987, Nature, 328:457-458;
MAYR et al., 1975, Infection 3:6-16;
MOOLTEN, 1986, Cancer Res. 46:5276;
MULLEN et al., 1922 PNAS 89:33;
OSBORNE J D et al., 2007 Dec. 17, Vaccine, 25(52):8807-32;
REXROAD et al., June 2002, Cell Preservation Technology, 1(2): 91-104;
ROCHLITZ et al., 2003 August, J Gene Med., 5(8):690-9;
SHI et al., 2005 July, J Pharm Sci. 94(7):1538-51

TÕUGU V et al., 1994 Jun. 1, Eur J Biochem. 222(2):475-81;
EP1418942;
U.S. Pat. No. 4,675,187;
U.S. Pat. No. 5,879,924;
U.S. Pat. No. 7,456,009
U.S. Pat. No. 7,914,979,
US2007/0161085,
WO88/07378,
WO90/10459,
WO91/11201,
WO92/07000,
WO95/09241,
WO98/04705,
WO99/03885,
WO99/54481,
WO2004/111082,
WO2005/007840,
WO2005/007857,
WO2007/030668,
WO2007/077256,
WO2007/121894,
WO2007/147528,
WO2008/113078,
WO2009/004016,
WO2009/065546,
WO2009/065547,
WO2010/130753,
WO2014/009433,
WO2014/009438,
WO2014/029702,
WO2014/053571

The invention claimed is:

1. A liquid formulation comprising:

a) a poxvirus, b) a pharmaceutically acceptable buffer, c) a monovalent salt, d) a pharmaceutically acceptable disaccharide or sugar alcohol, e) a pharmaceutically acceptable chelating agent, and f) a $C_2$-$C_3$ alcohol in a concentration of 0.05 to 5% (v/v) and/or sodium glutamate in a concentration lower than 10 mM, wherein the pH of the formulation is between 6.5 and 8.5.

2. The liquid formulation according to claim 1, wherein said liquid formulation is free of a surfactant or comprises a surfactant at a concentration lower than 0.005% (w/v).

3. The liquid formulation according to claim 1, wherein said liquid formulation is free of divalent salts or comprises divalent salts at a concentration lower than 1 mM.

4. The liquid formulation according to claim 1, wherein said liquid formulation is free of histidine or comprises histidine at a concentration lower than 5 mM.

5. The liquid formulation according to claim 1, wherein said liquid formulation is free of arginine and methionine or comprises arginine at a concentration lower than 300 mM and/or methionine at a concentration lower than 60 mM.

6. The liquid formulation according to claim 1, wherein said poxvirus is present at a titer of at least $10^7$ PFU/mL.

7. The liquid formulation according to claim 1, wherein said poxvirus is at least semi-purified, comprising lower than 500 µg/dose of host cell proteins and lower than 10 ng/dose of host cell DNA.

8. The liquid formulation according to claim 1, wherein said pharmaceutically acceptable buffer has a buffering capacity between pH 7 and pH 8 and is present in a concentration of 10 to 50 mM.

9. The liquid formulation according to claim 1, wherein said pharmaceutically acceptable buffer has buffering capacity between pH 7 and pH 8 and is selected from TRIS-HCI, TRIS, HEPES, phosphate buffer comprising a mixture of $Na_2HPO_4$ and $KH_2PO_4$ or a mixture of $Na_2HPO_4$ and $NaH_2PO_4$, ACES, PIPES, MOPSO, BIS-Tris-Propane, BES, MOPS, TES, DIPSO, MOBS, TAPSO, HEPPSO, POPSO, TEA, EPPS, and Tricine buffers.

10. The liquid formulation according to claim 1, wherein said monovalent salt is present in a concentration of 10 to 1000 mM.

11. The liquid formulation according to claim 1, wherein said monovalent salt is selected from NaCl and KCl.

12. The liquid formulation according to claim 1, wherein said pharmaceutically acceptable disaccharide or sugar alcohol is present in a concentration of 5 to 20% (w/v).

13. The liquid formulation according to claim 1, wherein said pharmaceutically acceptable disaccharide or sugar alcohol is selected from sucrose, trehalose, maltose, lactose, mannitol, and sorbitol.

14. The liquid formulation according to claim 1, wherein said pharmaceutically acceptable chelating agent is present in a concentration of at least 50 µM.

15. The liquid formulation according to claim 1, wherein said pharmaceutically acceptable chelating agent is selected from ethylenediaminetetraacetic acid (EDTA), 1,2-bis(o-aminophenoxy)ethane-N,N,N',N'-tetraacetic acid (BAPTA), ethylene glycol tetraacetic acid (EGTA), dimercaptosuccinic acid (DMSA), diethylene triamine pentaacetic acid (DTPA), and 2,3-Dimercapto-1-propanesulfonic acid (DMPS).

16. The liquid formulation according to claim 1, wherein said $C_2$-$C_3$ alcohol is selected from ethanol and isopropanol.

17. The liquid formulation according to claim 1, wherein loss of infectious poxvirus titer in said liquid formulation is less than 1 $\log_{10}$ of infectious virus during storage for at least 1 week at +37° C.

18. The liquid formulation according to claim 1, wherein loss of infectious poxvirus titer in said liquid formulation is less than 0.3 $\log_{10}$ of infectious virus during storage for at least 12 months at +5° C.

19. The liquid formulation according to claim 1, wherein said poxvirus is an orthopoxvirus or a parapoxvirus.

20. The liquid formulation according to claim 19, wherein said poxvirus is a vaccinia virus.

21. The liquid formulation according to claim 20, wherein said vaccinia virus is a recombinant vaccinia virus comprising at least one exogenous sequence selected from:

an exogenous sequence encoding a cytosine deaminase (CDase) gene, an exogenous sequence encoding MUC1 and interleukin 2 (IL-2), an exogenous sequence encoding a human papillomavirus antigen, a hepatitis B antigen, a hepatitis C antigen, and an exogenous sequence encoding a mycobacterium antigen.

* * * * *